US012595500B2

(12) United States Patent
Peterson et al.

(10) Patent No.: US 12,595,500 B2
(45) Date of Patent: Apr. 7, 2026

(54) HIGH EFFICIENCY, SMALL VOLUME NUCLEIC ACID SYNTHESIS

(71) Applicants: LIFE TECHNOLOGIES CORPORATION, Carlsbad, CA (US); THERMO FISHER SCIENTIFIC GENEART GMBH, Regensburg (DE)

(72) Inventors: Todd Peterson, Coronado, CA (US); Axel Trefzer, Tegernheim (DE); Thomas Poehmerer, Regensburg (DE)

(73) Assignee: Life Technologies Corporation, Carlsbad, CA (US)

( * ) Notice: Subject to any disclaimer, the term of this patent is extended or adjusted under 35 U.S.C. 154(b) by 1157 days.

(21) Appl. No.: 17/405,548

(22) Filed: Aug. 18, 2021

(65) Prior Publication Data

US 2022/0177939 A1    Jun. 9, 2022

Related U.S. Application Data

(60) Continuation of application No. 16/736,258, filed on Jan. 7, 2020, now abandoned, which is a division of application No. 14/775,648, filed as application No. PCT/US2014/029500 on Mar. 14, 2014, now Pat. No. 10,563,240, application No. 17/405,548 is a continuation-in-part of application No. 17/320,572, filed on May 14, 2021, now Pat. No. 12,209,239, which is a continuation of application No. 16/678,576, filed on Nov. 8, 2019, now Pat. No. 11,046,953, which is a division of application No. 15/463,363, filed on Mar. 20, 2017, now Pat. No. 10,519,439, which is a division of application No. 14/730,824, filed on Jun. 4, 2015, now abandoned, which is a continuation of application No. 13/627,819, filed on Sep. 26, 2012, now abandoned.

(60) Provisional application No. 61/784,752, filed on Mar. 14, 2013, provisional application No. 61/539,303, filed on Sep. 26, 2011.

(51) Int. Cl.
    *C12P 19/34*        (2006.01)
    *C12N 15/10*        (2006.01)
(52) U.S. Cl.
    CPC .......... *C12P 19/34* (2013.01); *C12N 15/1031* (2013.01); *C12N 15/1093* (2013.01)
(58) Field of Classification Search
    None
    See application file for complete search history.

(56) References Cited

U.S. PATENT DOCUMENTS

| | | |
|---|---|---|
| 4,652,639 A | 3/1987 | Stabinsky |
| 5,512,439 A | 4/1996 | Hornes et al. |
| 5,514,789 A | 5/1996 | Kempe |
| 5,538,848 A | 7/1996 | Livak et al. |
| 5,580,759 A | 12/1996 | Yang et al. |
| 5,624,827 A | 4/1997 | Rosenblum et al. |
| 5,738,829 A | 4/1998 | Kempe |
| 5,786,464 A | 7/1998 | Seed |
| 5,807,522 A | 9/1998 | Brown et al. |
| 5,837,858 A | 11/1998 | Brennan |
| 5,851,808 A | 12/1998 | Elledge et al. |
| 5,869,644 A | 2/1999 | Shortle et al. |
| 5,888,732 A | 3/1999 | Hartley et al. |
| 6,083,726 A | 7/2000 | Mills, Jr. et al. |
| 6,093,302 A | 7/2000 | Montgomery |
| 6,110,668 A | 8/2000 | Strizhov et al. |
| 6,143,527 A | 11/2000 | Pachuk et al. |
| 6,143,557 A | 11/2000 | Hartley et al. |
| 6,335,438 B1 | 1/2002 | Fonnum |
| 6,355,412 B1 | 3/2002 | Stewart et al. |
| 6,391,576 B1 | 5/2002 | Tsuchida et al. |
| 6,426,183 B1 | 7/2002 | Beattie |
| 6,444,111 B1 | 9/2002 | Montgomery |
| 6,472,184 B1 | 10/2002 | Hegemann |
| 6,495,318 B2 | 12/2002 | Harney |
| 6,509,156 B1 | 1/2003 | Stewart et al. |
| 6,521,427 B1 | 2/2003 | Evans |
| 6,887,431 B1 | 5/2005 | Vann et al. |
| 6,964,861 B1 | 11/2005 | Gerard et al. |
| 7,202,264 B2 | 4/2007 | Ravikumar et al. |
| 7,211,148 B2 | 5/2007 | Vann et al. |
| 7,323,321 B2 | 1/2008 | Rayapati et al. |
| 7,347,975 B2 | 3/2008 | Vann et al. |
| 7,348,391 B2 | 3/2008 | Ravikumar et al. |
| 7,384,606 B2 | 6/2008 | Vann et al. |
| 7,670,823 B1 | 3/2010 | Hartley et al. |

(Continued)

FOREIGN PATENT DOCUMENTS

| | | |
|---|---|---|
| CN | 101397587 A | 4/2009 |
| CN | 201901669 U | 7/2011 |

(Continued)

OTHER PUBLICATIONS

Tsvetanova et al., "Genetic Assembly Tools for Synthetic Biology," Methods Enzymol. 2011, 498:327-348. (Year: 2011).*

(Continued)

*Primary Examiner* — Kaijiang Zhang

(57) ABSTRACT

The disclosure generally relates to compositions and methods for the production of nucleic acid molecules. In some aspects, the invention allows for the microscale generation of nucleic acid molecules, optionally followed by assembly of these nucleic acid molecules into larger molecules. In some aspects, the invention allows for efficient production of nucleic acid molecules (e.g., large nucleic acid molecules such as genomes).

14 Claims, 26 Drawing Sheets

Specification includes a Sequence Listing.

(56)         References Cited

U.S. PATENT DOCUMENTS

| | | | |
|---|---|---|---|
| 7,670,832 B2 | 3/2010 | Wittwer et al. | |
| 7,704,690 B2 | 4/2010 | Young | |
| 7,820,412 B2 | 10/2010 | Belshaw et al. | |
| 7,829,505 B2 | 11/2010 | Gupta et al. | |
| 7,833,759 B2 | 11/2010 | Padgett et al. | |
| 7,838,210 B2 | 11/2010 | Ludwig et al. | |
| 8,173,368 B2 | 5/2012 | Staehler et al. | |
| 8,507,197 B2 | 8/2013 | Palaniappan | |
| 9,279,149 B2 | 3/2016 | Efcavitch et al. | |
| 2001/0026935 A1 | 10/2001 | Ackley et al. | |
| 2002/0143166 A1 | 10/2002 | Pires et al. | |
| 2003/0143331 A1 | 7/2003 | Iyer et al. | |
| 2003/0152984 A1 | 8/2003 | Aygun et al. | |
| 2004/0219516 A1 | 11/2004 | Bennett et al. | |
| 2004/0229229 A1 | 11/2004 | Cheo et al. | |
| 2004/0265863 A1 | 12/2004 | Chesnut et al. | |
| 2006/0115850 A1 | 6/2006 | Schatz | |
| 2006/0127920 A1 | 6/2006 | Church et al. | |
| 2006/0128006 A1 | 6/2006 | Gerhardt et al. | |
| 2007/0034513 A1 | 2/2007 | Maurer et al. | |
| 2007/0059752 A1 | 3/2007 | Cook | |
| 2007/0141557 A1 | 6/2007 | Raab et al. | |
| 2007/0231805 A1 | 10/2007 | Baynes et al. | |
| 2007/0292954 A1 | 12/2007 | Elledge | |
| 2008/0113361 A1 | 5/2008 | Vann | |
| 2008/0145913 A1 | 6/2008 | Padgett et al. | |
| 2008/0187969 A1 | 8/2008 | Castle et al. | |
| 2008/0281466 A1 | 11/2008 | Vann | |
| 2008/0318243 A1 | 12/2008 | Haga et al. | |
| 2009/0032401 A1 | 2/2009 | Ronaghi et al. | |
| 2009/0275086 A1 | 11/2009 | Gibson et al. | |
| 2009/0324546 A1 | 12/2009 | Notka et al. | |
| 2010/0062495 A1 | 3/2010 | Liu et al. | |
| 2010/0137143 A1 | 6/2010 | Rothberg et al. | |
| 2010/0184020 A1 | 7/2010 | Beer | |
| 2010/0216648 A1 | 8/2010 | Staehler et al. | |
| 2010/0291633 A1 | 11/2010 | Selmer et al. | |
| 2011/0010931 A1 | 1/2011 | Sheu | |
| 2011/0109031 A1 | 5/2011 | Stauber | |
| 2011/0114490 A1 | 5/2011 | Pamula et al. | |
| 2011/0119778 A1 | 5/2011 | Liss | |
| 2011/0124049 A1 | 5/2011 | Li et al. | |
| 2011/0165630 A1 | 7/2011 | Maresca et al. | |
| 2012/0053087 A1 | 3/2012 | Gibson et al. | |
| 2012/0202709 A1 | 8/2012 | Bergo | |
| 2012/0220497 A1 | 8/2012 | Jacobson et al. | |
| 2012/0270748 A1 | 10/2012 | Chee et al. | |
| 2013/0109596 A1 | 5/2013 | Peterson et al. | |
| 2013/0123121 A1 | 5/2013 | Schwartz et al. | |
| 2013/0189688 A1 | 7/2013 | Shoemaker et al. | |
| 2014/0135233 A1 | 5/2014 | Stuelpnagel et al. | |
| 2016/0186166 A1 | 6/2016 | Poehmerer et al. | |

FOREIGN PATENT DOCUMENTS

| | | | |
|---|---|---|---|
| CN | 103945931 A | 7/2014 | |
| JP | 2006291359 A | 10/2006 | |
| WO | WO-9322480 A1 | 11/1993 | |
| WO | WO-9801221 A1 | 1/1998 | |
| WO | WO-0061647 A1 | 10/2000 | |
| WO | WO-03020415 A2 | 3/2003 | |
| WO | WO-2005089110 A2 | 9/2005 | |
| WO | WO-2006105037 A2 | 10/2006 | |
| WO | WO-2007087377 A2 | 8/2007 | |
| WO | WO-2009140671 A2 | 11/2009 | |
| WO | WO-2009145818 A1 | 12/2009 | |
| WO | WO-2010006166 A2 | 1/2010 | |
| WO | WO-2010040531 A2 | 4/2010 | |
| WO | WO-2010138182 A2 | 12/2010 | |
| WO | WO-2010147078 A1 | 12/2010 | |
| WO | WO-2011071943 A1 | 6/2011 | |
| WO | WO-2011102802 A1 | 8/2011 | |
| WO | WO-2011109031 A1 | 9/2011 | |
| WO | WO-2013049227 A2 | 4/2013 | |
| WO | WO-2014065758 A1 | 5/2014 | |
| WO | WO-2014153188 A2 | 9/2014 | |
| WO | WO-2016079269 A1 | 5/2016 | |
| WO | WO-2016094512 A1 | 6/2016 | |
| WO | WO-2017100283 A1 | 6/2017 | |

OTHER PUBLICATIONS

Smith et al., "Generating a synthetic genome by whole genome assembly: phiX174 bacteriophage from synthetic oligonucleotides," PNAS 2003, 100:15440-15445. (Year: 2003).*

Lashkari et al., "An automated multiplex oligonucleotide synthesizer: Development of high-throughput, low-cost DNA synthesis," PNAS 1995, 92:7912-7915. (Year: 1995).*

Egeland et al., "Electrochemically directed synthesis of oligonucleotides for DNA microarray fabrication," Nucleic Acids Res. 2005, 33(14):e125. (Year: 2005).*

EP21187827.7, Corrected Extended European Search Report, Jun. 27, 2022, 10 pages.

A Venier, et al., "Combining Medium Effects and Cofactor Catalysis: Metal-Coordinated Synzymes Accelerate Phosphate Transfer by 1 08", Chemistry: A European Journal, vol. 15, No. 45, Nov. 16, 2009, 12371-12380.

Azevedo, et al., "An ordered collection of Bacillus subtilis DNA segments cloned in yeast artificial chromosomes", Proceedings of the National Academy of Sciences, vol. 90, No. 13, Jul. 1, 1993, 6047-6051.

Beier M., et al., "Versatile Derivatisation of Solid Support Media for Covalent Bonding on DNA-Microchips", Nucleic Acids Research, May 1, 1999, vol. 27, No. 9, pp. 1970-1977.

Belfort M., et al., "Homing Endonucleases: Keeping The House In Order," Nucleic Acids Research, Sep. 1, 1997, vol. 25, No. 17, pp. 3379-3388.

Berry, et al., "New Methods to Transport Fluids in Micro-Sized Devices", Lincoln Laboratory Journal, vol. 17, No. 2, 2008, 74-80 (www.ll.mit.edu/publications/journal/pdf/vol17 no2/17 2 4Berry. pdf).

Burk, , "Sustainable production of industrial chemicals from sugars.", International Sugar Journal, vol. 112, 2010, 30-35.

Cardullo R.A., et al., "Detection of Nucleic Acid Hybridization by Non Radiative Fluorescence Resonance Energy Transfer," Proceedings of the National Academy of Sciences, Dec. 1988, vol. 85, pp. 8790-8794.

Chiu S-H, et al., "An air-bubble-actuated micropump for on-chip blood transportation", Lab on a Chip, vol. 9, No. 11, Jan. 1, 2009 (Jan. 1, 2009), XP055483472, pp. 1524-1533.

Chiu, Sheng-Hung et al., "An air-bubble-actuated micropump for on-chip blood transportation", Lab on a Chip. The Royal Society of Chemistry, vol. 9, No. 11, Jun. 7, 2009, 1481-1644.

Choi S, et al., "Microfluidic-based biosensors toward point-of-care detection of nucleic acids and proteins", Microfluidics and Nanofluidics, vol. 10, No. 2, Jun. 2, 2010 (Jun. 2, 2010), pp. 231-247.

Cook, Brian , "Introduction to fuel cells and hydrogen technology", Engineering Science and Education Journal Dec. 2002, 205-216.

Dexter, , "A Theory of Sensitized Luminescence in Solids", The Journal of Chemical Physics. vol. 21, 1953, 836-850.

Egeland, et al., "Electrochemically directed synthesis of oligonucleotides for DNA microarray fabrication", Nucleic Acids Research, vol. 33, No. 14, 2005, e125 (1-7).

Egeland, Ryan D. , "An Electrochemical System for DNA Microarray Fabrication", Thesis Presented to the University of Oxford in fulfilment of the thesis requirement for the degree of Doctor of Philosophy in Biochemistry. Lincoln College, University of Oxford, England, 2003, 1-301.

EP21187827.7, Extended European Search Report, Feb. 7, 2022, 8 pages.

Extended European Search Report for Application No. 19174248.5, mailed Jul. 31, 2019, 10 pages.

Florescu O, et al., "On-chip magnetic separation of superparamagnetic beads for integrated molecular analysis", Journal of Applied Physics, American Institute of Physics, US, vol. 107, No. 5, Mar. 12, 2010 (Mar. 12, 2010), XP012133648, pp. 054702-1-054702-10.

(56) References Cited

OTHER PUBLICATIONS

Fodor S.P., et al., "Light-directed, Spatially Addressable Parallel Chemical Synthesis," Science, Feb. 15, 1991, vol. 251, pp. 767-773.

Fuhrmann, et al., "Removal of mismatched bases from synthetic genes by enzymatic mismatch cleavage", Nucleic Acids Research vol. 33, No. 6, 2005, e58 (1-8).

Gibson, , "Enzymatic Assembly of Overlapping DNA Fragments", Methods in Enzymology, vol. 498, Jan. 1, 2011, 349-361.

Gibson, et al., "Complete Chemical Synthesis, Assembly, and Cloning of a Mycoplasma genitalium Genome", Science, vol. 319, No. 5867, Feb. 29, 2008, 1215-1220.

Gyuris, et al., "High-efficiency transformation of Saccharomyces cerevisiae cells by bacterial minicell protoplast fusion.", Molecular and Cellular Biology, vol. 6, No. 9, Sep. 1986, 3295-3297.

Heuer, et al., "Cloning of prokaryotic genomes in yeast artificial chromosomes: Application to the population genetics fo Pseudomonas aeruginosa", Electrophoresis, vol. 19, No. 4, Apr. 1998, 486-494.

Hochstrasser, et al., "Distance distribution in a dye linked oligonucleotide determined by time-resolved fluorescence energy transfer", Biophysical Chemistry, vol. 45, No. 2, Dec. 1992, 133 -141.

Huang, et al., "A simple, high sensitivity mutation screeing using Ampligase mediated T7 endonuclease I and Surveyor nuclease with microfluidic capillary electrophoresis", Electroohoresis vol. 33, No. 5, Mar. 21, 2012, 788-796.

Intl PCT/US2012/057363, , "International Preliminary Report mailed", Apr. 10, 2014, 1-9.

Intl PCT/US2012/057363, , "International Search Report and Written Opinion mailed", Nov. 6, 2013, 1-13.

Intl PCT/US2012/057363, , "Partial International Search Report mailed", Jun. 21, 2013, 1-3.

Intl PCT/US2014/029500, , "International Search Report and Written Opinion mailed", Sep. 17, 2014, 1-12.

Invitrogen/Life Technologies, , "GENEART® High-Order Genetic Assembly Systems", Catalog Nos. A13285, A13286, 2013, 1-45.

Invitrogen/Life Technologies, et al., "GENEART® Seamless Cloning and Assembly Kit", Catalog No. A13288, 2014, 1-28.

Jordan, et al., "Asymmetric phosphorylation through catalytic P(III) phosphoramidite transfer: Enantioselective synthesis of d-myo-inositol-6-phosphate", Proceedings of the National Academy of Sciences vol. 107, 48, Nov. 30, 2010, 20620-20624.

Kornberg, , "Eukaryotic transcriptional control.", Trends Cin ell Biology, vol. 9, No. 12, Dec. 1999, M46-M49.

Kozak, , "Initiation of translation in prokaryotes and eukaryotes.", Gene, vol. 234, No. 2, Jul. 9, 1999, 187-208.

Kurakazu, Tomoaki et al., "Selective retrieval of microparticles in microchambers using electrolytically generated bubbles for cell array applications", Sensors and Actuators B: Chemical. vol. 159, 2011, 229-233.

Kuspa, et al., "Physical mapping of the Myxococcus xanthus genome by random cloning in yeast artificial chromosomes", Proceedings of the National Academy of Science, vol. 86, No. 22, Nov. 1, 2012,8917-8921.

Landy, A., "Dynamic, Structural, and Regulatory Aspects of .lamda. Site-Specific Recombination," Annu. Rev. Biochem. 58:913-949, American Chemical Society, Washington D.C. (1989).

Lartique, et al., "Genome transplantation in bacteria: changing one species to another.", Science vol. 317, No. 5838, Epub. Jun. 28, 2007, Aug. 3, 2007, 632-638.

Lashkari, et al., "An automated multiplex oligonucleotide synthesizer: Development of high-throughput, low-cost DNA synthesis", Proceedings of the National Academy of Sciences, vol. 92, No. 17, Aug. 15, 1995, 7912-7915.

Liang, et al., "Recombination-Based DNA Assembly and Mutagenesis Methods for Metabolic Engineering", Methods in Molecular Bioloav. vol. 834, Jan. 1, 2012, 93-109.

Life Technologies Corporation, , "Ion AmpliSeq™ Cancer Panel", Application Note, Products Catalog No. 44 72395, Jan. 10, 2012, 1-4.

Liu P et al., "Integrated DNA purification, PCR, sample cleanup, and capillary electrophoresis microchip for forensic human identification", Lab on a Chip, vol. 11, No. 6, Jan. 1, 2011 (Jan. 1, 2011), pp. 1041-1048.

Livak K.J., et al., "Oligonucleotides With Fluorescent Dyes At Opposite Ends Provide A Quenched Probe System Useful For Detecting Pcr Product And Nucleic Acid Hybridization," PCR Methods and Applications, Jun. 1995, vol. 4, No. 6, pp. 357-362.

Luder, , "Acids and Bases: Their Relationship to Oxidizing and Reducing Agents", Journal of Chemical Education, Jan. 1942, 24-26.

Matzas, Mark et al., "High-Fidelity Gene Synthesis by Retrieval of Sequence-Verified DNA Identified Using High-Throughput Pyrosequencing", Nature Biotechnology, vol. 28, No. 12,Dec. 2010, 1291-1294.

Maurer et al., "Electrochemically Generated Acid and Its Containment to 100 Micron Reaction Areas for the Production of DNA Microarrays", PLos One, vol. 1, No. 1, e34, Dec. 2006, pp. 1-7.

Mhlanga M.M., et al., "Using Molecular Beacons to Detect Single-Nucleotide Polymorphisms with Real-Time PCR," Methods, 2001, vol. 25, pp. 463-471.

Nakazawa, et al., "Efficient selection of hybrids by protoplast fusion using drug resistance markers and reporter genes in Saccharomyces cerevisiae.", Journal of Bioscience and Bioenaineerina. vol. 98, No. 5, 2004, 353-358.

Ninomiya, et al., "Highly Efficient Gene Replacement in Neurospora Strains Deficient for Nonhomologous End-Joining", Proceedings of the National Academy of Sciences, vol. 101, No. 33, Aug. 17, 2004, 12248-12253.

Notka et al., Reprogramming a GFP Reporter Gene Subjects It To Complex Lentiviral Gene Regulation, Methods in Molecular Biology, vol. 813, 2012, 85-106.

Ogura M., et al., "Use of the Fluorescent dye YOYO-1 to Quantify Oligonucleotides Immobilized on Plastic Plates," Biotechniques, 1994, vol. 16, No. 6, pp. 1032-1034.

Pachuk, et al., "Chain reaction cloning: a one-step method for directional ligation of multiple DNA fragments", Gene, vol. 243, Nos. 1-2, Feb. 8, 2000, 19-25.

PCT/US2014/029500, , "International Preliminary Report on Patentability mailed on Sep. 24, 2015", Sep. 24, 2015, 8 Pages.

Quan, et al., "Circular polymerase extension cloning for high-throughput cloning of complex and combinatorial DNA libraries", Nature Protocols vol. 6, Feb. 3, 2011, 242-251.

Quan J., et al., "Circular Polymerase Extension Cloning of Complex Gene Libraries and Pathways", Plos One, Public Library of Science, US, vol. 4, No. 7, e6441, Jul. 30, 2009, XP002729117, 6 pages.

Rodiger S, et al., "Nucleic acid detection based on the use of microbeads: a review", Mikrochimica Acta., vol. 181, Nos. 11-12, Apr. 11, 2014 (Apr. 11, 2014), XP055608312, pp. 1151-1168.

Saha, , "Quantitation of HIV-1 by real-time PCR with a unique fluorogenic probe", Journal of Virological Methods vol. 93, Nos. 1-2, 33-42, Apr. 2001.

Sauer, "Site-specific recombination: developments and applications", Current Opinion in Biotechnology, vol. 5, No. 5, Oct. 1994 ; pp. 521-527.

Selvin P. R., "Fluorescence Resonance Energy Transfer Methods in Enzymology," 1995, vol. 246, pp. 300-334.

Sista R.S, et al., "Heterogeneous immunoassays using magnetic beads on a digital microfluidic platform", Lab on a Chip, vol. 8, No. 12, Oct. 14, 2008, pp. 2188-2196.

Smith, et al., "Generating a synthetic genome by whole genome assembly: phix174 bacteriophage from synthetic oligonucleotides", Proceedings of the National Academy of Sciences, vol. 100, No. 26, Dec. 23, 2003, 15440-15445.

Steinberg, , "Long-Range Nonradiative Transfer of Electronic Excitation Energy in Proteins and Polypeptides", Annual Review of Biochemistry, vol. 40, Jul. 1971, 83-114.

Stinchcomb, et al., "Eukaryotic DNA segments capable of autonomous replication in yeast", Proceedings of the National Academy of Sciences vol. 77, No. 8, Aug. 1, 1980, 4559-4563.

Stryer, "Fluorescence Energy Transfer as a Spectroscopic Ruler", Annual Review of Biochemistry. vol. 47, Jul. 1978, 819-846.

(56)     References Cited

OTHER PUBLICATIONS

Tan, Wei-Heong et al., "A trap-and-release integrated microfluidic system for dynamic microarray applications", PNAS. vol. 104, No. 4, Jan. 23, 2007, 1146-1151.

Tsvetanova, et al., "Genetic Assembly Tools for Synthetic Biology", Methods in Enzymology, vol. 498, 2011, 327-348.

U.S. Appl. No. 09/177,387, filed Oct. 23, 1998, , "Pending U.S. Appl. No. 09/177,387, filed Oct. 23, 1998", 1-158 pages.

Vent Ana Medical Systems, Inc., , "LCS (predilute)", www.ventana. com/product/208 ?tvoe=218 Cataloq No. 650-010, Apr. 15, 2014, 1.

Wang, et al., "Design and Synthesis of New Fluorogenic HIV Protease Substrates Based on Resonance Energy Transfer", Tetrahedron Letters, vol. 31, No. 45, 1990, 6493-6496.

Wang, Yiwen et al., "Rapid Sizing of Short Tandem Repeat Alleles Using Capillary Array Electrophoresis and Energy-Transfer Fluorescent Primers", Analytical Chemistry, vol. 67, No. 7, American Chemical Society, Apr. 1, 1995, 1197-1203.

Yang et al., "Construction of recombinant DNA by exonuclease recession", Nucleic Acids Research, 1993, vol. 21, No. 8, pp. 1889-1893.

Zhang et al., "SLiCE: a novel bacterial cell extract-based DNA cloning method," Nucleic Acids Res. 2012, 40(8):e55, published online Jan. 12, 2012. (Year: 2012).

Zhou X., et al., "Microfluidic PicoArray Synthesis of Oligonucleotides and Simultaneous Assembling of Multiple DNA Sequences," Nucleic Acids Research, Oct. 2004, vol. 32, No. 18, pp. 5409-5417.

* cited by examiner

Overlapping DNA fragments
(natural or synthetic)
and a yeast vector

Cotransformation

Homologous
Recombination

| Domain Linker | | | | | | | | | | |

| Codon | 85 | 86 | 87 | 88 | 89 | 90 | 91 | 92 | 93 | 94 | 95 | |
|-------|-----|-----|-----|-----|-----|-----|-----|-----|-----|-----|-----|---|
| WT | TTC | CTT | CCT | GCT | ACT | GGT | GGC | GTT | TTC | CGU | AAT | (SEQ ID NO:39) |
| | Phe | Leu | Pro | Ala | Thr | Gly | Gly | Val | Phe | Arg | Asn | (SEQ ID NO:40) |
| Variant 1 | | | | GGT | ACC | ACT | | | | | | |
| | | | | Gly | Thr | Thr | | | | | | |
| Variant 2 | | | | GGT | | | | | | | | |
| | | | | Gly | | | | | | | | |
| Variant 3 | | | | CCT | ACC | ACC | ACT | | | | | |
| | | | | Pro | Thr | Thr | Thr | | | | | |

FIG. 12A

Domain Linker

| Codon | 85 | 86 | 87 | 88 | 89 | 90 | 91 | 92 | 93 | 94 | 95 | |
|---|---|---|---|---|---|---|---|---|---|---|---|---|
| WT | TTC | CTT | CCT | GCT | ACT | GGT | GGC | GTT | TTC | CGU | AAT | (SEQ ID NO:39) |
|  | Phe | Leu | Pro | Ala | Thr | Gly | Gly | Val | Phe | Arg | Asn | (SEQ ID NO:40) |
| V1 | TTC | CTC | CCC | GCC | ACC | GGC | GGC | GTC | TTC | AGA | AAT | (SEQ ID NO:41) |
|  | Phe | Leu | Pro | Ala | Thr | Gly | Gly | Val | Phe | Arg | Asn | (SEQ ID NO:40) |
| V2 | TTC | CTA | CCA | GCC | ACT | GGA | GGC | GTC | TTC | AGG | AAT | (SEQ ID NO:42) |
|  | Phe | Leu | Pro | Ala | Thr | Gly | Gly | Val | Phe | Arg | Asn | (SEQ ID NO:40) |
| V3 | TTC | CTT | CCG | GCA | ACA | GGT | GGG | GTG | TTC | CGC | AAT | (SEQ ID NO:43) |
|  | Phe | Leu | Pro | Ala | Thr | Gly | Gly | Val | Phe | Arg | Asn | (SEQ ID NO:40) |
| V4 | TTC | CTT | CCC | GCG | ACC | GGT | GGG | GTA | TTC | CGU | AAC | (SEQ ID NO:44) |
|  | Phe | Leu | Pro | Ala | Thr | Gly | Gly | Val | Phe | Arg | Asn | (SEQ ID NO:40) |

FIG. 12B

HIGH EFFICIENCY, SMALL VOLUME NUCLEIC ACID SYNTHESIS

CROSS-REFERENCE TO RELATED APPLICATIONS

This application is a continuation of U.S. application Ser. No. 16/736,258 filed on Jan. 7, 2020, now pending, which is a division of U.S. application Ser. No. 14/775,648 filed on Sep. 11, 2015, now issued as U.S. Pat. No. 10,563,240, which is a 371 National Phase Application of International Application No. PCT/US2014/029500 filed Mar. 14, 2014, which claims the benefit of priority under 35 U.S.C. § 119 (e) of U.S. Provisional Application No. 61/784,752 filed Mar. 14, 2013, the entire disclosures of which are incorporated herein by reference. This application is also a continuation-in-part of U.S. application Ser. No. 17/320,572 filed May 14, 2021, now pending, which is a continuation of U.S. application Ser. No. 16/678,576 filed Nov. 8, 2019, now issued as U.S. Pat. No. 11,046,953, which is a divisional of U.S. patent application Ser. No. 15/463,363 filed Mar. 20, 2017, now issued as U.S. Pat. No. 10,519,439, which is a divisional of U.S. application Ser. No. 14/730,824 filed Jun. 4, 2015, now abandoned, which is a continuation of U.S. application Ser. No. 13/627,819 filed Sep. 26, 2012, now abandoned, which claims the benefit of priority under 35 U.S.C. § 119 (e) of U.S. Provisional Application No. 61/539, 303 filed Sep. 26, 2011, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Feb. 25, 2022, is named LT00586_1USCON_SL.txt and is 12,261 bytes in size.

FIELD OF THE INVENTION

The disclosure generally relates to compositions and methods for the production of nucleic acid molecules. In some aspects, the invention allows for the microscale generation of nucleic acid molecules, optionally followed by assembly of these nucleic acid molecules into larger molecules. In some aspects, the invention allows for efficient production of nucleic acid molecules (e.g., large nucleic acid molecules such as genomes).

BACKGROUND

Production of nucleic acid molecules can be fairly simple or complex depending on factors such as the type of nucleic acid molecules to be produced. For example, historically, short single stranded nucleic acid molecules such as primers have been typically generated by chemical synthesis (see, e.g., U.S. Pat. No. 5,837,858, the disclosure of which is incorporated herein by reference). Further, longer nucleic acid molecules have typically been generated by polymerase chain reaction (PCR). One disadvantage of PCR is that generally template nucleic acid is required.

Many nucleic acid synthesis methods have limited capabilities for the generation of large de novo nucleic acid molecules. One aspect of the current disclosure is to address this limitation.

SUMMARY OF THE INVENTION

The invention relates, in part, to compositions and methods for the synthesis of nucleic acid molecules. The invention further relates to compositions and methods for the assembly of nucleic acid molecules to form molecules such as plasmids, chromosomes and genomes.

In some aspects, the invention relates to multiwell plates for non-template directed synthesis of nucleic acid molecules. In some embodiments, the plate comprises a bead (e.g., a magnetic bead) located in each of a plurality of wells of the plate and an electrochemically generated acid (EGA) being present in one or more of the plurality of wells. Instead of or in addition to having EGA in one or more wells, wells of the plate may contain other reagents set out elsewhere wherein associated with the synthesis of nucleic acid molecules.

Bead sizes used in the practice of the invention may vary widely but include beads with diameters between 0.01 μm and 100 μm, 0.005 μm and 100 μm, 0.005 μm and 10 μm, 0.01 μm and 100 μm, 0.01 μm and 1,000 μm, between 1.0 μm and 2.0 μm, between 1.0 μm and 100 μm, between 2.0 μm and 100 μm, between 3.0 μm and 100 μm, between 0.5 μm and 50 μm, between 0.5 μm and 20 μm, between 1.0 μm and 10 μm, between 1.0 μm and 20 μm, between 1.0 μm and 30 μm, between 10 μm and 40 μm, between 10 μm and 60 μm, between 10 μm and 80 μm, or between 0.5 μm and 10 μm. As one skilled in the art would recognize, when solid particle fall below a particular size, they begin to act acquire attributes of fluids (e.g., form the equivalent of colloidal suspensions). Thus, in some instances (e.g., with the use of beads below about 500 nm in diameter), it may be desirable to treat the bead as a fluid. This may mean removal of a bead from a magnetic tip, for example, by agitation, washing, or with the use of a surfactant.

In specific embodiments of the invention, the bead size may be chosen depending on the size of the well to allow only one single bead to occupy a well. In other embodiments, more than one bead (or nucleic acid synthesis substrates of other shapes) may be in some of all of the wells. In some instances, the number beads per well may be between two and twenty, between two and thirty, between two and ten, between four and twenty, between four and ten, between four and fifty, etc.

The number of wells may also vary widely and is limited by factors such as the amount of nucleic acid to be produced and technical factors such as manufacturability and mechanic factors related to use (e.g., the lower size limit of magnetic bead extractors). In any event, the number of wells may be in number, for example, between 10 and 10,000,000, between 10 and 5,000,000, between 10 and 2,000,000, between 10 and 1,000,000, between 10 and 800,000, between 10 and 650,000, between 10 and 500,000, between 500 and 500,000, between 10 and 50,000, between 1,000 and 500,000, between 10,000 and 500,000, between 20,000 and 500,000, or between 1,000 and 50,000. Further, multiwell surfaces have been prepared with wells numbering in the range of 10 million. Thus, under some instances, the number of wells may be less than 5 million, 10 million, 20 million, etc.

The total volume of each well is another item which may vary and may be, for example, between $1.0 \times 10^{-9}$ μl and 50 μl, between $1.0 \times 10^{-9}$ μl and 10 μl, between $1.0 \times 10^{-9}$ μl and 1.0 μl, between $1.0 \times 10^{-9}$ μl and 0.1 μl, between $1.0 \times 10^{-9}$ μl and $1.0 \times 10^{-2}$ μl, between $1.0 \times 10^{-9}$ μl and $1.0 \times 10^{-3}$ μl, between $1.0 \times 10^{-9}$ μl and $1.0 \times 10^{-4}$ μl, between $1.0 \times 10^{-9}$ μl and 50 μl, between $1.0 \times 10^{-5}$ μl and $1.0 \times 10^{-6}$ μl, between $1.0 \times 10^{-9}$ μl and $1.0 \times 10^{-7}$ μl, between $2.5 \times 10^{-9}$ μl and $1.0 \times 10^{-2}$ μl, between $2.5 \times 10^{-9}$ μl and $1.0 \times 10^{-3}$ μl, between $2.5 \times 10^{-9}$ μl and $1.0 \times 10^{-4}$ μl, between $2.5 \times 10^{-9}$ μl and $1.0 \times 10^{-5}$ μl, between $2.5 \times 10^{-9}$ μl and $1.0 \times 10^{-6}$ μl, between $1.0 \times 10^{-8}$ µl and $1.0 \times 10^{-6}$ µl, between $1.0 \times 10^{-8}$ µl and $1.0 \times 10^{-5}$ µl, between $1.0 \times 10^{-7}$ µl and $1.0 \times 10^{-5}$ µl, between $1.0 \times 10^{-7}$ µl and $1.0 \times 10^{-4}$ µl, between $1.0 \times 10^{-7}$ µl and $1.0 \times 10^{-3}$ µl, between $1.0 \times 10^{-7}$ µl and $1.0 \times 10^{-2}$ µl, between 0.1 µl and 50 µl, between 0.01 µl and 50 µl, between 0.01 µl and 25 µl, between 0.01 µl and 15 µl, between 0.01 µl and 10 µl, between 0.001 µl and 50 µl, between 0.001 µl and 5 µl, between 0.001 µl and 1 µl, between 0.001 µl and 0.01 µl, or between 0.001 µl and 1 µl.

In many instances, multiwell plates of the invention or multiwell plates suitable for use with the invention will be operably connected to either one electrode or a set (e.g., one or several pairs) of electrodes. As discussed elsewhere herein, these electrodes can be used to generate a microenvironment associated with catalysis of one or more chemical reactions (e.g., EGA for nucleotide deprotection).

In some embodiments, multiwell plates of the invention or multiwell plates suitable for use with the invention will be connected to microfluidic channels for the introduction and removal of reagents. This allows for efficient and automated controlling of reagents.

The invention also provides method for the generation of assembled nucleic acid molecules formed from smaller chemically synthesized nucleic acid molecules. In some embodiments, such method may comprise one or more of the following steps:

(a) synthesizing a plurality of nucleic acid molecules, wherein each nucleic acid molecule is prepared in a microquantity in the well of a plate;

(b) combining the nucleic acid molecules generated in (a), or a portion thereof, to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

In some embodiments, the joining of nucleic acid molecules present in the pool will be mediated by polymerase chain reaction (PCR).

In some embodiments step (b) may further comprise combining nucleic acid molecules generated in (a) with nucleic acid molecules obtained by other means to form a pool, wherein said other means include PCR, restriction enzyme digest or exonuclease treatment. In some instances, the assembled nucleic acid molecule generated in (c) and/or (e) may be assembled and introduced into a vector (e.g., a cloning vector, a destination vector, etc.).

The number of nucleic acid molecules assembled by methods of the invention can vary and, when appropriate, will correlate with the number of pooled nucleic acid molecules. In any event, nucleic acid molecules assembled in methods of the invention may be composed of at least five other (e.g., smaller) nucleic acid molecules (e.g., from about five to about five thousand, from about five to about twenty thousand, from about five to about one hundred thousand, from about fifty to about five thousand, from about fifty to about twenty thousand, from about fifty to about one hundred thousand, from about one hundred to about five thousand, from about one hundred to about one hundred thousand, from about five hundred to about five thousand, from about five hundred to about one hundred thousand, etc. nucleic acid molecules).

Nucleic acid molecules assembled by methods of the invention may vary greatly and include molecules of at least 20 kilobases (e.g., between from about 0.5 kilobase and to about 10 megabases, between from about 0.5 kilobase and to about 5 megabases, between from about 0.5 kilobase and to about 1 megabase, between from about 0.5 kilobase and to about 500 kilobases, between from about 0.5 kilobase and to about 100 kilobases, between from about 0.5 kilobase and to about 10 megabases, between from about 0.5 kilobase and to about 1 kilobase, between from about 1 kilobase and to about 10 megabases, between from about 10 kilobases and to about 5 megabases, between from about 1 kilobase and to about 5 megabases, between from about 1 kilobase and to about 2 megabases, between from about 1 kilobase and to about 1 megabase, between from about 1 kilobase and to about 500 kilobases, between from about 10 kilobases and to about 1 megabases, between from about 10 kilobase and to about 500 kilobases, between from about 10 kilobase and to about 100 kilobases, etc.).

Nucleic acid molecule assembled by methods of the invention may be, for example, single stranded, partly single stranded or double stranded, closed, circular (e.g., a plasmid); nicked, circular; or linear (e.g., a plasmid, a chromosome, etc.). Further, methods of the invention may be performed such that two or more (e.g., two, three, four, five, six, ten, twenty, etc.) assembled nucleic acid molecules are simultaneously formed in the same reaction mixture.

The invention further provides methods for producing product nucleic acid molecules. In some instances such the methods comprise:

(a) designing a product nucleic acid molecule of between 10 kilobases and 500 kilobases in size (e.g., between 500 bases and 500 kilobases, between 500 bases and 100 kilobases, between 500 bases and 1 kilobase, between 500 bases and 800 bases between 2 kilobases and 100 kilobases, between 2 kilobases and 50 kilobases, between 2 kilobases and 5 kilobases, between 10 kilobases and 500 kilobases, between 10 kilobases and 300 kilobases, between 10 kilobases and 200 kilobases, between 10 kilobases and 100 kilobases, between 10 kilobases and 50 kilobases, etc.), wherein the product nucleic acid molecule is defined by nucleotide sequence;

(b) synthesizing a plurality of individual nucleic acid molecules which differ in nucleotide sequence, wherein each individual nucleic acid molecule is synthesized to prepare a quantity of between 1,000 and $1.0 \times 10^9$ copies and wherein the individual nucleic acid molecules are capable of hybridizing with one or more of the other individual nucleic acid molecules;

(c) combining the individual nucleic acid molecules synthesized in (b) under conditions which allow for hybridization of the individual nucleic acid molecules under conditions which allow for the formation of at least one larger nucleic acid molecule; and (d) combining the at least one larger nucleic acid molecule formed in (c) with one or more additional nucleic acid molecules to form the product nucleic acid molecule, wherein the product nucleic acid molecule contains less than one sequence error per kilobase.

In many instances, an error correction process is employed during generation of product nucleic acid molecules. One place in the above work flow where an error correction process may be performed is after step (b). Error correction processes are described elsewhere herein and will often include the use of one or more mis-match repair endonuclease.

The number of individual nucleic acid molecule synthesized as part of the preparation of product nucleic acid molecules may vary greatly but include between 1,000 and $1.0\times10^9$ copies, between 1,000 and $1.0\times10^8$ copies, between 1,000 and $1.0\times10^7$ copies, between 1,000 and $1.0\times10^6$ copies, between 1,000 and $1.0\times10^5$ copies, between $2.0\times10^7$ and $1.0\times10^9$ copies, between $5.0\times10^7$ and $1.0\times10^9$ copies, between $7.0\times10^7$ and $1.0\times10^9$ copies, between $2.0\times10^7$ and $8.0\times10^8$ copies, between $2.0\times10^7$ and $5.0\times10^8$ copies, between $5.0\times10^4$ and $1.0\times10^9$ copies, between $1.0\times10^6$ and $1.0\times10^9$ copies, between $1.0\times10^7$ and $1.0\times10^8$ copies; etc.

In many instances, polymerase chain reactions may be used to amplify the at least one larger nucleic acid molecule formed in step (c) in the above product nucleic acid molecule preparation processes.

Plate formats for the synthesis of nucleic acid molecules are described elsewhere herein and they may be used in the above product nucleic acid molecule preparation processes. Further, when individual nucleic acid molecules are synthesized on beads, wherein each bead may be contained in a well. Further, beads used in this aspect of the invention, as well as other aspects of the invention may be, for example of sizes such as between 1 μm and 100 μm in diameter, between 5 μm and 50 μm in diameter, between 3 μm and 100 μm in diameter, between 5 μm and 100 μm in diameter, between 20 μm and 100 μm in diameter, between 5 μm and 60 μm in diameter, between 10 μm and 100 μm in diameter, etc. In some embodiments beads may be of a size of about 30 μm in diameter (e.g. between 28 and 32 μm).

The invention also includes methods for producing nucleic acid molecule in small amounts and with high sequence fidelity. In some aspects, the invention includes a method for generating a nucleic acid molecule, the method comprising synthesizing the nucleic acid molecule in a total amount of between $3.0\times10^6$ and $4.0\times10^8$ molecules, wherein the number of sequence errors is between 1 in 100 to 1 in 500.

The invention thus includes methods for the generation of collections of nucleic acid molecules, including methods comprising:

(a) synthesizing a plurality of nucleic acid molecules, wherein each nucleic acid molecule is prepared in a microquantity;

(b) joining some or all of the nucleic acid molecules present in the pool formed in (b) to form a plurality of larger nucleic acid molecules; and (c) assembling the plurality of larger nucleic acid molecules to form the collection of nucleic acid molecules, wherein the collection of nucleic acid molecules from bioinformatic information selected from the group consisting of:

(1) a copy DNA (cDNA) library containing only DNA corresponding to messenger RNA (mRNA) molecules;

(2) a partial cDNA library containing DNA molecules corresponding to less than the full complement of mRNA molecules found in the cell type that the bioinformatic information was derived from; and (3) a collection of nucleic acid molecules in which some or all of the nucleic acid molecules are codon altered variants of nucleic acid molecules found in the cell type that the bioinformatic information was derived from.

The invention also provides method for the generation of self replicating nucleic acid molecules formed from smaller chemically synthesized nucleic acid molecules. In some embodiments, such method may comprise one or more of the following steps:

(a) synthesizing a plurality of nucleic acid molecules, wherein each nucleic acid molecule is prepared in a microquantity in a plate;

(b) joining some or all of the nucleic acid molecules present in the pool formed in (b) to form a plurality of larger nucleic acid molecules; and (c) assembling the plurality of larger nucleic acid molecules to form the self replicating nucleic acid molecule.

Self replicating nucleic acid molecules prepared by methods of the invention include chromosomes, artificial chromosomes (such as, for example, BACs or YACs), plasmids and genomes (e.g., genomes such as viral, nuclear, prokaryotic (e.g., bacterial, algal, etc.) chloroplast, or mitochondrial genomes).

The invention also includes methods for synthesizing and assembling nucleic acid molecules which encode more than one expression product, the methods comprising:

(a) synthesizing a plurality of nucleic acid molecules, wherein each nucleic acid molecule is prepared in a microquantity;

(b) joining some or all of the nucleic acid molecules present in the pool formed in (a) to form a plurality of larger nucleic acid molecules; and (c) assembling the plurality of larger nucleic acid molecules to form the nucleic acid molecules which encode more than one expression product.

In various aspects of the invention, the more than one expression products may be proteins involved in the same biological pathway. In more specific aspects, the more than one expression products may be proteins involved in the same biological pathway are enzymes that catalyze a series of chemical reactions in the biological pathway. Further, such chemical reactions in the same biological pathway may be sequential reactions in the sense that one chemical reaction follows another either directly (directly sequential) or after one or more intervening reaction has occurred.

Biological pathway referred to herein include those that results in the production of an end product selected from the group consisting of (a) biofuel precursors; (b) antibiotics or antibiotic precursors; (c) food components; (d) a chemical intermediate (e.g., 1,4-butanediol, 2,3-butanediol, benzene, butadiene, 2-butanol, 3-hydroxypropionic acid, acrylic acid, adipic acid, aminocaproic acid, caprolactam, acetylene, n-butanol, cyclohexanone, fumarate, 4-hydroy butyrate, GBL/BDO, hexamethylenediamine, isobutanol, isopropanol, n-propanol, long chain alcohol, methacrylic acid/methyl methacrylate, methyl ethyl ketone, propylene, putrescine, muconic acid, p-toluate, terepthalic acid, acetic acid, glucaric acid); (d) industrial enzymes, and (e) natural products. Biofuel precursors include alcohols selected from the group consisting of (a) butanol; (b) pentanol; (c) hexanol; (d) heptanol; and (e) octanol. Food components include livestock feed components, including amino acids selected from the group consisting of: (a) L-lysine; (b) L-threonine; (c) L-methionine; (d) L-leucine; (e) L-isoleucine: (f) L-valine, and (g) Homoserine.

Assembled nucleic acid molecules may be introduced into any number of cells including prokaryotic and eukaryotic cell. Examples of such cells include members of the genus *Corynebacterium* (e.g., *Corynebacterium glutamicum*), *Pseudomonas* sp. (*Pseudomonas aeruginosa*), *Saccharomyces cerevisiae*, *Bacillus* sp. (*Bacillus lentus, Bacillus coagulans, Bacillus subtilis*), *Aspergillus* sp. (*Aspergillus terreus, A. niger, Aspergillus versicolorr*), *Streptomycetes* spp. (*Streptomyces griseus, Streptomyces violaceans, Streptomyces hygroscopicus, Streptomyces octosporus*), *Clostridium*

(clostridia), *Clostridium thermocellum, Clostridium aceto-butylicum, Clostridium beijerinckii, Clostridium butyricum, Clostridium ljungdahlii, Clostridium aceticum, Clostridium saccharobutylicum, Clostridium saccharoperbutylacetoni-cum, Trichoderma reesei (Hypocrea jecorina), Kluyveromy-ces (lactis), Neurospora crassa, Yarrowia lipolitica, Humi-cola (Humicola grisea), Hansenula polymorpha (Pichia angusta), Acetobacters, Zymomonas, Chrysosporium, Ther-moanaerobacter, Pichia stipitis, Myxobacteria, Mortierella isabellina, Actinobacillus succinogenes, Anaerobio spiril-lum succiniciproducens, Pichia kudriavzevii/Issatchenkia orientalis (Yeast) (Candida krusei), Bifidobacterium, Bacil-lus coagulans GBI-30, Bifidobacterium animalis subsp. lac-tis BB-12, Bifidobacterium longum subsp. infantis 35624, Lactobacillus acidophilus NCFM, Lactobacillus paracasei, Lactobacillus johnsonii Lal, Lactobacillus plantarum, Lac-tobacillus reuteri, Saccharomyces boulardii, Lactobacillus rhamnosus, Lactobacillus acidophilus NCFM, Bifidobacte-rium bifidum BB-12, Lactobacillus casei, Lactobacillus plantarum, Xanthomonas (X. campestris),* Archea *(Halobac-terium* sp. NRC-1, *Sulfolobus tokodaii, Sulfolobus tokodaii Methanocaldococcus jannaschii, Thermoplasma acidophi-lum* and *Thermoplasma volcanium), Rhodobacter sphaeroi-des, Ralstonia eutropha, Sporomusa* species, *Clostridium ljungdahlii, Clostridium aceticum, Moorella thermoacetica, Geobacter* species, *Shewanella* sp, *Candida glabrata, Can-dida sonorensis, Candida tropicalis, Hansenula polymor-pha, Issatchenkia orientalis, Kluyveromyces lactis, Kluyveromyces marxianus, Kluyveromyces thermotolerans, Pichia stipidis, Saccharomyces bayanus, Saccharomyces bulderi, Saccharomyces uvarum, Sachharomyces cerevisiae, Schizosaccharomyces pombe, Yarrowia Lipolytica, Zygo-saccharomyces bailii,* Biodegredation *(Aromatoleum aro-maticum, Dechloromonas aromatica, Desulfitobacterium hafniense, Geobacter metallireducens, Alcanivorax borku-mensis, Mycobacterium tuberculosis), Deinococcus radio-durans, Actinoplanes regularis, Nocardia orientalis, Actino-corrulia regularis, Tolypocladium inflatum, Monascus ruber, Janibacter limonus, Actinomadura* sp., *Verucosispora* sp., *Muscodar albus,* and *Neurospora crassa.*

As one skilled in the art would understand, many aspects of the invention are well suited for automation. Automated systems are often driven by software which may perform repetitive tasks, especially when integrated with hardware designed for micromanipulation of components and reagent flows. Thus, according to various embodiments described herein, methods of assembling and synthesizing nucleic acids may be implemented on a computing system. Further, according to various embodiments described herein, proces-sor-executable instructions for assembling and synthesizing nucleic acids. Thus, in some aspects the invention includes non-transitory computer-readable storage media encoded with instructions, executable by a processor, for generating assembled nucleic acid molecule, the instructions compris-ing instructions for:

(a) synthesizing a plurality of nucleic acid molecules, wherein each nucleic acid molecule is prepared in a microquantity in the well of a plate;

(b) combining the nucleic acid molecules generated in (a) to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

The invention also includes systems for generating assembled nucleic acid molecules, the system comprising:
a processor; and
a memory encoded with processor-executable instructions for:

(a) synthesizing a plurality of nucleic acid molecules, wherein each nucleic acid molecule is prepared in a microquantity in the well of a plate;

(b) combining the nucleic acid molecules generated in (a) to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

The invention also includes methods (e.g., in vitro meth-ods) for assembling nucleic acid molecules. One such method comprises: (a) forming a reaction mixture of (1) one or more insert nucleic acid molecule, one or more acceptor nucleic acid molecule, a plurality of oligonucleotides, wherein each oligonucleotide shares sequence complemen-tarity with (i) one terminus of the insert nucleic acid mol-ecule and the insertion site of the acceptor nucleic acid molecule or (ii) one terminus of two different insert nucleic acid molecules and wherein the number of oligonucleotides may be represented by the formula $O=2+2I$, where O is the number of oligonucleotides and I is the number of insert nucleic acid molecules, (2) a cell extract, and (3) a protein composition comprising an exonuclease and, optionally, a single stranded binding protein, and (b) incubating the reaction formed in (a) under conditions which allow for the introduction of the insert nucleic acid molecule into the acceptor nucleic acid molecule.

Oligonucleotides used in this aspect of the invention may be set up in pairs, where the members of each pair the oligos are fully complementary or partially complementary (offset oligos) to each other.

Cell extracts used in the practice of the invention may be obtained from any number of organisms, including single cellular organisms such as selected bacteria (e.g., *Escheri-chia coli, Bacillus subtilis,* etc.) and fungi (e.g., *Schizosac-charomyces pombe, Saccharomyces cerevisiae,* etc.) When cells extracts from prokaryotic cells (e.g., bacteria cells) are prepared and used in methods of the invention, the cell may or may not express redET genes. One exemplary strain that may be used in methods of the invention includes cells of *Escherichia coli* strain DH10B.

Exonuclease activity used in methods of the invention may also be provided by a DNA polymerase or protein with exonuclease activity not having DNA polymerase activity.

The number of inserts that may be used in assembly methods of the invention varies greatly but may be in the range of from about 1 to about 30, from about 1 to about 20, from about 1 to about 100, from about 2 to about 15, from about 2 to about 10, from about 2 to about 8, from about 3 to about 30, from about 3 to about 15, from about 3 to about 10, from about 3 to about 8, from about 3 to about 6, from about 3 to about 5, from about 3 to about 4, from about 2 to about 6, etc.

The number of oligonucleotides employed may be represented by the formula O=2+2I, where O is the number of oligonucleotides and I is the number of insert nucleic acid molecules. Thus, when the following number of inserts (I) are used, the following numbers of oligonucleotides (O) will often be used I=1, O=4; I=2, O=6; I=3, O=8; I=4, O=10, I=5, O=12, etc.

BRIEF DESCRIPTION OF THE FIGURES

FIGS. 12A-12B show a series of variant nucleic acid molecules that may be prepared by methods of the invention and their encoded amino acid sequences. FIG. 12A shows variant nucleic acid molecules that encode different amino acid sequences.

FIG. 12B shows variant nucleic acid molecules that use different codons but encode the same amino acid sequence.

FIG. 14A is a top view and FIG. 14B is a side view. Shown in the figure are fluidic channels 1401, two electrodes associated with each channel/row of wells 1402 and a series of wells containing nucleic acid synthesis substrates (e.g., individual beads) located in wells 1400. In some embodiments, the wells will be spaced 300 μm apart and will be cylindrical in shape with a diameter of 40 μm and a depth of 35 μm.

FIG. 24A shows the assembled nucleic acid molecules generated using the methods for the $1^{st}$ PCR reaction set out in TABLE 18. PCR reactions in 1 and 2 shared the same formulation (0.03 μM overlapping oligonucleotides, 0.2 mM dNTPs, 1× PHUSION® HF buffer (New England Biolabs) and 0.02 U/μl PHUSION®High-Fidelity DNA Polymerase (New England Biolabs)). A single mastermix was employed to load 1280 wells (33 nl each) of a single QUANTSTUDIO™ 12KFlex OPENARRAY® Plate (Life Technologies, Corp) using the OPENARRAY® ACCUFILL™ System (Life Technologies Corp) the remaining 1792 wells were filled with sterile water. Oil overlay distribution and chip sealing was performed according to the manufacturer's directions. Cycling parameters and instrumentation are shown in TABLE 18. Once the assembly PCR reaction concluded, the contents of the chip were recovered by loosening the inlet valve and centrifuging the chip in a 50 ml tube at 2000 rpm for 2 min. Approximately 40 μl of the aqueous phase was recovered by standard pipetting. Products were analyzed by agarose electrophoresis. Numbers indicate samples 1 and 2 described in TABLE 18. "M" stands for molecular weight standards FIG. 24B shows assembled nucleic acid molecules generated using the methods for the $1^{st}$ and $2^{nd}$ PCR reactions set out in TABLE 18. Briefly, products of the $1^{st}$ PCR reactions described in (A) were used as a template for the $2^{nd}$ PCR reaction, which shared the same formulation regardless of the instrument, volume and conditions used (0.3 μM outermost forward oligonucleotide, 0.3 μM outermost reverse oligonucleotide, 0.2 mM dNTPs, 1× PHUSION® HF buffer (New England Biolabs) and 0.02 U/μl PHUSION® High-Fidelity DNA Polymerase (New England Biolabs)). Reagent loading and product recovery from the QUANTSTUDIO™ 12KFlex OPENARRAY® Plates (Life Technologies Corp), was performed as described in (A). Products were analyzed by agarose electrophoresis using the volumes depicted on the figure. Numbers indicate samples 1, 2, 3, and 4 described in TABLE 18. "M" stands for molecular weight standards.

DETAILED DESCRIPTION OF THE INVENTION

Definitions

Figure 1:
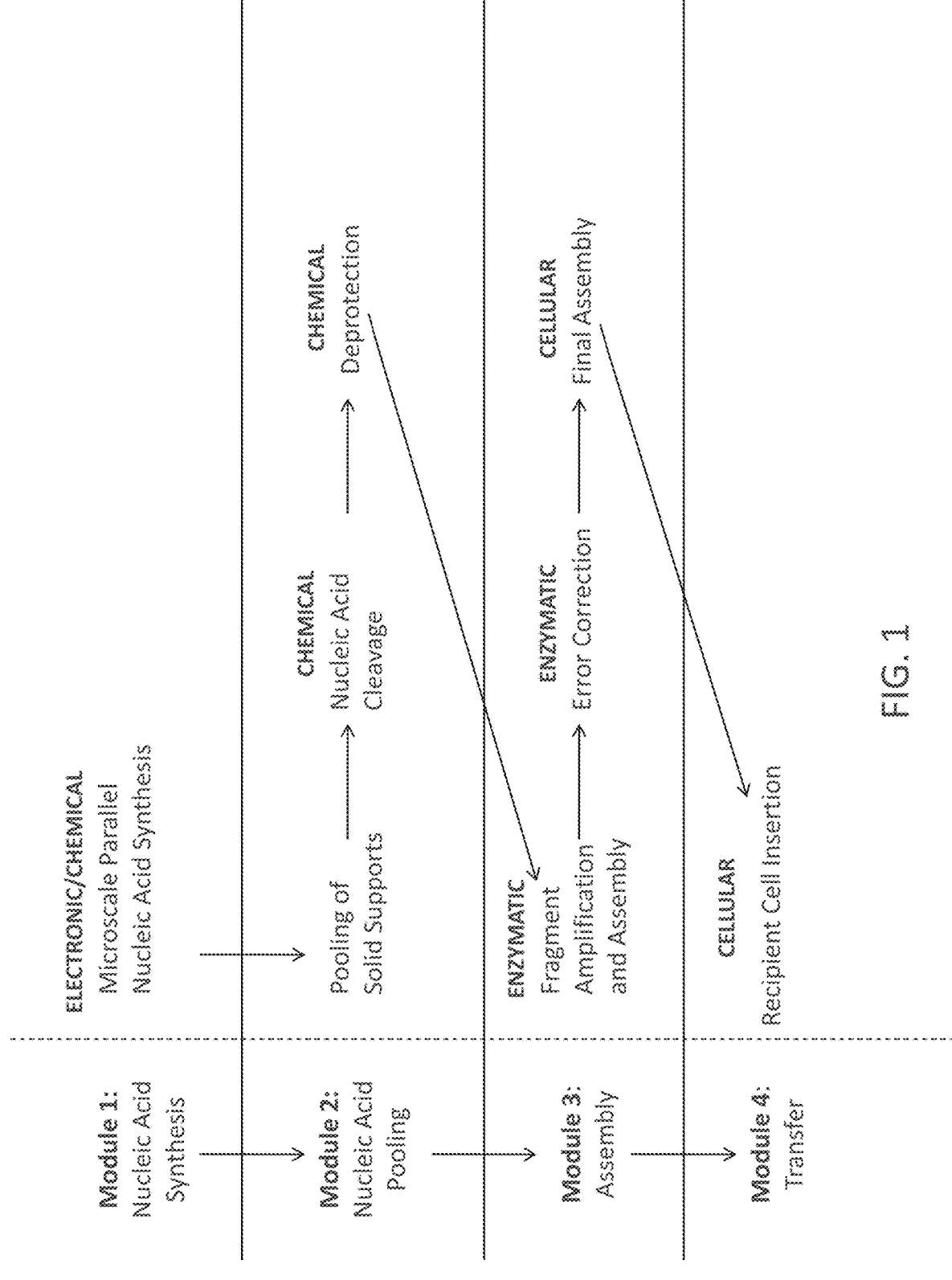
FIG. 1 is a general description of aspects of work flows of the invention. The work flow is broken into four sections, referred to as "modules" for ease of description. The work flow on the right side of the figure shows some specific step included in some aspects of methods of the invention.

Solid Support: As used herein, the term solid support refers to a porous or non-porous material on which polymers such as nucleic acid molecules can be synthesized and/or immobilized. As used herein "porous" means that the material contains pores which may be of non-uniform or uniform diameters (for example in the nm range). Porous materials include paper, synthetic filters etc. In such porous materials, the reaction may take place within the pores. The solid support can have any one of a number of shapes, such as pin, strip, plate, disk, rod, fiber, bends, cylindrical structure, planar surface, concave or convex surface or a capillary or column. The solid support can be a particle, including bead, microparticles, nanoparticles and the like. The solid support can be a non-bead type particle (e.g., a filament) of similar size. The support can have variable widths and sizes. For example, sizes of a bead (e.g., a magnetic bead) which may be used in the practice of the invention are described elsewhere herein. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers such as filter paper, chromatographic paper or the like.

In some embodiments, solid support may be fragmentable. Solid supports may be synthetic or modified naturally occurring polymers, such as nitrocellulose, carbon, cellulose acetate, polyvinyl chloride, polyacrylamide, cross linked dextran, agarose, polyacrylate, polyethylene, polypropylene, poly (4-methylbutene), polystyrene, polymethacrylate, poly (ethylene terephthalate), nylon, poly(vinyl butyrate), polyvinylidene difluoride (PVDF) membrane, glass, controlled pore glass, magnetic controlled pore glass, magnetic beads, ceramics, metals, and the like; either used by themselves or in conjunction with other materials.

In some embodiments, the support can be in a chip, array, microarray or microwell plate format. In many instances, a support generated by methods of the invention will be one where individual nucleic acid molecules are synthesized on separate or discrete areas to generate features (i.e., locations containing individual nucleic acid molecules) on the support.

In some embodiments, the size of the defined feature is chosen to allow formation of a microvolume droplet or reaction volume on the feature, each droplet or reaction volume being kept separate from each other. As described herein, features are typically, but need not be, separated by interfeature spaces to ensure that droplets or reaction volumes or between two adjacent features do not merge. Interfeatures will typically not carry any nucleic acid molecules on their surface and will correspond to inert space. In some embodiments, features and interfeatures may differ in their hydrophilicity or hydrophobicity properties. In some embodiments, features and interfeatures may comprise a modifier. In one embodiment of the invention the feature is a well or microwell or a notch.

Nucleic acid molecules may be covalently or non-covalently attached to the surface or deposited on the surface.

In one embodiment of the invention, Module 1 can involve the use of more than one solid support. In some embodiments, two or more solid supports may be arranged on a plate. Any arrangement of the solid supports could be employed such as rows or columns or a combination thereof. For example, rows can be aligned and/or the columns can be aligned. In other embodiments, rows and/or columns are equally spaced and staggered. Spacing between rows and/or between columns can be variable. The number of the solid supports comprised in, for example, a plate may be variable. In some embodiments, a plate may contain up to 1536 (or more) solid supports.

Nucleic Acid Molecule: As used herein the term "nucleic acid molecule" refers to a covalently linked sequence of nucleotides or bases (e.g., ribonucleotides for RNA and deoxyribonucleotides for DNA but also include DNA/RNA hydrids where the DNA is in separate strands or in the same strands) in which the 3' position of the pentose of one nucleotide is joined by a phosphodiester linkage to the 5' position of the pentose of the next nucleotide. Nucleic acid molecule may be single- or double-stranded or partially double-stranded. Nucleic acid molecule may appear in linear or circularized form in a supercoiled or relaxed formation with blunt or sticky ends and may contain "nicks". Nucleic acid molecule may be composed of completely complementary single strands or of partially complementary single strands forming at least one mismatch of bases. Nucleic acid molecule may further comprise two self-complementary sequences that may form a double-stranded stem region, optionally separated at one end by a loop sequence. The two regions of nucleic acid molecule which comprise the double-stranded stem region are substantially complementary to each other, resulting in self-hybridization. However, the stem can include one or more mismatches, insertions or deletions.

Nucleic acid molecules may comprise chemically, enzymatically, or metabolically modified forms of nucleic acid molecules or combinations thereof. Chemically synthesized nucleic acid molecules may refer to nucleic acids typically less than or equal to 150 nucleotides long (e.g., between 5 and 150, between 10 and 100, between 15 and 50 nucleotides in length) whereas enzymatically synthesized nucleic acid molecules may encompass smaller as well as larger nucleic acid molecules as described elsewhere in the application. Enzymatic synthesis of nucleic acid molecules may include stepwise processes using enzymes such as polymerases, ligases, exonucleases, endonucleases or the like or a combination thereof. Thus, the invention provides, in part, compositions and combined methods relating to the enzymatic assembly of chemically synthesized nucleic acid molecules.

Nucleic acid molecule also refers to short nucleic acid molecules, often referred to as, for example, primers or probes. Primers are often referred to as single-stranded starter nucleic acid molecules for enzymatic assembly reactions whereas probes may be typically used to detect at least partially complementary nucleic acid molecules. A nucleic acid molecule has a "5'-terminus" and a "3'-terminus" because nucleic acid molecule phosphodiester linkages occur between the 5' carbon and 3' carbon of the pentose ring of the substituent mononucleotides. The end of a nucleic acid molecule at which a new linkage would be to a 5' carbon is its 5' terminal nucleotide. The end of a nucleic acid molecule at which a new linkage would be to a 3' carbon is its 3' terminal nucleotide. A terminal nucleotide or base, as used herein, is the nucleotide at the end position of the 3'- or 5'-terminus. A nucleic acid molecule sequence, even if internal to a larger nucleic acid molecule (e.g., a sequence region within a nucleic acid molecule), also can be said to have 5'- and 3'-ends.

Overview:

The invention relates, in part, to compositions and methods for the preparation of nucleic acid molecules. While the invention has numerous aspects and variations associated with it, some of these aspects and variations are set out in FIG. 1 in outline form.

One advantage of the invention is that for, many applications, small amounts of synthesized nucleic acid are suitable for achieving an intended purpose (e.g., preparation of microarrays, construction of a plasmid which contains a selectable marker, etc.). In some instances, small amounts of nucleic acid are suitable for working with due to factors such as enzymatic (e.g., PCR) and intracellular amplification.

The left side of FIG. 1 shows four general "modules" representing different portions of some embodiments of the invention. Thus, in some aspects, the invention involves one or more of the following: (1) nucleic acid molecule synthesis, (2) pooling of nucleic acid molecules, (3) assembly of a plurality of nucleic acid molecules, and/or (4) transfer of assembled nucleic acids (e.g., transfer to a cell).

In relation to more specific embodiments of the invention, the right side of FIG. 1 shows some additional details related to the modules shown on the left side of the figure. Above a number of the text blocks are bolded terms such as "ENZYMATIC" and "CELLULAR". These terms indicate exemplary general means by which the process referred to can be performed. As one skilled in the art would understand, some processes can be performed, for example, either chemically, enzymatically, or in a cell.

Module 1, as shown in FIG. 1 refers to a single process termed "Microscale Parallel Nucleic Acid Molecule Synthesis". As set out elsewhere herein, this process will typically involve several steps which will vary with how the process is performed. In many embodiments, the general function of Module 1 will be the generation of a plurality of nucleic acid molecules. These nucleic acid molecules may be designed as a group to be joined to form one or more larger nucleic acid molecule or when contacted with additional nucleic acid molecules (e.g., "stitching" nucleic acid molecules).

Module 2, as shown in FIG. 1 refers to processes termed "Pooling of Solid Supports", "Nucleic Acid Molecule Cleavage", and "Deprotection". The general function of Module 2 will be the preparation of nucleic acid molecules for participation in one or more process referred to in Module 3. This will often mean combining nucleic acid molecules which differ in sequence and the removal of any chemical groups which are either not necessary or not desirable for the performance of one or more processes referred to in Module 3.

Using Module 2 as an example, as one skilled in the art would recognize, FIG. 1 shows general embodiments of the invention. More specifically, Module 2 refers to the pooling of solid supports. These supports will typically contain nucleic acid molecules. In some embodiments, nucleic acid molecules may be obtained in a form free of solid supports, then pooled.

Module 3, as shown in FIG. 1 refers to the processes termed "Fragment Amplification and Assembly", "Error Correction", and "Final Assembly". The general function of Module 3 processes is the generation of assembled nucleic acid molecules with high sequence fidelity, with comparison to the sequence of nucleic acid molecules which were sought to be produced.

Module 4, as shown in FIG. 1 refers to the processes of termed "Recipient Cell Insertion". As one skilled in the art would understand, introduction of nucleic acid molecules generated by methods of the invention into cells is only one application. In most instances, a nucleic acid molecule assembled according to methods of the invention will be designed for a specific application. Applications vary widely and include biofuel production, bioremediation, and chemical precursor production.

In some embodiments, amino group containing support matrix having a polyvinyl backbone may be used as solid support. For example, monodispersed particles obtained by methods as described in U.S. Pat. No. 6,335,438 the disclosure of which is incorporated herein by reference, may be used in the practice of the invention.
Module 1

In the invention, the nucleic acid molecules may be attached to solid supports, such as particles or beads (e.g., controlled pore glass beads). In one embodiment, magnetic microbeads are used as solid supports. In many instances, single-activated porous 1 μm size microbeads with large surface to volume ratios may be used in the current invention. The uniform nature of such monodispersed particles generally provides for uniform reaction rates particularly suited to synthesis in automated chemical synthesizers (e.g., nucleic acid molecule synthesizers). Beads may initially be provided with a reactive group. For example, in some embodiments of the invention, DYNABEADS® M-280 (Dynal Biotech ASA, Oslo, Norway) may be used. DYNABEADS® M-280 are 2.8 μm beads which come in a number of forms. M-280 beads tend are fairly uniform, superparamagnetic, polystyrene beads coated with a polyurethane layer. These beads may be obtained with various chemical activation groups suitable for use for different applications.

Magnetic bead technology is described in U.S. Pat. No. 5,512,439, which is incorporated herein by reference.

Synthesis substrates other than those composed of CPG or magnetic materials may also be used with the invention and include those composed of polystyrene (e.g., polystyrene-1% divinylbenzene, macroporous polystyrene, and poly (ethylene glycol)-polystyrene (PEG-PS)), polyamide (e.g., polyamide bonded silica gel), silica gel, and cellulose. Some of these substrates are available in resin form. In many instances, substrates that are resins may be placed in wells, instead of or in conjunction with beads, and may be used for nucleic acid synthesis.

Other nucleic acid ligation methods, and arrays which employ them, are know in the art. For example, methods are known which use an amine or a peroxide (which opens to an ether bridge) activated surface. As noted elsewhere herein, for EGA methods in the art, a hydroxyl group has been described and used to link nucleic acid to a silica magnetic bead surface. The invention includes such linking methods and compositions which contain them.

In some instances, it may also be desired to use a semi-solid support that may have a gel-like or viscous consistence or matrix instead of a solid support. The invention contemplates this and in suitable instances here where a solid support is referred to a non-solid support may be used.

Factors which determine the amount of nucleic acid which can be synthesized include surface area and size of particles upon which synthesis occurs. Thus, to some extent, support (e.g., bead) parameters can be adjusted to alter the amount of nucleic acid synthesized. Beads which may be used in the practice of the invention may vary widely in terms of size, including the following size ranges: from about 0.01 μm to about 1,000 μm, from about 0.1 μm to about 1,000 μm, from about 1.0 μm to about 1,000 μm, from about 0.01 μm to about 400 μm, from about 0.01 μm to about 200 μm, from about 0.01 μm to about 100 μm, from about 0.1 μm to about 100 μm, from about 0.1 μm to about 50 μm, from about 1.0 μm to about 600 μm, from about 1.0 μm to about 400 μm, from about 1.0 μm to about 200 μm, from about 1.0 μm to about 100 μm, from about 2.0 μm to about 400 μm, from about 2.0 μm to about 200 μm, from about 5.0 μm to about 500 μm, etc. in average diameter.

Further, beads may be used which allow for an average amount of nucleic acid to be produced in the following amounts: from about 0.001 nanomoles to about 1,000 nanomoles, from about 0.1 nanomoles to about 1,000 nanomoles, from about 1.0 nanomole to about 1,000 nanomoles, from about 5.0 nanomoles to about 1,000 nanomoles, from about 10 nanomoles to about 1,000 nanomoles, from about 30 nanomoles to about 1,000 nanomoles, from about 50 nanomoles to about 1,000 nanomoles, from about 200 nanomoles to about 1,000 nanomoles, from about 1.0 nanomole to about 500 nanomoles, from about 1.0 nanomole to about 250 nanomoles, from about 10 nanomoles to about 500 nanomoles, etc.

TABLE 1

| Number of Nucleic Acid Molecules | Nucleic Acid (Nanomoles) |
| --- | --- |
| $1.26 \times 10^5$ | $2.09 \times 10^{-10}$ |
| $3.14 \times 10^6$ | $5.22 \times 10^{-09}$ |
| $1.26 \times 10^7$ | $2.09 \times 10^{-08}$ |
| $1.13 \times 10^8$ | $1.88 \times 10^{-07}$ |
| $3.14 \times 10^8$ | $5.22 \times 10^{-07}$ |
| $1.26 \times 10^9$ | $2.09 \times 10^{-06}$ |

In many instances, the yield of nucleic acid molecules chemically synthesized decreases once a certain size has been reached. In many embodiments of the invention, chemically synthesized nucleic acid molecules will be in the range of from about 8 to about 100 nucleotides, from about 8 to about 35 nucleotides, from about 8 to about 40 nucleotides, from about 8 to about 50 nucleotides, from about 8 to about 100 nucleotides, from about 15 to about 100 nucleotides, from about 15 to about 75 nucleotides, from about 15 to about 50 nucleotides, from about 20 to about 60 nucleotides, from about 40 to about 400 nucleotides, from about 40 to about 300 nucleotides, from about 40 to about 200 nucleotides, from about 40 to about 100 nucleotides, from about 40 to about 90 nucleotides, from about 50 to about 400 nucleotides, from about 50 to about 300 nucleotides, from about 50 to about 200 nucleotides, from about 50 to about 100 nucleotides, from about 50 to about 90 nucleotides, from about 50 to about 80 nucleotides, from about 75 to about 400 nucleotides, from about 75 to about 300 nucleotides, or from about 75 to about 200 nucleotides.

As one skilled in the art would recognize, the amount of nucleic acid required to be produced will vary with, for examples, the application and the efficiency of assembly methods used. When a replicable molecule (e.g., via PCR, insertion into a cell, etc.) is generated, theoretically only one assembled nucleic acid molecule need be generated. If the number of nucleic acid molecules generated are reduced to the point where theoretically only one fully assembled nucleic acid molecule is generated, then half the time no fully assembled nucleic acid molecule will generated. Thus, one lower limit for the amount of nucleic acid to be produced using methods of the invention is based upon the number of fully assembled nucleic acid molecules which may be generated. This number will often vary with the number of synthetic nucleic acid molecules that must be combined to form the final construct. Methods of the invention will typically be designed to generate from about 1 to about 500,000, from about 10 to about 500,000, from about 100 to about 500,000, from about 500 to about 500,000, from about 1 to about 1,000, from about 1 to about 500, from about 10 to about 1,000, from about 10 to about 500, from about 100 to about 1,000, from about 100 to about 500, from about 100 to about 5,000, from about 100 to about 50,000, from about 100 to about 250,000, from about 1,000 to about 50,000, etc. assembled nucleic acid molecules.

As one skilled in the art would understand, nucleic acid synthesis substrate area directly reflects the number of nucleic acid molecules which may be synthesized on that substrate. TABLE 2 below shows bead size, surface area calculations and an estimated number of nucleic acid molecules that may be generated on the specified beads.

TABLE 2

| Bead Diam. (μm) | Surface Area (μm$^2$) | No. of Molecules |
|---|---|---|
| 1 | 314.2 | $1.26 \times 10^5$ |
| 5 | 7,855 | $3.14 \times 10^6$ |
| 10 | 31,416 | $1.26 \times 10^7$ |
| 30 | 282,743 | $1.13 \times 10^8$ |
| 50 | 785,398 | $3.14 \times 10^8$ |
| 100 | 3,141,593 | $1.26 \times 10^9$ |

Note:
The effective surface area for the beads used to generate the above data is estimated to be 100 times higher than the spherical surface are.

In some embodiments, oligonucleotide synthesis will be performed using 2.8 μm beads in a plate with one bead per well. Further, the wells may be designed as cylindrical holes or chambers that are 4 μm and 3 μm deep. When well spacing of 100 μm is used, a 10 mm$^2$ chip can accommodate 10,000 wells. In many instances when plates are made by etching, the wells will be of a non-cylindrical shapes and may be pyramid, cone or quadratic shaped. In some instances, the wells may be in the shape of a reverse, truncated cone.

The number of individual nucleic acid molecules generated will also vary with the application. While costs savings can be achieved by reagent usage reductions, it will generally be desirable to generate enough nucleic acid molecules need for, for example, efficient assembly. Further, the number of nucleic acid molecules having a particular nucleotide sequence produced with generally reflects the "carrying capacity" of the synthesis substrate. For example, a 30 micron bead typically can be used to generate about 1,000, 000 nucleic acid molecules. For example, in many instances, as bead size, decreases, so will the number of nucleic acid molecules that may be produced on each bead.

Methods of the invention may be used to generate from about 100 to about 20,000,000, from about 1,000 to about 20,000,000, from about 10,000 to about 20,000,000, from about 100 to about 5,000,000, from about 1,000 to about 5,000,000, from about 10,000 to about 5,000,000, from about 100 to about 1,000,000, from about 1,000 to about 1,000,000, from about 10,000 to about 10,000,000, from about 100 to about 500,000, from about 1,000 to about 500,000, from about 10,000 to about 500,000, etc. nucleic acid molecules designed to have the same nucleotide sequence.

The number of nucleic acid molecule synthesis sites (e.g., wells) can vary greatly and will be determined by a number of factors including (1) the limitations of engineering and nucleic acid molecule synthesis hardware and (2) the amount of nucleic acid which is desired (see elsewhere herein for a discussion of this factor). As examples, the number of nucleic acid molecule synthesis sites (e.g., wells) in synthesis platforms used in the practice of the invention may vary in total number between 9 and 200,000, between 9 and 100,000, between 9 and 20,000, between 9 and 1,000, between 9 and 500, between 1,000 and 200,000, between 1,000 and 400,000, between 1,000 and 500,000, between 1,000 and 1,00,000, between 1,000 and 10,000,000, between 20,000 and 1,000,000, between 50,000 and 10,000,000, between 10,000 and 5,000,000, between 1,000 and 100,000, between 2,000 and 100,000, between 5,000 and 100,000, between 10,000 and 100,000, between 20,000 and 100,000, between 30,000 and 100,000, between 1,000 and 80,000, between 1,000 and 70,000, between 1,000 and 50,000, between 1,000 and 40,000, between 1,000 and 30,000, between 1,000 and 20,000, between 1,000 and 10,000, between 1,000 and 8,000, between 1,000 and 5,000, between 5,000 and 50,000, between 10,000 and 50,000, between 5,000 and 35,000, etc. In addition, the number of nucleic acid molecule synthesis sites (e.g., wells) may vary between 1,000 and 5,000, between 1,000 and 10,000, between 1,000 and 20,000, between 1,000 and 30,000, between 2,000 and 5,000, between 2,000 and 10,000, between 4,000 and 15,000, between 100 and 1,000, between 100 and 3,000, between 100 and 5,000, between 250 and 5,000, etc. per mm$^2$.

The amount of reagent space per nucleic acid molecule synthesis site (e.g., well) will vary with the size and shape of the well and, in particular, the area of the space capable of accepting reagents. This will vary with factors such as whether the nucleic acid molecule synthesis site is a flat surface (e.g., relying on surface tension to keep reagents localized over the synthesis site or a cavity (e.g., a well). Also, the amount of reagent applied may be determined by the amount of reagent necessary to cover the synthesis site, deliver the necessary amount of reactant(s), and/or dilute, remove, or wash away reagents present at the synthesis site. The amount of reagent applied (when the reagent is a liquid) and the amount of reagent space at the synthesis site may vary greatly including between $0.001 \times 10^{-15}$ l (femtoliter) and 100 μl, between $0.01 \times 10^{-15}$ l (femtoliter) and 100 μl, between $0.1 \times 10^{-15}$ l (femtoliter) and 100 μl, between $1.0 \times 10^{-15}$ l (femtoliter) and 100 μl, between $0.1 \times 10^{-15}$ l (femtoliter) and 1 μl, between $0.1 \times 10^{-15}$ l (femtoliter) and 500 nl, between $0.1 \times 10^{-15}$ l (femtoliter) and 100 nl, between $0.1 \times 10^{-15}$ l (femtoliter) and 1 nl, between $0.1 \times 10^{-15}$ l (femtoliter) and 500 μl (picoliter), between $0.1 \times 10^{-15}$ l (femtoliter) and 100 μl, between $0.1 \times 10^{-15}$ l (femtoliter) and 10 μl, between $0.1 \times 10^{-15}$ l (femtoliter) and 1 μl, between $0.001 \times 10^{-15}$ l (femtoliter) and 1 μl, between $0.001 \times 10^{-15}$ l (femtoliter) and $1.0 \times 10^{-15}$ l (femtoliter), between $0.001 \times 10^{-15}$ l (femtoliter) and $100 \times 10^{-15}$ l (femtoliter), between $1.0 \times 10^{-15}$ l (femtoliter) and $500 \times 10^{-15}$ l (femtoliter), etc.

To make the solid support material suitable for nucleic acid molecule synthesis, non-nucleosidic linkers or nucleoside succinates may be covalently attached to reactive amino groups. If necessary, however, other surface functions such as carboxyl could be used to attach a linker carrying a hydroxyl group or alternatively a 3'-attached nucleotide.

The linker, when present, may be a chemical entity that attaches the 3'-O of the nucleic acid molecule to the solid support (e.g., a functional group on a solid support). In most cases, the linker will be stable to all the reagents used during nucleic acid molecule synthesis, but cleavable under specific conditions at the end of the synthesis process. One linker commonly used in nucleic acid molecule synthesis is the succinyl linker. Different linkers with different properties are known to those skilled in the art and can be selected by the skilled person depending on the downstream process requirements.

Nucleosidic solid supports (e.g., support prederivatized with base) are widely used in nucleic acid molecule synthesis. One example of such a support is one where the 3'-hydroxy group of the 3'-terminal nucleoside residue is attached to the solid support via a 3'-O-succinyl arm. The use of nucleosidic solid supports requires usage of different types of beads (one for each base). However, the fact that a nucleosidic solid support has to be selected in a sequence-specific manner (according to the first base required for each nucleic acid molecule) reduces the throughput of the entire synthesis process due to laborious pre-selection and distri-bution of beads attached to a specific starter base to indi-vidual microwells.

A more convenient method for synthesis starts with a universal support where a non-nucleosidic linker is attached to the solid support material. An advantage of this approach is that the same solid support may be used irrespectively of the sequence of the nucleic acid molecule to be synthesized. One example of a universal support that can be used in the current invention is described in U.S. Pat. No. 7,202,264, the disclosure of which is incorporated herein by reference. However, other universal linkers known by the skilled in the art may be equally appropriate to carry out the invention. For the complete removal of the linker and the 3'-terminal phosphate from the assembled nucleic acid molecule, some of the universal solid supports known in the art require gaseous ammonia, aqueous ammonium hydroxide, aqueous methylamine or a mixture thereof.

A number of methods for synthesizing nucleic acid are known. Many of these methods follow a series of basic steps, such as, for example, the following, with appropriate washing steps using, for example, acetonitrile, ethylacetate or other washing reagents suitable for practicing the inven-tion:

a) the first nucleotide, which has been protected at the 5' position, is derivatized to a solid support, usually controlled pore glass (CPG), or is obtained prederiva-tized;

b) the sugar group of the first nucleotide is deprotected (e.g., via detritlyation) (a process often referred to as "Deprotection"), using, for example, tricholoracetic acid in methylene chloride, which results in a colored product which may be monitored for reaction progress;

c) the second nucleotide, which has the phosphorus, sugar and base groups protected, is added to the growing chain, usually in the presence of a catalyst, such as, for example, tetrazole or 4,5-dicyanoimidazole (a process often referred to as "Coupling");

d) unreacted first nucleotide is capped to avoid accumu-lation of deletions, using, for example, acetic anhydride and N-methylimidazole (a process often referred to as "Capping");

e) the phosphite triester is oxidized to form the more stable phosphate triester, usually using, for example, iodine reagents (a process often referred to as "Oxidiz-ing");

f) the process is repeated as needed depending on the desired length of the nucleic acid molecule; and g) cleavage from the solid support is done, usually using aqueous or gaseous ammonia at elevated temperatures. The skilled in the art will recognize that in certain embodiments of the invention the order of steps may vary or some of the steps including the washing steps may be repeated as appropriate according to the used protocol.

In the current invention, the state of the art phosphora-midite synthesis chemistry is further improved by modifi-cation of specific steps of the above protocol. In one embodiment organocatalysts can be used to improve, for example, the efficiency of the coupling step. Organocatalysts and some uses of such catalysts are set out in Avenier and Hollfelder, *Combining Medium Effects and Cofactor Cataly-sis: Metal-Coordinated Synzymes Accelerate Phosphate Transfer by* $10^8$ *Chem. Eur. J.* 15:12371-12380 (2009) and Jordan et al., *Asymmetric phosphorylation through catalytic P(III) phosphoramidite transfer: Enantioselective synthesis of D-myo-inositol-6-phosphate, Proc. Nat. Acad. Sci. USA,* 107: 20620-20624 (2010).

In some embodiments, the invention makes use of local-ized chemical reactions through the production of electro-chemically generated acid (EGA). As an example, address-able electrical signals may be used for the production of acid at sufficient concentration to allow deprotection of the dimethoxytrityl (DMT) protecting group from surface. (Maurer et al., *"Electrochemically Generated Acid and Its Containment to* 100 *Micron Reaction Areas for the Produc-tion of DNA Microarrays" PLoS,* Issue 1, e34 (December 2006).)

One issue with the production of EGA as part of a nucleic acid molecule synthesis protocol on a surface (e.g., a micro-surface) is "splash over" to adjoining regions. "Splash over", which includes diffusion, can result in reactions occurring in unintended location (e.g., caused by diffusion of EGA). While such effects may be fairly minor when one reaction occurs, when multiple reactions occur in succession splash over effects multiple reaction cycles may result in numerous misincorporated bases. This issue can be addressed in sev-eral ways. One way is to overlay the reaction areas with a buffer (e.g., a buffer containing an organic base) which sufficiently neutralizes the acid if it moves from the local environment. Another way is through physical containment or compartmentalization. For example, if the EGA is gen-erated in a well and catalyzes a reaction in that well, the well may be of sufficient size to prevent the acid from exiting. Containment within the well is thus a factor of the size of the well and the amount of acid generated. In some reaction formats, some acid will invariably exit the well. This should pose no problems unless a quantity sufficient to catalyze a reaction reaches another well in which that reaction is not supposed to occur. As noted above, the use of an overlaying buffer can be used to minimize such reactions.

Another issue with EGA is depurination of oligonucle-otides. It has been found that the contacting of oligonucle-otides with EGA at lower pHs (e.g., a pH of 1.5 vs. a pH of 2.2) results in significant oligonucleotide depurination (data not shown). The invention includes methods in which the amount of EGA used results in a pH sufficient to deprotect oligonucleotides while minimizing depurination. In particu-lar, deprotection may occur at pHs from about 1.6 to about 2.8, from about 1.8 to about 2.8, from about 2.0 to about 2.8, from about 1.8 to about 2.6, from about 1.8 to about 2.4, from about 1.9 to about 2.5, from about 2.0 to about 2.4, etc.

The concentration of the EGA and other incubation conditions (e.g., time, temperature, etc.) may be adjusted such that a desired level of deprotection occurs, while minimizing depurination. Thus, from a "functional" perspective, EGA mediated oligonucleotide deprotection conditions may be adjusted such that the ratio of deprotection and depurination is within a desirable range. In some instances, the EGA mediated deprotection conditions may be adjusted such that at least 95% (e.g., from about 95.1% to about 100%, from about 95.5% to about 100%, from about 96% to about 100%, from about 97% to about 100%, from about 98% to about 100%, from about 99% to about 100%, from about 99.5% to about 100%, from about 95.1% to about 99.8%, from about 95.5% to about 99.8%, from about 97% to about 99.8%, from about 98% to about 99.8%, from about 98.5% to about 99.8%, from about 99% to about 99.8%, from about 99.5% to about 99.8%, from about 97% to about 99.5%, from about 98% to about 99.5%, etc.) of oligonucleotides contacted are deprotected. In some instances, the EGA mediated deprotection conditions may be adjusted such that less than 10% (e.g., less than about 9%, less than about 8%, less than about 7%, less than about 6%, less than about 5%, less than about 4%, less than about 3%, less than about 2%, less than about 1.5%, less than about 1%, less than about 0.7%, less than about 0.5%, less than about 0.4%, less than about 0.3%, less than about 0.2%, less than about 0.1%, less than about 0.07%, less than about 0.05%, less than about 0.03%, less than about 0.02%, less than about 0.01%, etc.) of purines (adenosine and guanosine) present in oligonucleotides are depurinated. In some instances, the ratio of deprotection and depurination may be from about 99.9% to about 0.01%, from about 99.5% to about 0.05%, from about 99.5% to about 0.1%, from about 99.9% to about 0.05%, from about 99% to about 0.1%, from about 98% to about 0.5%, from about 97% to about 0.01%, from about 97% to about 0.5%, from about 97% to about 1%, from about 99% to about 1%, from about 98% to about 0.01%, from about 98% to about 0.1%, etc.

As discussed elsewhere herein, both failure to deprotect and depurination of oligonucleotides during synthesis can result in nucleic acid synthesis errors. While many errors can be corrected, the goal of achieving low error rates in final product nucleic acid molecules is often best achieved by low error introduction, in combination with high efficiency error correction.

Exemplary error types include mis-incorporation, skipped base/"deletion" (e.g., due to failure to deprotect), additional base/"insertion" (e.g., due to an omitted or inappropriately removed protecting group), and post-base additional alterations (e.g., depurination). It will generally be desirable to adjust oligonucleotide synthesis conditions such that each of these error types is kept as low as technically possible.

Plates which may be used in the practice of the present invention include modified forms of plates described in U.S. Patent Publication No. 2010/0137143 A1, the disclosure of which is incorporated herein by reference, shows such a representative plate format.

Figure 2A:
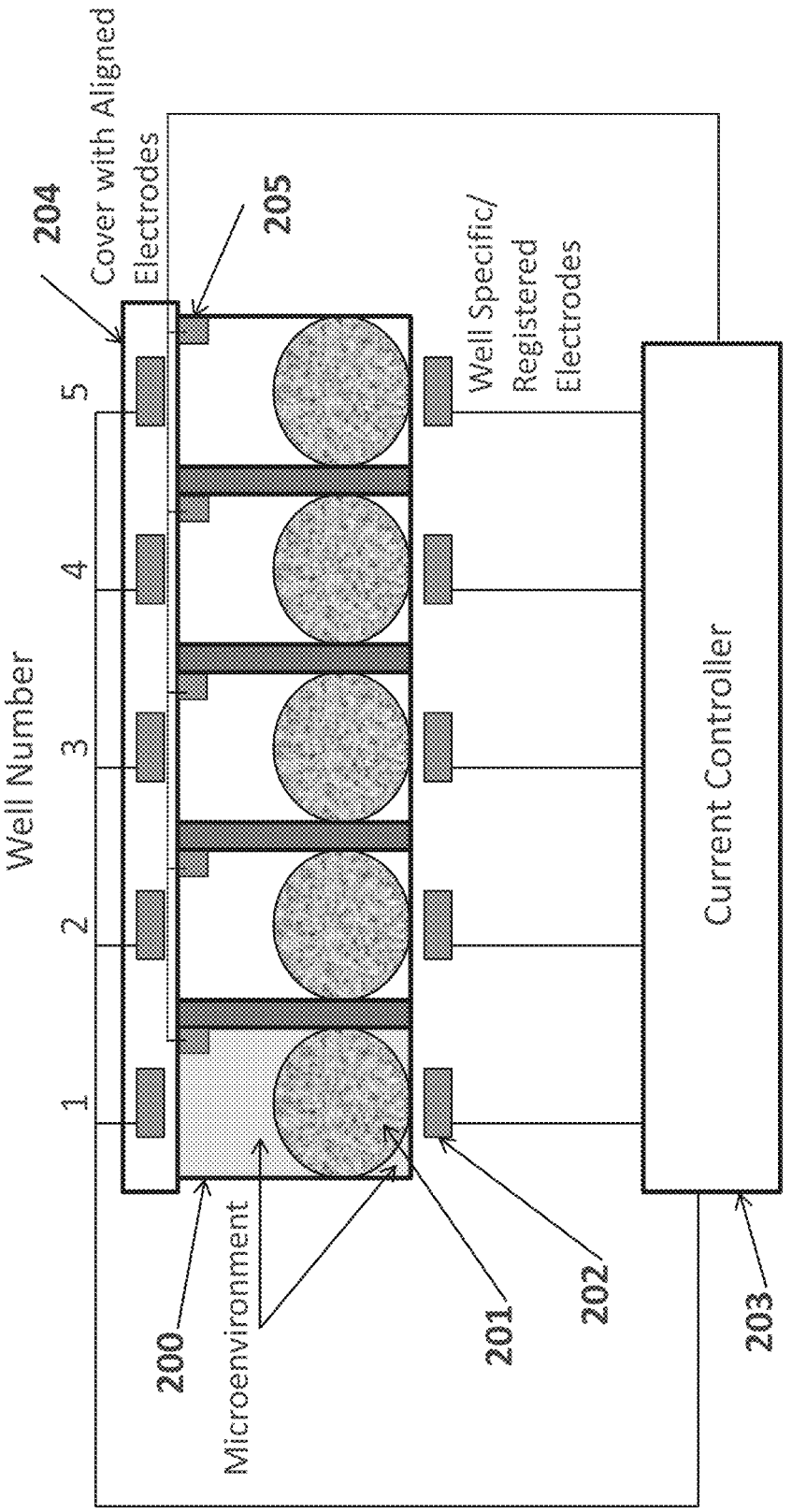
FIGS. 2A-2B are schematic representations of a row of wells according to an embodiment of the invention. The darker area in well 1 indicates the presence of a reagent (e.g., EGA) not present at a given time in the other wells.
Figure 2B:
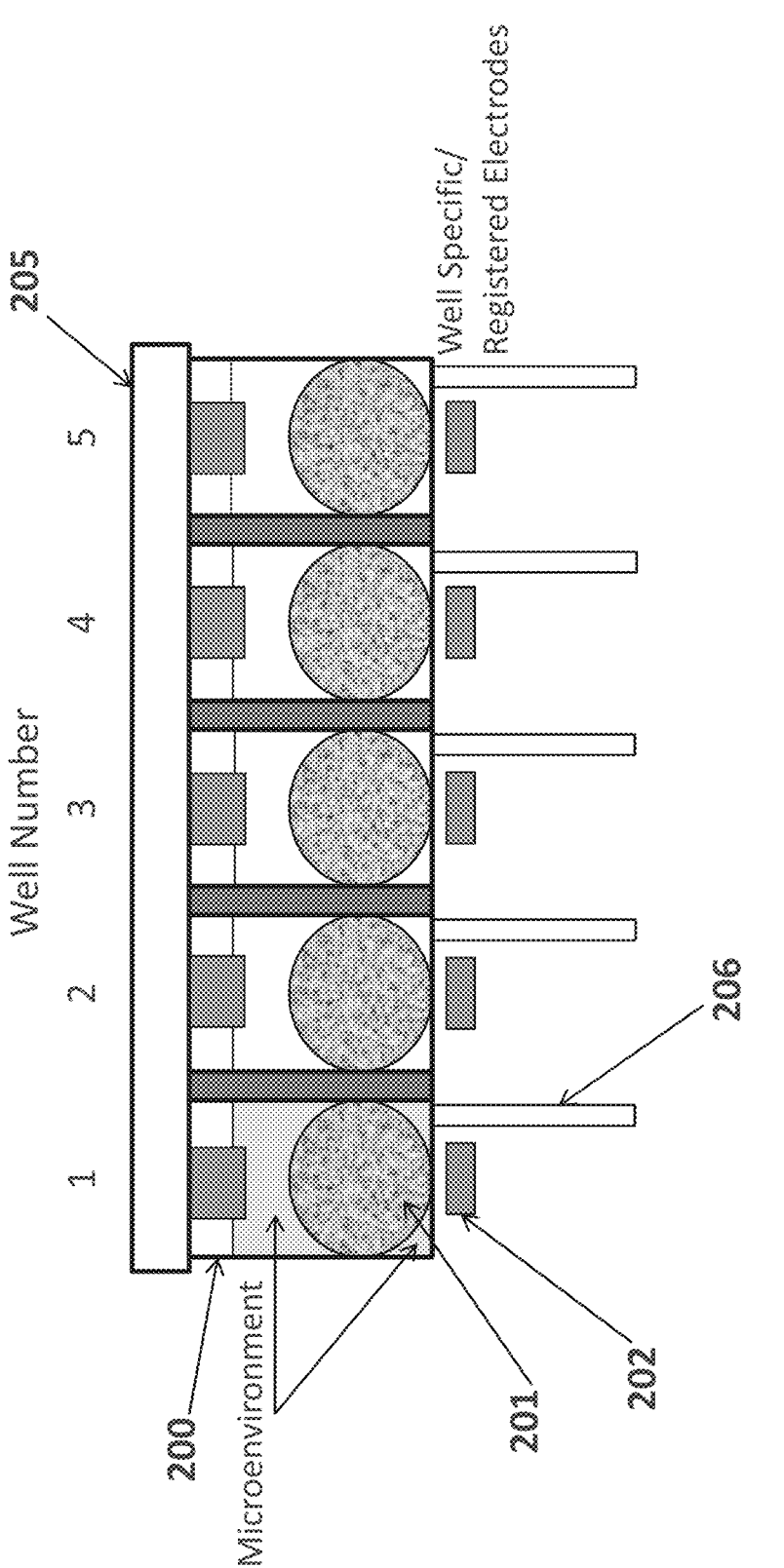

FIGS. 2A-2B are schematic representations of a row of wells 200 according to an embodiment of the invention. The embodiment of FIGS. 2A-2B illustrate five wells each containing a magnetic bead 201 at the bottom. Beneath each well is an electrode 202 which can deliver current to the well that it is associated with. Each electrode is communicates with a current controller 203 which regulates current to the electrode. The magnetic bead may contain a linker associated with an initial building block. As an example, the bead may contain first nucleotide (with an A, T, C, G or U base, or a modified base, depending on the first base desired in the nucleic acid molecule to be synthesized). The first base may be added as part of the synthesis process (e.g., with the bead having a protected hydroxyl group) or may be prederivatized prior to insertion into the well. In either event, in most cases, a protective group will be present (e.g., at the 5' position) which must be removed before another base may be covalently connected as part of a nucleic acid molecule chain.

Microfluidic channels (not shown in FIG. 2A) may be included for efficiently addition and removal of reagents from the wells. Thus, the invention includes, in part, a microfluidic plate designed to interface with a microfluidic system for adding and removing fluids from wells of the plate. Microfluidic channels used in similar plates are described in U.S. Patent Publication No. 2010/0137143 A1, the disclosure of which is incorporated herein by reference for background information.

The cover of the plate 204 shown in FIG. 2A contains aligned electrodes which are connected to the current controller. A larger electrode (e.g., an electrode which extends over the tops of all of the wells) may be included in the cover to "close the circuit". Thus, the cover may contain one electrode aligned with each well for which an electrochemical reaction is sought to be, one electrode in operable connection with all wells of the plate, or multiple electrodes some or all of which are in operable connection with two or more wells. In an alternative embodiment, the cover electrode for each well is replaced with one or more electrodes embedded or positioned along one or more sidewall of each well. Thus, it is not critical that electrodes be positioned in the cover. In fact, in many instances, it will be desirable (e.g., ease of manufacturing) to place the electrodes in a place other than the cover.

Reference electrodes (RE) 205 may also be included to provide a stable and pre-defined electric potential. To apply a specific potential on a working electrode (WE), the potential of the WE against the potential of the RE may be measured. Next the potential between counter electrode (CE) and WE may be adjusted until the potential between RE and CE has the correct value.

One method for deprotection may employ the oxidization of hydroquinone to benzoquinone (redox system) on the WE in order to produce protons. To set a specific pH in a well, a constant current may be applied for a specified period of time. In instances of a less active WE, a strong increase of the WE potential will occur. This can lead to unintended reactions (e.g., oxidation of the solvent or damage of WE material at high potential). To avoid this effect, the potential of the WE may be controlled.

Figure 15:
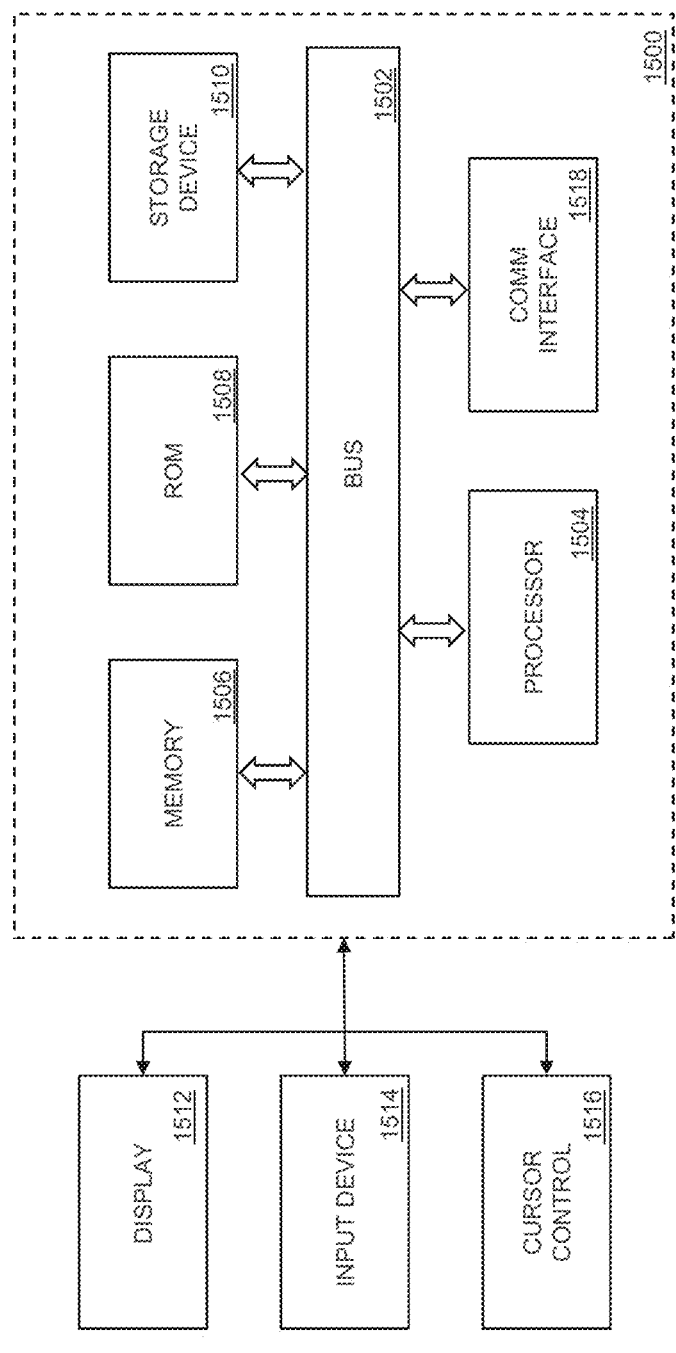
FIG. 15 is a block diagram that illustrates a computing system, upon which embodiments of the present teachings may be implemented.

The current controller (interchangeably, controller) may be a microprocessor or processor, such as shown in FIG. 15, for example The controller (not shown) may comprise a conventional current control system, including, for example, a microprocessor circuit in communication with a memory circuit. The memory circuit may include instructions for directing the microprocessor circuit to energize one or more of the electrodes (e.g., energize electrodes associated with well 1 or a plurality of wells). Optionally, the memory circuit may include instructions for activating one of a pair of electrodes (e.g., activate the bottom electrode associated with well 1). In still another embodiment, the memory circuit may include instructions for gradually increasing/decreasing bias to the electrodes so as to reduce possibility of a sudden surge at the well.

In another embodiment, the current controller communicates with external processor circuit(s) such as a potentiostat circuit, input/output ("I/O") devices and displays. The circuit or circuit board enables the control of the device and may also be used to communicate with other devices (such as PC, iPad, etc.).

In a variation of the embodiment of FIG. 2A, both electrodes (the anode and the cathode) may be placed at the bottom of the well. This allows for electrical current to be generated near the bottom of the well, thereby generating a localized EGA in the area closely adjacent the bead. Depending on the method by which reagents are added to and/or removed from the wells and other factors, such configuration can be used to limit cross-talk between the wells, interference or unintended EGA contamination.

A related embodiment is shown in FIG. 2B. Here the cover contains aligned electrodes 205 which extend into the reagent portion of the well. Drainage tubes 206 are positioned at the bottom of each well. These drainage tubes serve several functions. One function is removing reagents at the completion of a chemical reaction step (e.g., base addition, washing, deprotection, etc.). Another function is lowering the fluid level for the deprotection step. In other words, fluid may be added to all of the wells, then the fluid level may be lowered through drainage tubes before biasing the wells. Lowering the well's fluid level reduces cross-spillage between wells and increases synthesis fidelity. The lowered fluid level also decreases potential cross-talk and contamination between adjacent wells. The same is true of general fluid removal through the bottle of the well. This is so because cross-well contamination with EGA can result in incorrect base incorporation. Even EGA generated base mis-incorporation occurs in 0.5% of nucleic acid molecules being synthesized in adjoining wells, the net result could be roughly a doubling of base mis-incorporation. Thus, drawing down the fluid level in the wells and bottom of the well drainage results in increase synthesis fidelity.

One means for removing fluid from wells from the top of the wells. This can be done by any number of means including the use of pipette tips or the introduction of an absorbent material. In either instance, the goal would be to remove enough fluid from each well to minimize "splash over". In some instance, the only wells that fluid levels will be reduced in will be ones which undergo a reaction (e.g., the generation of EGA, resulting in deprotection). In other words, fluid level reduction can be performed only in wells where one or more reactants are generated.

The construction of the wells can be accomplished by conventional manufacturing methods, including, for example, CMOS and VLSI techniques. The wells can be formed in semiconductor or polymeric substrates. In an exemplary embodiment, the wells are configured in a semiconductor substrate using conventional etching and boring techniques. The insider surface of the wells may be coated with insulating material to reduce cross talk between adjacent wells. In corollary embodiment, well surfaces may be coated to increase conductivity thereby generating EGA more uniformly. Well surfaces may be coated with different layers to reduce cross-talk while increasing electro- or thermal-conductivity inside the well. Thus, the walls may comprise a composite of different material which while reducing cross-talk between the wells, would increase conductivity within each well for rapid EGA generation.

The top surface of the wells (the span between adjacent wells) may also be coated to provide reagent repellent surfaces. By way of example, the top surfaces may be coated with hydrophobic compositions to repel cross-contamination. Methods for reducing well to well cross-contamination are set out in U.S. Pat. No. 6,444,111, the disclosure of which is incorporated herein by reference.

Finally, the shape of the wells may be configured to reduce cross-contamination while increasing reaction speed. For example, the wells may be configured to have cylindrical, barrel or conical shapes.

In many methods using, for example, the plate configuration of FIGS. 2A-2B, the sugar group of the first nucleotide is deprotected by activating (energizing) a chemical reaction initiated by an electrical signal (or a pulse). As noted elsewhere herein, one method for doing this is through the generation of an electrochemically generated acid (EGA). In many cases, it will be desirable to control the amount of chemical reactant made (e.g., EGA) so as to efficiently catalyze the deprotection reaction while limiting the possibility of reactant from cross-contamination.

Figure 17:
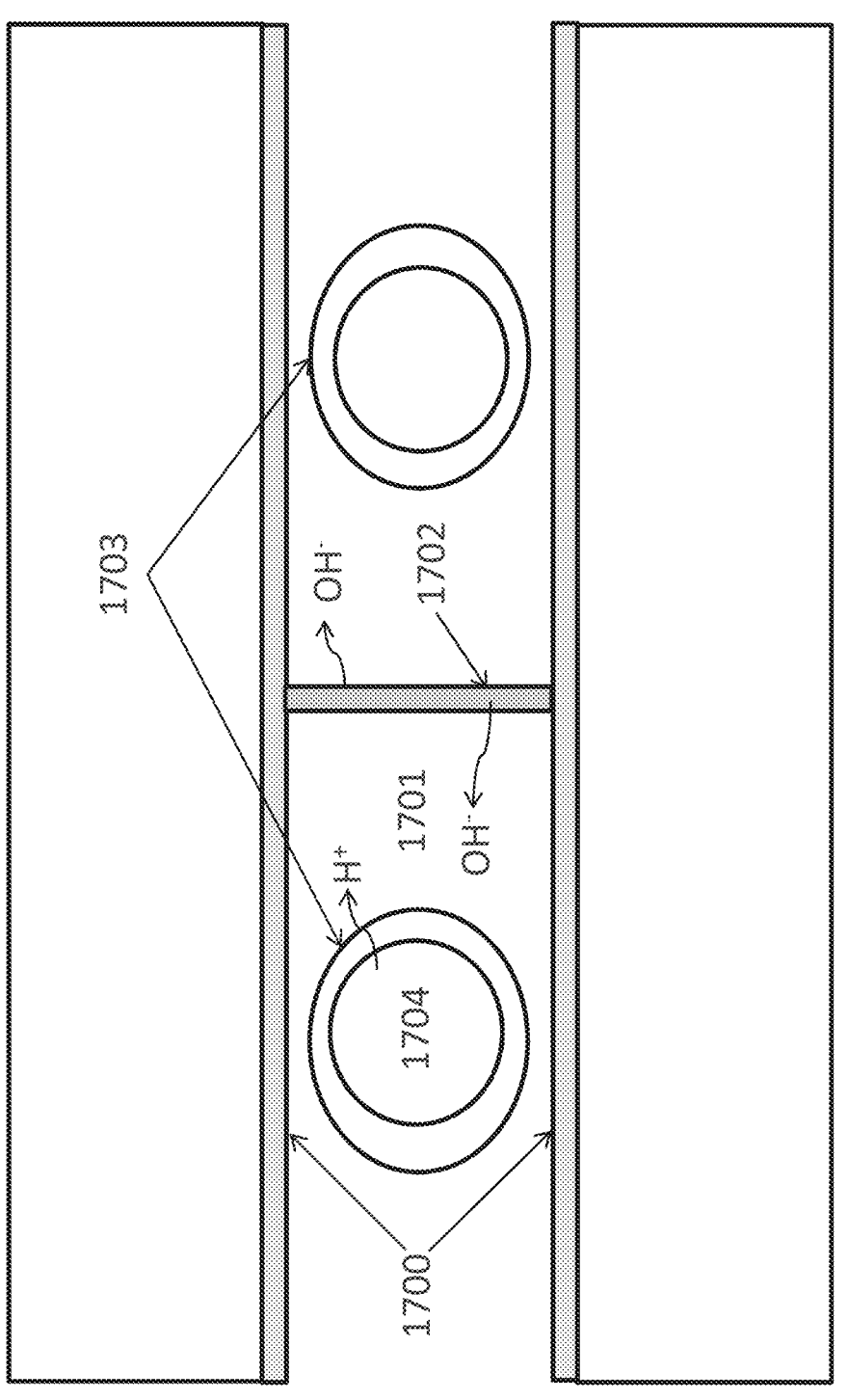
FIG. 17 is a top view schematic of a channel "chip".

FIG. 17 shows a top view of a channel chip design having three electrodes. Counter electrode elements 1700 and 1702 are located at the top of the two side channels and across the bottom of the flow channel 1701. Reference electrodes 1703 surround the two wells with working electrodes 1704 are also present.

In order to limit the flow of protons a series of steps may be taken, including (1) the use of buffers which prevent significant pH shifts in the presence of small amounts of protons, (2) the use of a quinone redox system, and (3) designing the dimensions of wells and channels to maintain substantial distances between them (e.g., using well volume 150 times smaller than according channel volume).

For example, using the schematic shown in FIG. 17 for purposes of illustration, the distances between the working electrode 1704 and counter electrode elements 1700 and 1702 may be about 200 μm. Further, interception of protons by base molecules may be used to decrease the number of protons that reach other wells. Also, reference electrode strips 1703 between wells having the same potential as the counter electrode elements 1700 and 1702 can be used to generate base molecules and further could prevent proton "cross-talk". Methods and components such as these, in addition to other methods set out herein, provide for high fidelity nucleic acid molecule synthesis.

For purposes of illustration, a prederivatized bead (e.g., a magnetic bead) may be placed in wells 1 through 5 of FIGS. 2A-2B with an "A" bead in wells 1 and 5, a "C" bead in well 2, a "U bead in well 3, and a "G" bead in well 4. All five wells may then be filled with an EGA reagent (e.g., a reagent containing methanol, acetonitrile, hydroquinone, anthraquinone, tetraethylamonium p-toluene sulfonate, and 2,6-lutidine). The next base to be added to chain is G and the only nucleic acid molecule of the molecules to be generated which contains a G at position 2 is in Well 1. Thus, current is applied only to Well 1. This current creates an acidic microenvironment which results in deprotection of the 5' position of the nucleotide only in Well 1. After a fixed (or variable) reaction time, all five wells are washed. A nucleotide, which has the phosphorus, sugar and a base (a T in this instance), is added to all of the wells in the presence of a catalyst (e.g., a tetrazole catalyst). After a predefined reaction time, all five wells are washed and unreacted first nucleotide may be capped to avoid accumulation of deletions, using, for example, acetic anhydride and N-methylimidazole. Again, after a predetermined reaction time, all five wells are washed and phosphite triesters formed by chemical reaction may be oxidized to form the more stable phosphate triester, using, for example, iodine containing reagents. This process is then repeated until the final base of the nucleic acid molecule has been added. Later, the synthesized nucleic acid molecules may be cleaved from the solid support. This may be done, for example, using aqueous or gaseous ammonia with heating. The cleavage method may vary, however, with factors such as the linker used.

The amount of current applied to each well and its duration will vary with parameters such as the amount of reagent to be generated and the size of the well. The applied current may be a pulse of varying shape and/magnitude. The pulse may define a series of varying amplitude pulses (frequency) or a gradual increase/decrease amplitude. The amplitude and duration of the pulse can be adjusted for the optimum generation of reagent. As an example, the current applied to a well may be adjusted for a specified period of time to generate a specified quantity of EGA. The amount of EGA intended for generation will typically be at least enough sufficient to fully catalyze deprotection of the nucleic acid molecules present.

In some aspects of the invention, "electrowetting" may be employed. Two aspect of the invention where electrowetting may be particularly useful is for the mixing of reagents for (1) nucleic acid synthesis and pooling (Modules 1 and 2) and (2) assembly (Module 3).

In brief, electrowetting involves modifying the surface tension of liquids on a solid surface using a voltage. Application of an electric field (e.g., alternating or direct), the contact angle between the fluid and surfaces can be modified. For example, by applying a voltage, the wetting properties of a hydrophobic surface can become increasingly hydrophilic and therefore wettable. Electrowetting principle is based on manipulating droplets on a surface comprising an array of electrodes and using voltage to change the interfacial tension. In some embodiments, the array of electrode is not in direct contact with the fluid. In additional embodiments, the array of electrode may be configured such as the support has a hydrophilic side and a hydrophobic side. The droplets subjected to the voltage will move towards the hydrophilic side. In some embodiments, the array or pattern of electrodes may be a high density pattern. When used in conjunction with the phosphoramidite chemistry (as well as other reagents), the array of electrodes should be able to move droplets volumes ranging from 1 pL (and less) to 10 pL. Accordingly, aspects of the invention relate to high voltage complementary semi-conductor microfluidic controller. In some embodiments, the high voltage complementary semi-conductor device (HV-CMOS) has an integrated circuit with high density electrode pattern and high voltage electronics. In some embodiments, the voltage applied is between 15V and 30V. Electrowetting methods are set out in U.S. Patent Publication No. 2012/0220497 A1, the disclosure of which is incorporated herein by reference.

Electrowetting works by using an electric voltage to alter the shape of a liquid drop. In some instances, electrowetting involves a sessile drop positioned on a dielectric-coated electrode. When current is applied, the drop flattens and flows out to the sides, thereby wetting additional surface. When current is removed, the drop returns to its original shape and retracts from the areas covered upon current application.

In some embodiments of the invention, nucleic acid synthesis site may have adjacent to is a series of reagents that flow into and recede from the synthesis site when current is applied to the correct reagent location. Thus, the invention includes methods for the synthesis of nucleic acid molecules by the addition and removal of reagents from a synthesis site induced by the addition and removal of current from adjacent reagents. In some instances, the number of reagents adjacent to a nucleic acid synthesis site may be from about 2 to about 10, from about 3 to about 10, from about 4 to about 10, from about 5 to about 10, from about 6 to about 10, etc.

Electrowetting methods may also be used for fragment assembly and error correction (Module 3). Thus, the invention includes methods for mixing reagents using electrowetting for the assembly and error correction of nucleic acid molecules. Reagents that may be contacted with nucleic acid molecules in these aspects of the invention include exonucleases, mist-match repair endonucleases (MMEs), ligases, buffers, EDTA solutions, etc.

One problem with electrowetting methods is "splash over" which may occur between mixing areas and also because, in many instances, planar or semi-planar surfaces are used. Thus, unless microfluidic drainage channels, or the like, are employed, there is a possibility of splash over contamination of mixing areas during reagent changes.

Two means for minimizing this mixing is through the use of microfluidic channels and barriers. Barrier may be placed (e.g., physical barriers such as raised areas) to prevent reagents from moving from one mixing area to another. After a desired reaction is finished, the barrier may be removed. Different reactions may be performed sequentially at different and/or overlapping subsets of mixing areas.

Polymer based physical barriers may be used in the practice of the invention. For example, these may be applied at the tops of wells and other areas where there is the potential for EGA cross contamination of "splash over". Typically, such polymers will not efficiently conduct electrical current. Exemplary polymer materials include natural and synthetic rubber.

As mentioned above, the methods of nucleic acid synthesis may be implemented and controlled in a system according to various embodiments described herein by a processor or computing system, such as the exemplary computing system depicted in FIG. 15. For example, applying current (pulse or continuous wave) to selected wells to generate a specific quantity of EGA to fully catalyze deprotection may be controlled by a computing system executing processor executable instructions according to various embodiments of the present teachings.

Deblocking may also occur through the use of redox systems. Examples of such system systems include hydroquinone/anthraquinone; pH buffer such as 2,6-lutidine to reduce proton cross talk between active wells and inactive neighboring wells.

Efficient production of nucleic acid molecules may require that nucleic acid synthesis steps be tailored to the molecules being constructed. Consider the example of the construction of nucleic acid molecules designed for construction of viral genome with a CG/AT ratio of 60/40. Nucleic acid molecule building blocks of such a genome will invariable have more Cs and Gs than As and Ts. In such an instance, it may be desirable to have more reactions which add Cs and Gs than As and Ts. As an example, the sequence of base addition may be a repetition of A T C G C A T G C G (SEQ ID NO: 1). Thus, the invention further includes chemical synthesis processes which are tailored for efficient production of specified nucleic acid molecules. In one aspect, this entails adding bases to nucleic acid molecules during chemical synthesis in manner which reflects or closely approximates the prevalence of the bases in those molecules.

The invention includes, for example, methods which result in high fidelity, microscale production of nucleic acid molecules. Thus, the invention includes methods by which nucleic acid molecules are produced with the following parameters: between $1\times10^5$ and $1.5\times10^9$ copies of a nucleic acid molecule are generated with an average number of base mis-incorporations of between 1 base in 100 and 1 base in 500. The invention includes similar methods with the parameters set out in Table 3.

TABLE 3

| Nucleic Acid Molecule Copies | No. of Base Mis-Incorporations (Avg.) |
|---|---|
| $1 \times 10^6$ and $1.5 \times 10^9$ | 1 in 150 to 1 in 500 |
| $1 \times 10^6$ and $1.5 \times 10^9$ | 1 in 150 to 1 in 400 |
| $1 \times 10^6$ and $1.5 \times 10^9$ | 1 in 100 to 1 in 300 |
| $1 \times 10^6$ and $1.5 \times 10^9$ | 1 in 200 to 1 in 400 |
| $1 \times 10^6$ and $1.5 \times 10^9$ | 1 in 300 to 1 in 1,000 |
| $1 \times 10^6$ and $1.5 \times 10^9$ | 1 in 300 to 1 in 2,000 |
| $1 \times 10^6$ and $1.5 \times 10^9$ | 1 in 500 to 1 in 4,000 |
| $1 \times 10^7$ and $1.5 \times 10^9$ | 1 in 150 to 1 in 500 |
| $1 \times 10^7$ and $1.5 \times 10^9$ | 1 in 150 to 1 in 400 |
| $1 \times 10^7$ and $1.5 \times 10^9$ | 1 in 100 to 1 in 300 |
| $1 \times 10^7$ and $1.5 \times 10^9$ | 1 in 200 to 1 in 400 |
| $1 \times 10^7$ and $1.5 \times 10^9$ | 1 in 300 to 1 in 1,000 |
| $1 \times 10^7$ and $1.5 \times 10^9$ | 1 in 300 to 1 in 2,000 |
| $1 \times 10^7$ and $1.5 \times 10^9$ | 1 in 500 to 1 in 4,000 |
| $1 \times 10^7$ and $1.5 \times 10^{10}$ | 1 in 150 to 1 in 400 |
| $1 \times 10^7$ and $1.5 \times 10^{10}$ | 1 in 100 to 1 in 300 |
| $1 \times 10^8$ and $1.5 \times 10^{10}$ | 1 in 150 to 1 in 400 |
| $1 \times 10^8$ and $1.5 \times 10^{10}$ | 1 in 100 to 1 in 300 |
| $1 \times 10^8$ and $1.5 \times 10^{10}$ | 1 in 200 to 1 in 400 |
| $1 \times 10^8$ and $1.5 \times 10^{10}$ | 1 in 300 to 1 in 1,000 |
| $1 \times 10^8$ and $1.5 \times 10^{10}$ | 1 in 300 to 1 in 2,000 |
| $1 \times 10^8$ and $1.5 \times 10^{10}$ | 1 in 500 to 1 in 4,000 |

Nucleic acid molecules prepared and used in accordance with the invention may contain modified nucleic acid molecules including locked nucleic acids (LNA), peptide nucleic acids (PNA), and the like. A PNA is a polyamide type of DNA analog, and the monomeric units for A, G, T, U, and C are available commercially. Furthermore, nucleic acid molecules of the invention may comprise one or more modified bases selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 8-azaguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, inosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, and 2,6-diaminopurine. The latter modified base can form three hydrogen bonds when base-paired with dT and can increase the $T^m$ of short nucleic acid molecules by as much as 1-2° C. per insertion. This effect, however, is complex and is dependent on sequence context.

2-Aminopurine can substitute for dA in a nucleic acid molecule. It is a naturally fluorescent base that is sensitive to the local environment making it a useful probe for monitoring the structure and dynamics of DNA hairpins and for detecting the base stacking state of a duplex. 2-aminopurine can be destabilizing and slightly lower the $T^m$. 5-Bromo-deoxyuridine is a photoreactive halogenated base that can be incorporated into nucleic acid molecules to crosslink them to DNA, RNA or proteins with exposure to UV light. Other modified bases such as inverted dT may be incorporated at the 3'-end of a nucleic acid molecule, leading to a 3'-3' linkage which inhibits both degradation by 3' exonucleases and extension by DNA polymerases. In another embodiment of the invention an inverted dideoxy-T may be placed at the 5' end of a nucleic acid molecule to prevent unwanted 5' ligations. A dideoxy-C(ddC) 3' chain terminator may be used to prevent 3' extension by DNA polymerases. 5-Methyl deoxy-C when substituted for dC will increase the $T^m$ by as much as 0.5° C. per insertion. In one embodiment the naturally occurring base deoxy-Inosine may be used which is less destabilizing than mismatches involving the four standard bases. Thus, the invention provides, in part, compositions and methods relating to the synthesis of modified nucleic acid molecules with novel properties and/or functions.

One modification of the plate format shown in FIG. 2 is to use a "liquid cover" to the wells. One way this could be performed is for the wells to contain a bilayer. For example, the bottom portion of the well containing the solid support could contain an EGA. Above this could be a lower density, optionally non-miscible, fluid. The lower density fluid layer will prevent or retard the diffusion of acid out of the desired well and over to an undesired well. Further, the lower density fluid can be positioned to make conductive contact with an upper electrode. One example of a commercially available "liquid coverslip" is sold by Ventana Medical Systems, Inc (cat. no. 650-010). This product is a solution used as a barrier between the aqueous reagents and the air, which prevents evaporation, and is designed to provide a stable aqueous environment for applications such as immunohistochemistry and in situ hybridization reactions.

One exemplary protocol for practicing methods of the invention is as follows. Porous silane-coated magnetic beads (MyOne Beads, Dynal) with a uniform diameter of 1 micron are added to the chip surface by controlled or pulsed flow to ensure uniform distribution of the beads across the microwells (about 1.3 μm diameter) on the chip and to ensure that a maximum number of wells are loaded with one bead. Wells not containing a bead are identified by a pre-synthesis current check that delineate the resistance difference among empty wells and well that contain a conductive magnetic bead.

A variety of chemistries are possible in the preparation of the bead surface. For example, a number of layers of silane can be produced to impart greater functional surface area to the beads. The silane coating(s) is/are prepared so that there is stable attachment of the hydroxyl functional group; typically through a trimethoxy or triethoxy silane linker, of the silane core to the naked silica bead surface to expose a primary hydroxyl group through with the initial amidite synthetic step is coupled. The fundamental chemistry, developed for a planar array surface electrode, for initiation and coupling in DNA synthesis can be found in Maurer et al., *Electrochemically Generated Acid and Its Containment to 100 Micron Reaction Areas for the Production of DNA Microarrays, PLoS ONE* 1(1): e34. doi: 10.1371/journal.pone.0000034 (2006).

Fabrication of the chip: Electrode materials such, as iridium metal up to 50 nm thick are produced on oxidized high-resistivity silicon selected for high conductivity and chemical stability under synthesis, reagent addition and deblocking conditions. Electrodes are connected by ultrasonic bonding to a printed circuit board to provide digitally controlled analogue integrated switch circuits activating electrodes chosen for deblocking a given well. Printed circuit boards are carefully aligned and bonded to the regular microwell structure to generate the synthesis chip. A cover plate providing and sealing the interior volume for reagents and a general complementary circuit electrode is bonded at the perimeter and over the upper surface of the microwell structure to complete the closed synthesis chip.

Conventional semiconductor or polymer material may be used for forming wells 200. For example, CMOS technology can be used to form wells of desired shape or size in the semiconductor material such as SiO or $SiO_2$. Depending on the desired application, electrodes 202 can be fabricates with wells 200 or separately.

Administration of nucleic acid synthesis (e.g., DNA synthesis) reagents to the chip can be performed by any number of means. For example, once the beads are loaded into the chip, a computing system controls a series of reagent additions and washings may be carried out to affect phosphoramidite DNA synthesis on the surface of the beads residing in the microwells of the chip. Processor-executable instructions may be employed which determine, for any given population of DNA sequences, the optimal order of DNA synthesis reagent additions and sequence of reagent additions and washing steps relative to volume/cost of reagents and time of a synthesis run. Furthermore, as mentioned above, controller or processor-controlled current to specific wells on the chip determine in which wells electrochemically generated acid may be produced and deprotection to activate the growing nucleic acid molecule on the bead in the well may be chemically prepared to couple the next amidite base added into the reaction vessel. A number of specific configurations of apparatus and components for administration of synthesis reagents and to ensure precise and controlled fluid administration are possible through an optimized development process.

Phosphoramidite DNA synthesis steps, conditions and reagents using EGA to affect deprotection can be found in, for examples, Maurer et al., *Electrochemically Generated Acid and Its Containment to* 100 *Micron Reaction Areas for the Production of DNA Microarrays, PLoS ONE* 1(1): e34. doi:10.1371/journal.pone.0000034 (2006) and Egeland and Southern, *Electrochemically directed synthesis of oligonucleotides for DNA microarray fabrication, Nucleic Acids Research,* 33(14):e125 (2005).

Composition and concentration of EGA components: The exact composition and concentration of EGA reagent is influenced by the precise conductive, structural and geometric properties of the electrodes and microwells and the parameters associated with the application (current, voltage and time) of current to convert the EGA to its acid forms. Generally, the smaller the volume for EGA production to affect deprotection, the smaller the required current strength and/or time of current application. Since the amount of nucleic acid molecule produced in such microscale systems falls below a threshold that can be directly and accurately measured, surrogate assays, such as hybridization or product enrichment following target amplification, for nucleic acid molecule synthesis and coupling efficiency are typically required. EGA reagents, including hydroxyquinone and benzoquinone, with tetrabutylammonium hexafluorophosphate in anhydrous acetonitrile are used to generate electrochemical acid via anodic oxidation to affect deprotection. EGA reagents above in concentration up to 25 mM are prepared and administered to the chip prior to the application of current to affect deprotection. In determination of the optimal parameters, it will generally be desirable to avoid base damage caused by depurination from over-exposure of DNA to acid.

Application of current to affect EGA-based DMT deprotection: Current may be applied constantly up to 2 ρA and voltage up to 2 V is applied to an electrode in the controlled circuit for a time period of up to 30 seconds. Current may also be applied in pulse durations from 10 to 2000 ms during a time of 1 to 60 seconds. Current may also be applied as in various pulses (e.g., from about two to about 10,000, from about ten to about 10,000, from about fifty to about 10,000, from about 100 to about 10,000, from about 1,000 to about 10,000, from about ten to about 500, etc. pulses) up to 2 pA (e.g., from about 0.02 nA to about 20,000 nA, from about 0.2 nA to about 20,000 nA, from about 0.2 nA to about 5,000 nA, from about 0.2 nA to about 2,000 nA, from about 0.2 nA to about 1,000 nA, from about 0.2 nA to about 5000 nA, from about 2.0 nA to about 20,000 nA, from about 2.0 nA to about 10,000 nA, from about 2.0 nA to about 5,000 nA, from about 2.0 nA to about 2,000 nA, from about 5.0 nA to about 20,000 nA, from about 5.0 nA to about 8,000 nA, from about 10 nA to about 20,000 nA, from about 10 nA to about 8,000 nA, from about 10 nA to about 5,000 nA, from about 20 nA to about 20,000 nA, from about 20 nA to about 8,000 nA, from about 50 nA to about 20,000 nA, from about 50 nA to about 10,000 nA, from about 50 nA to about 5,000 nA, from about 100 nA to about 10,000 nA, from about 500 nA to about 20,000 nA, from about 500 nA to about 10,000 nA, from about 500 nA to about 5,000 nA, from about 1,000 nA to about 20,000 nA, from about 1,000 nA to about 10,000 nA, etc.). In some instances, current will be pulsed for anywhere from about 1 second to about 30 seconds, from about 2 second to about 30 seconds, from about 4 second to about 30 seconds, from about 5 second to about 30 seconds, from about 5 second to about 20 seconds, from about 5 second to about 15 seconds, from about 5 second to about 10 seconds, etc. Of course, efficient deprotection and nucleic acid molecule synthesis must be determined as the exact composition and concentration of EGA reagent is influenced by the precise conductive, structural and geometric properties of the electrodes and microwells and the parameters associated with the application (current, voltage and time) of current.

In certain embodiments of the invention the nucleic acid molecule or a portion thereof may be subject to a sequence optimization process prior to synthesis. Different computational approaches for sequence modification are known in the art and may be employed to optimize a given nucleotide sequence in terms of 1) efficient assembly and/or 2) improved performance in a given host. To design a nucleotide sequence for optimal assembly, a full-length sequence may be broken down into a defined number of smaller fragments with optimal hybridization properties by means of an algorithm taking into account parameters such as melting temperature, overlap regions, self-hybridization, absence or presence of cloning sites and the like. In certain aspects of the invention, at least part of the desired nucleic acid sequence may encode a polypeptide or protein. In such cases, it may be desirable to optimize the open reading frame for improved performance in a given homologous or heterologous host, such as expression yield or solubility. An increase in gene expression may be achieved, for example, by replacing non-preferred or less preferred codons by preferred codons or by increasing the number of CpG dinucleotides in the open reading frame as described, for example, in U.S. Pat. Nos. 5,786,464 and 6,114,148 and U.S. Patent Publication No. 2009/0324546 AA, the disclosures of which are incorporated herein by reference.

In one specific embodiment, an optimized open reading frame may be combined with an algorithm to encrypt a secret message into the open reading frame as described in U.S. Patent Publication No. 2011/0119778 AA. Such message may allow the identification or tracking of certain synthetic nucleic acid molecules. In certain aspects of the invention, it may be desired to use an optimization strategy that takes into account multiple different parameters simultaneously including assembly—as well as expression-related sequence properties. One example of a comprehensive multiparameter approach that may be used in the current invention for optimized sequence design is the GENEOPTI-MIZER® technology described in U.S. Patent Publication No. 2007/0141557 AA, the disclosure of which is incorporated herein by reference. Thus, the invention provides in part aspects of optimal sequence design for downstream applications including assembly and expression strategies.

Module 2

After completion of a synthesis run on Module 1, support-associated (e.g., bead-associated) nucleic acid molecules may be subject to post-processing in Module 2. Processes performed in Module 2 may be performed manually or by computer directed automation controlling such steps as picking and pooling of a bead (e.g., a magnetic bead) from the synthesis microwell array and vapor-phase cleavage and deprotection to prepare the nucleic acid molecules for subsequent assembly steps, as appropriate.

To expose a microwell array of bead-attached nucleic acid molecules, the cover of the synthesis well, when present, may be removed. In one embodiment, the cover is removed by automatic means in a computer-controlled manner.

A bead picking instrument comprising, for example, a precision-controlled electro-micromagnet can be programmed and controlled to extract and pool individual beads harboring synthesized nucleic acid molecules. Depending on the application and the number of nucleic acid molecules to be assembled, all of the beads of the microwell array may be pooled or only a subset of the beads. When only a subset of the beads are pooled or when the total number of beads is limited, the number of beads pooled may vary widely and include from about 10 to about 50, from about 50 to about 100, from about 100 to about 1000, from about 50 to about 10,000, from about 100 to about 10,000, or from about 500 to about 10,000 individual beads. These beads may be deposited in any suitable container. One example of a container is the well of a microwell plate (e.g., a well of a 1536 microwell plate).

Automation suitable use with the invention includes a precision-controlled electromicromagnet picks up the first bead and deposits it into a pooling well (i.e., a well which contains multiple beads for collection of nucleic acid molecules sought to be used in combination). Alternatively, a precision-controlled electromicromagnet can be used which picks up the first bead and then moves in the X-Y direction to the next position, lowers down in the Z direction to pick up the second bead, back up in the Z direction to get out of the magnetic field range, moves to the third well in the X-Y direction, etc. Thus, the magnet is left "on" and the set of beads (e.g., from about two to about fifty, from about ten to about fifty, from about two to about one hundred, from about ten to about one hundred, from about twenty to about eighty, etc.) is picked up and carried as a string of beads. As a set of beads is collected, this set is then deposited in simultaneously deposited into a pooling well. Of course, multiple sets of beads may be collected and deposited in a single pooling well.

In some instances, beads may be extracted and pooled using systems as described, for example, in U.S. Patent Publication Nos. 2008/0281466 AA or 2008/0113361 AA or in U.S. Pat. Nos. 6,887,431; 7,347,975 or 7,384,606, the disclosures of which are incorporated herein by reference. In other embodiments of the invention a bead picking instrument with at least one integrated precision-controlled electro-micromagnet may be used. Such a picking instrument may be controlled by a control unit which can be programmed to control the movement of the micromagnet to align with specific microwells. In a further embodiment, the control unit may provide means to control the adjustment of the distance between the micromagnet and the microwell. In a specific embodiment, the micromagnet may be controlled and activated by electric means to allow extraction of single magnetic beads carrying a specific nucleic acid sequence.

Electro-micromagnets used in the current invention may be hollow magnets or needle shaped and will often be of a size and dimension to focus the magnetic field at its tip to allow for specific targeting of individual beads. In a specific embodiment, the micromagnet may be composed of an electro-magnet and a permanent magnet wherein the activity of the permanent magnet can be controlled by the electro-magnet. Electro-micromagnet used in conjunction with the invention may be in any number or format and may, for example, comprise a single magnet or be arranged together with other micromagnets in a row.

In certain embodiments of the invention, an electro-micromagnet may be used to extract and pool all magnetic beads contained in the microwells of a single arrays. For this purpose, the electro-micromagnet may be allocated to each microwell to extract the bead-attached nucleic acid molecules in a step-wise manner in a pre-defined or random order. In one embodiment, all nucleic acid molecules required for the assembly of a full-length construct may be synthesized on a single array. According to the amount of nucleic acid molecules required to build a full-length construct, arrays of different sizes and dimensions can be used.

In another embodiment, the electro-micromagnet may be programmed to target only a portion of the microwells of a specific array to extract and pool a predefined selection of bead-attached nucleic acid molecules. The electro-micromagnet can be programmed to extract and pool beads from the microwells of two or more different plates. The picking may combine full extraction of all beads of a first plate with selective extraction of a portion of beads obtained from a second plate. The first and the second plate may vary in size and dimension.

Each magnetic bead extracted by the micromagnet may then be transferred to a pooling station by moveable means of the picking instrument. In one embodiment the pooling station may contain a chamber with a microwell plate. In one embodiment the microwell plate may be a 1536 microwell plate. However, microwell plates of other sizes and dimensions (e.g., standard 96 well plates) are known in the art and can be used in the current invention. Defined fractions of nucleic acid molecules can be pooled in individual wells of a microwell plate wherein one pooled fraction contains all nucleic acid molecules required to assemble at least a defined fragment of a full-length construct. In one embodiment, an individual nucleic acid molecule pool may contain all nucleic acid molecules required to assemble a full-length construct. Different nucleic acid molecule pools allocated to each well can be further identified using a machine readable identifier disposed on the microwell plates.

Electrostatic forces may also be used to remove beads and other substrates from synthesis platforms. Using FIGS. 2A-2B for purposes of illustration, oligonucleotide synthesis substrates (beads in this instance) may have an electrostatic charged and separated from association with a surface or well using an opposite charge. For example, if one or more beads shown in FIGS. 2A-2B have a positive charge then the lower electrode may be used to generate a positive charge to repel the bead and force it from the well. Magnetic charges can also be used to achieve the same purpose. Residual magnetism may also be employed. In essence, residual magnetism is magnetism that remains in a material after being exposed to magnetic force. In many instances, magnetic substrates will be of small size. Thus, attraction of such substrates will typically not requires strong magnetic fields. Residual magnetism may be present in the substrate a selection probe used to bind to the substrate or both. Further, charges may be used to selectively remove a subset of synthesis substrates from a synthesis platform.

Electrostatic forces for required for the removal of beads and other substrates from synthesis platforms can be readily calculated. TABLE 4 below assumes a relative homogeneous electrical field is present and that each bead acts as a single charge point. Nucleic acid molecules carry with them a charge which should be taken into consideration when charge is used to extrude a bead from a well. Further, charge need only be applied to wells that contain substrates with desired nucleic acid molecules (e.g., nucleic acid molecules for assembly into larger nucleic acid molecules.

TABLE 4

| Number of Strands | Charge per Strand (As) | Electrode Voltage (V) | Electrode Distance (in) |
|---|---|---|---|
| 1,000,000 | $1.6 \times 10^{-19}$ | 2 | $1.00 \times 10^{-5}$ |

|  |  |  | Electrode Distance (μm) |
|---|---|---|---|
|  |  |  | 10 |

| Point Charge (As) | Electric Field Strength (V/m) | Force N |
|---|---|---|
| $1.6 \times 10^{-13}$ | 200000 | 0.000000032 |

|  | Electric Field Strength (V/mm) | Force μN |
|---|---|---|
|  | 200 | 0.032 |

In another embodiment, a synthesis platform may contain a series of regions that separate from other regions of the synthesis platform. For example, a synthesis platform may contain 100 rows of synthesis areas in a square 10×10 arrangement. Further, the synthesis platform may be designed so that it is separatable into ten rows of ten synthesis areas. For purposes of illustration, assume that one seeks to produce eight different assembled nucleic acid molecules and these assembled nucleic acid molecules are designed to be formed from the assembly of the following number or oligonucleotides:

TABLE 5

| Assembled Nucleic No. | No. of Oligos | Row No. |
|---|---|---|
| 1 | 7 | 1 |
| 2 | 8 | 2 |
| 3 | 8 | 3 |
| 4 | 9 | 4 |
| 5 | 9 | 5 |
| 6 | 10 | 6 |
| 7 | 13 | 7-8 |
| 8 | 15 | 9-10 |

Table 5 indicates the numerical designation of the various assembled nucleic acid molecules, the number of oligonucleotides that will be used to assemble the assembled nucleic acid molecules, and the rows in which the oligonucleotides are synthesized in. In this embodiment, rows 1-5 will each have at least one synthesis area in which no oligonucleotides will be produced.

After synthesis is completed, the separatable rows may be separated and the synthesized nucleic acid molecules, collected/processed and assembled, for example, as described elsewhere herein.

Other methods may also be used to collect nucleic acid synthesis substrates, including (1) "grabbing", for example by the use of tweezers like devices which operate based upon mechanical (e.g., actual grabbing), optical, sonic, magnetic principles, (2) "destroying" structures surrounding nucleic acid synthesis substrates by methods such as chemical dissolution or through the use of lasers, (3) moving nucleic acid synthesis substrates by, for example, the use of thermal, electrostatic, magnetic, fluidic energy, (4) hybrid gripper which combine, for examples, (a) magnetic and fluidic flushing, (b) magnetic and piezoelectric methods, and (c) electrostatic lifting and fluidic flushing, (5) magnetic fixing/collecting using, for example, modulated permanent magnets, external coils, planar coils on synthesis substrates, etc., (6) electrostatic lifting & collecting, and (7) flux direction (e.g., the addition of fluid to the bottom of a well to lift substrates).

Pooling stations used in the practice of the invention may further contain a microwell handling device which comprises controllable moveable means for moving the microwell plate from a first to at least a second position in X and/or Y and/or Z direction and can be programmed to perform liquid handling steps. Such pooling stations may further be equipped with a pipetting device and a suction apparatus allowing for controlled addition and removal of reagents. Alternatively the removal of liquid can be performed by vacuum means. The pipetting device may further be connected to reagent reservoirs and mixing means to mix and add defined amounts of reagents required for purification and subsequent processing and assembly steps. Integrated liquid handling devices combining the respective functions are known by those skilled in the art.

In a specific embodiment, the pooling station integrates means to allow for further combining of one or more nucleic acid molecule pools from first and second wells into a third well to yield a larger nucleic acid molecule pool. Such step-wise pooling may be required in cases where variants or libraries of full-length constructs are assembled from identical and variable sequence elements.

Pooling stations used in the practice of the invention may further contain a magnet located beneath the microwell plate. In a specific embodiment such a plate magnet may serve as counterpart to the micromagnet in order to trigger release of the extracted beads into the recipient microwell. Alternatively the electro-micromagnet may be a hollow magnet connected to a capillary that can be flushed with liquid to blow out the bound bead into the recipient well. Other means of bead release may also be employed.

With respect to pooling of nucleic acid molecules, this may be done any number of ways. For example, synthesis substrates may be collected and placed in a single contained. Alternatively, nucleic acid molecules may be released from synthesis substrates and then contacted with each other. Further, nucleic acid molecules may be assembled by hybridization. This means that more than one assembly may occur in the same container. In other words, the invention includes methods by which assembly of more than one (e.g., two, three, four, five, six, etc.) nucleic acid molecule occurs from smaller, chemically synthesized nucleic acid molecules. One application where the assembly of more than one larger nucleic acid molecule (e.g., replicable nucleic acid molecules) may be useful is where the assembled nucleic acid molecules are intended for insertion into the same cell. Thus, one of the assembled nucleic acid molecules could be a chromosome and another could be a plasmid.

Once desired pools of nucleic acid molecules have been generated, bead-attached nucleic acid molecules will often be further processed, for example, to obtain functional nucleic acid molecules for downstream reactions. After chain synthesis the 5'-terminal 5'-hydroxy group is usually protected, for example, with a dimethoxytrityl (DMT) group; the internucleosidic phosphate or phosphorothioate moieties may also be protected, for example, with 2-cyanoethyl groups; and the exocyclic amino groups in all nucleic bases (except for T and U) may be protected, for example, with acyl protecting groups. Usually, the 5'-terminal DMT group is cleaved after the last synthesis cycle on the support before the bead-attached nucleic acid molecules are pooled. However, all protection groups have to be removed in a deprotection step before the nucleic acid molecules can be effectively used in subsequent processes.

In one embodiment of the invention, deprotection is performed, for example, without releasing the nucleic acid molecule form the bead. This can be carried out by choosing a base-stable, non-cleavable linker. Respective linkers are known by the skilled person.

In one embodiment, nucleic acid molecules are released from the beads prior to downstream assembly. If cleavage of nucleic acid molecule is required, cleavage and deprotection may be performed in a single step. Release of the nucleic acid molecules may be achieved by cleaving the linker attaching the 3'-end of the nucleic acid molecule to the bead (e.g., a magnetic bead) with a suitable reagent. Suitable reagents and conditions for cleavage depend on the nature of the linkage as described elsewhere herein and are known by those skilled in the art.

In one embodiment of the invention, nucleic acid molecules are attached to the magnetic beads via succinyl groups. The succinyl linker may be cleaved by the use of, for example, concentrated aqueous ammonium hydroxide. The reaction is usually carried out at temperatures between 50° C. and 80° C. for at least one to about eight hours. Of course, cleavage conditions may vary depending on the protocol and the protecting groups used. The ammonia solution may then removed by evaporation, leaving the nucleic acid molecules ready for purification.

In one embodiment, cleavage may be carried out by vapor-phase processing. In vapor-phase processing, nucleic acid molecules may be cleaved in a closed chamber in a gaseous environment comprising gaseous cleavage/deprotection reagent, such as gaseous ammonia or ammonium hydroxide vapors. Respective methods are set out, for example, in U.S. Pat. Nos. 5,514,789 or 5,738,829, the disclosures of which are incorporated herein by reference.

The above reaction will typically also triggers cleavage of other protecting groups including the cyanoethyl group, the group protecting the heterocyclic primary amine and the DMT group on the very last base. Thus, a single cleavage reaction may be used, when appropriate, to remove all protecting groups present.

Linkers used in the practice of the invention may be cleaved using at least two approaches: (a) simultaneously under the same conditions as the deprotection step or (b) subsequently utilizing a different condition or reagent for linker cleavage after the completion of the deprotection step. Various methods to remove universal linkers from a nucleic acid molecule are described in the art such as, for example, U.S. Patent Publication No. 2002/0143166 A1, the disclosure of which is incorporated herein by reference.

For downstream applications, it may be required to purify the pooled and deprotected nucleic acid molecules to remove the cleaved groups, for example, by precipitation. It may further be required to separate the nucleic acid molecule mixture from the magnetic particles or other support. In one embodiment, a plate magnet located beneath the microwell plate can be used to immobilize the beads in the wells while the nucleic acid molecules can be eluted, for example, by suction. Alternatively, in the absence of a plate magnet, the beads may be automatically removed from the wells by magnetic means while the nucleic acid molecules would be retained in the well to obtain femtomoles of individual pools of high quality nucleic acid molecules at picomole concentration ready for further processing or use.

In some instances, nucleic acid molecules may be separated from solid support while the solid supports remain localized in the same or similar location as to where the nucleic acid molecules were synthesized. In such instances, typically after synthesis completion, oligonucleotide synthesis reagents may be removed from contact with synthesis supports, followed by the addition of one or more reagents for release of the constructed oligonucleotide, also referred to as cleavage reagents. These releasing reagents may be in forms such as liquid or gaseous. Gaseous reagents are referred to above.

In many instances, the cleavage reagent agent will be volatile (e.g., it can be removed via freeze drying) and non-ionic. The cleaved oligonucleotides may then be recovered by either removal from wells, when present, or by rinsing the synthesis substrate. When microwells are employed for synthesis, cleavage reagents in liquid form may be used. The synthesis substrate may be coated with such liquid reagents followed by either group removal of synthesized oligonucleotides or removal of individual oligonucleotides (less than all of oligonucleotides present). Removal of individual oligonucleotides may be achieved, for example, by limiting agitation of the substrate and site specific removal (e.g., with a pipette tip) of fluid containing individual oligonucleotides after cleavage has occurred. Such methods will be particularly useful when the substrate contains wells or cavities.

Optionally, synthesized nucleic acid molecules may be concentrated step after pooling, cleavage and/or deprotection but to entering into Module 3 processes. One concentration method of such concentration would be by an additional second binding, washing, and elution series of sets to reduce the final volume. This increased concentration will increase the concentration of synthesized nucleic acid molecules, resulting in accelerated hybridization of overlapping segments in sub-fragment generation as may be desired. Concentration to an increased concentration may also be used to "normalize" the concentration of multiple pools to a more constant range so that a limited set of, for example, assembly conditions need be employed in Module 3 processes (e.g., all Module 3 processes).

Figure 13:
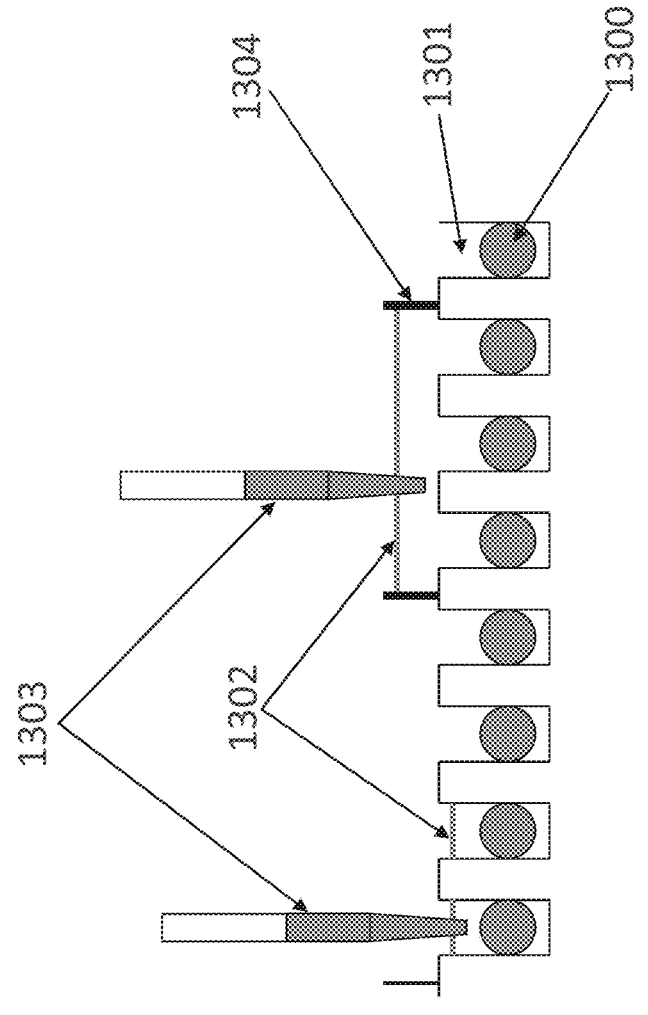
FIG. 13 shows two different fluid removal options for microwell plate embodiments of synthesis platforms.
Figures 14A, 14B:
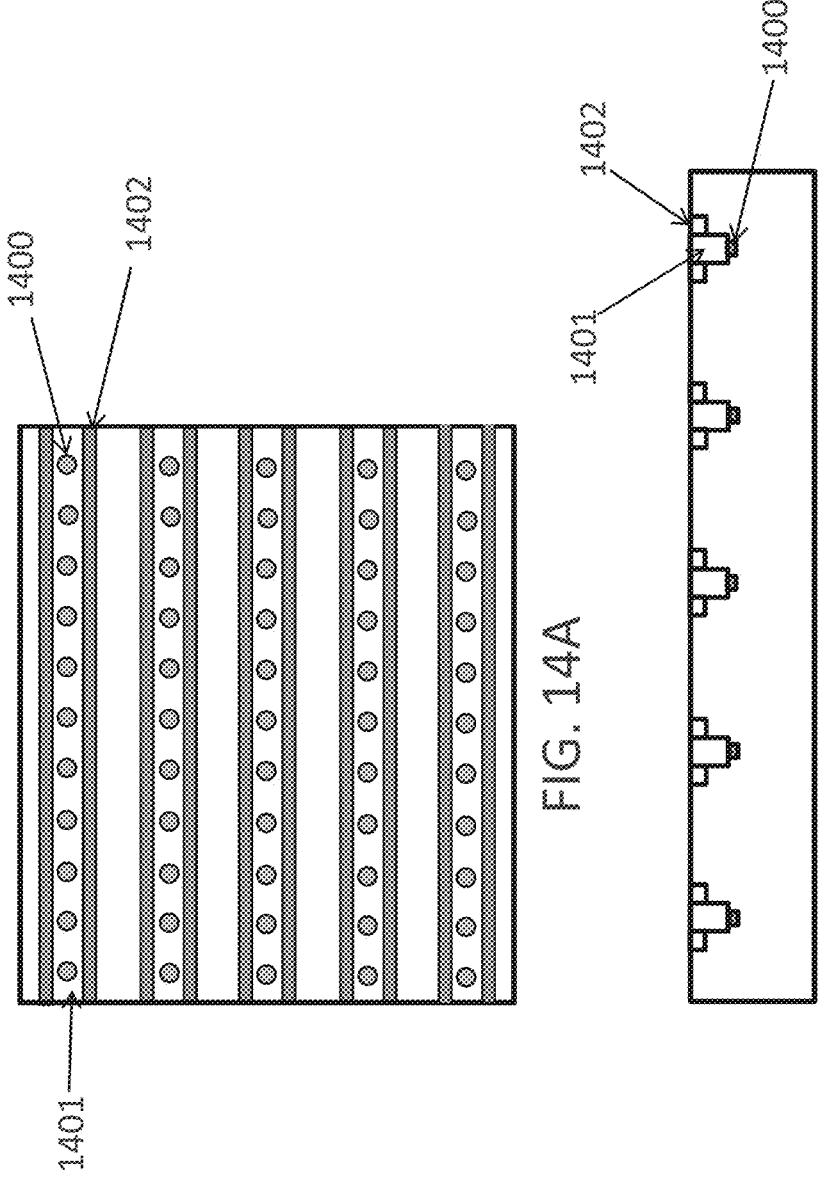
FIGS. 14A-14B show two different views of a nucleic acid molecules synthesis platform designed to generate identical nucleic acid molecules in each row 1401.

FIG. 13 shows two methods by which synthesized oligonucleotides may be separated from supports. In this figure, oligonucleotides have been synthesized on beads 1300 and released into the surrounding well of a microwell titer plate 1301. In each instance, wells containing oligonucleotides for collection are covered with fluid 1302 and pipette tips 1303 are used to collect that fluid. On the left side of the figure are two wells where the fluid is contained within the wells. Further to the right side of FIG. 13, a barrier 1304 extends above the wells to allow fluid to collect at a higher level. In both instances, the fluid may be there before the pipette tips are brought into close proximity or the fluid may be delivered by the pipette tips. Also, fluid surrounding the beads 1300 may be circulated to distribute released oligonucleotides by flow delivered by the pipette tips 1303.

Module 3

Once the chemical synthesis phase has been completed, the resulting nucleic acid molecules may be assembled, if desired, into larger nucleic acid molecules. Depending on the end purpose for which the final nucleic acid molecules are to be used, the "quality" (e.g., from a sequence fidelity perspective) of the chemically synthesized nucleic acid molecules may be too low for the intended application. As an example, if the chemically synthesized nucleic acid molecules are to be used as long probes, then they may be of sufficient quality for that purpose without further processing. However, consider the situation where one hundred nucleic acid segments are to be assembled, each nucleic acid segment is one hundred base pairs in length and there is one error per fifty base pairs. The net result is that there will be, on average, 200 sequence errors in each 10,000 base pair assembled nucleic acid molecule. If one intends, for example, to express one or more proteins from the assembled nucleic acid molecule, then the number of sequence errors would likely be considered to be too high. Also, while sequencing of individual nucleic acid molecules may be performed, this is time consuming and involves additional cost. Thus, in many instances, an error removal step may be performed. Typically, this will be performed after a first round of assembly. Thus, in one aspect, methods of the invention involve the following (in this order or different orders):

1. Fragment Amplification and Assembly (e.g., PCR/in vitro assembly).
2. Error Correction.
3. Final Assembly (e.g., in vivo assembly).

In various embodiments of the present disclosure, error removal steps may also be implemented by executing processor-executable instructions. The invention thus includes software based instructions for performing mechanical functions associated with error removal processes, as well as other aspects of the invention.

Any number of methods may be used for fragment amplification and assembly. One exemplary method is described in Yang et al., *Nucleic Acids Research*, 21:1889-1893 (1993) and U.S. Pat. No. 5,580,759, the disclosure of which is incorporated herein by reference.

In the process described in the Yang et al. paper, a linear vector is mixed with double stranded nucleic acid molecules which share sequence homology at the termini. An enzyme with exonuclease activity (i.e., T4 DNA polymerase, T5 exonuclease, T7 exonuclease, etc.) is added which peels back one strand of all termini present in the mixture. The "peeled back" nucleic acid molecules are then annealed incubated with a DNA polymerase and deoxynucleotide triphosphates under condition which allow for the filling in of single-stranded gaps. Nicks in the resulting nucleic acid molecules may be repaired by introduction of the molecule into a cell or by the addition of ligase. Of course, depending on the application and work flow, the vector may be omitted. Further, the resulting nucleic acid molecules, or sub-portions thereof, may be amplified by polymerase chain reaction.

Other methods of nucleic acid assembly include those described in U.S. Patent Publication Nos. 2010/0062495 A1; 2007/0292954 A1; 2003/0152984 AA; and 2006/0115850 AA and in U.S. Pat. Nos. 6,083,726; 6,110,668; 5,624,827; 6,521,427; 5,869,644; and 6,495,318, the disclosures of which are incorporated herein by reference.

A method for the isothermal assembly of nucleic acid molecules is set out in U.S. Patent Publication No. 2012/0053087, the disclosure of which is incorporated herein by reference. In one aspect of this method, nucleic acid molecules for assembly are contacted with a thermolabile protein with exonuclease activity (e.g., T5 polymerase) a thermostable polymerase, and a thermostable ligase under conditions where the exonuclease activity decreases with time (e.g., 50° C.). The exonuclease "chews back" one strand of the nucleic acid molecules and, if there is sequence complementarity, nucleic acid molecule will anneal with each other. The thermostable polymerase fills in gaps and the thermostable ligase seals nicks. Methods like this may be used in conjunction with equipment of FIG. 16. Further, more than one nucleic acid molecule may be stored with other suitable reagents in the individual storage units of 1609 and these storage units may be set to a temperature of, for example, of 50° C. for assembling the stored molecules.

One commercially available kit which may be used to assemble nucleic acid molecules of the invention, as well as for the insertion of such nucleic acid molecules into vectors is the GENEART® Seamless Cloning and Assembly Kit (cat. no. A13288), available from Life Technologies Corp., Carlsbad, CA.

Single-stranded binding proteins such as T4 gene 32 protein and RecA, as well as other nucleic acid binding or recombination proteins known in the art, may be included, for example, to facilitate nucleic acid molecules annealing.

In some instances, nucleic acid molecules may be amplified on solid supports. Thus, the invention includes methods where nucleic acid molecules are synthesized but are not cleaved from solid supports they are synthesized on. In such instances, the amplified nucleic acid molecules may be used directed (e.g., as probes) or assembled as described elsewhere herein.

Figure 3:
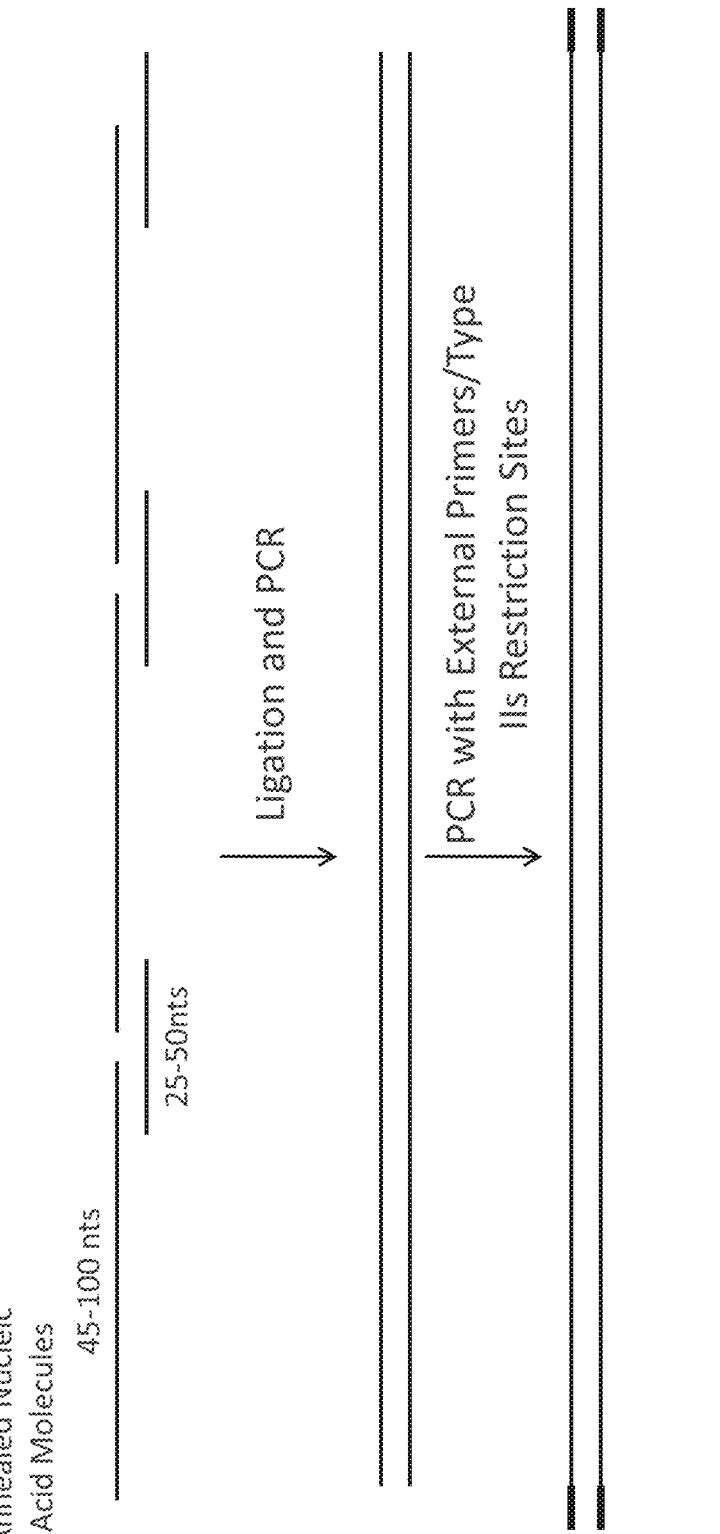
FIG. 3 shows a nucleic acid assembly scheme. The thick ends on the assembled nucleic acid molecule shown at the bottom of the figure represent regions added by external primers, also referred to as terminal primers.

One method for assembling nucleic acid molecules (FIG. 3) involves starting with overlapping nucleic acid molecules which are "stitched" together using PCR. In many instances, the stitched nucleic acid molecules will be chemically synthesized and will be less than 100 nucleotides in length (e.g., from about 40 to 100, from about 50 to 100, from about 60 to 100, from about 40 to 90, from about 40 to 80, from about 40 to 75, from about 50 to 85, etc. nucleotides). A process similar to that shown in FIG. 3 is set out in U.S. Pat. No. 6,472,184, the disclosure of which is incorporated herein by reference. Primers may also be used which contain restriction sites for instances where insertion into a cloning vector is desired. One suitable cloning system is referred to as Golden Gate which is set out in various forms in U.S Patent Publication No. 2010/0291633 A1 and PCT Publication WO 2010/040531, the disclosures of which are incorporated herein by reference. Thus, where desirable, assembled nucleic acid molecules may be directly inserted into vectors and host cells. This may be appropriate when the desired construct is fairly small (e.g., less than 5 kilobases). Type IIs restriction site mediated assembly may be used to assemble multiple fragments (e.g., two, three, five, eight, ten, etc.) when larger constructs are desired (e.g., 5 to 100 kilobases).

An alternative method for PCR-based assembly of nucleic acid molecules (e.g., chemically synthesized nucleic acid molecules) is based on the direct ligation of overlapping pairs of 5'-phosphorylated nucleic acid molecules ("ligation-based assembly"). In this process, single-stranded nucleic acid molecules are synthesized, phosphorylated and annealed to form double-stranded molecules with complementary overhangs (e.g., overhangs of four nucleotides). The individual double stranded molecules are then ligated to each other to form larger constructs. In certain embodiments this method may be desirable over PCR methods in particular where highly repetitive sequences, such as GC stretches are to be assembled. This method may be used to assemble from about two to about forty nucleic acid molecules (e.g., from about two to about forty, from about three to about forty, from about five to about forty, from about eight to about forty, from about two to about thirty, from about two to about twenty, from about two to about ten, etc. nucleic acid molecules). A related method is described in U.S. Pat. No. 4,652,639, the disclosure of which is incorporated herein by reference.

In many instances when ligation-based assembly is employed using chemically synthesized nucleic acid molecules, the molecules will be less than 100 base pairs in length. Also, the complementary overlaps may be used for joining the nucleic acid molecules will generally be between two and ten (e.g., from about two to about ten, from about four to about ten, from about five to about ten, from about two to about eight, from about three to about seven, etc. nucleotides in length) (FIG. 4).

One process that may be used to assemble nucleic acid molecules is Red/ET recombination. This process employs *E. coli* based homologous recombination mediated by phage protein pairs, such as RecE/RecT or Redα/Redβ. This process is not limited by nucleic acid size and is independent of restriction sites. Essentially any DNA molecule in *E. coli* of almost any size can be engineered at any site using Red/ET recombination. In essence, Red/ET recombination involves three steps/conditions. The first step or condition is the presence of homology arms (e.g., arms of 50 base pairs in length) in linear DNA. The second step or condition is the insertion or presence of the linear DNA in an *E. coli* cell. The third step or condition is the expression or presence of any appropriate phage pair (e.g., RecE/RecT or Redα/Redβ) in the *E. coli* cell. Red/ET recombination is set out in U.S. Pat. Nos. 6,355,412 and 6,509,156, the disclosures of which are incorporated herein by reference.

Figure 4:
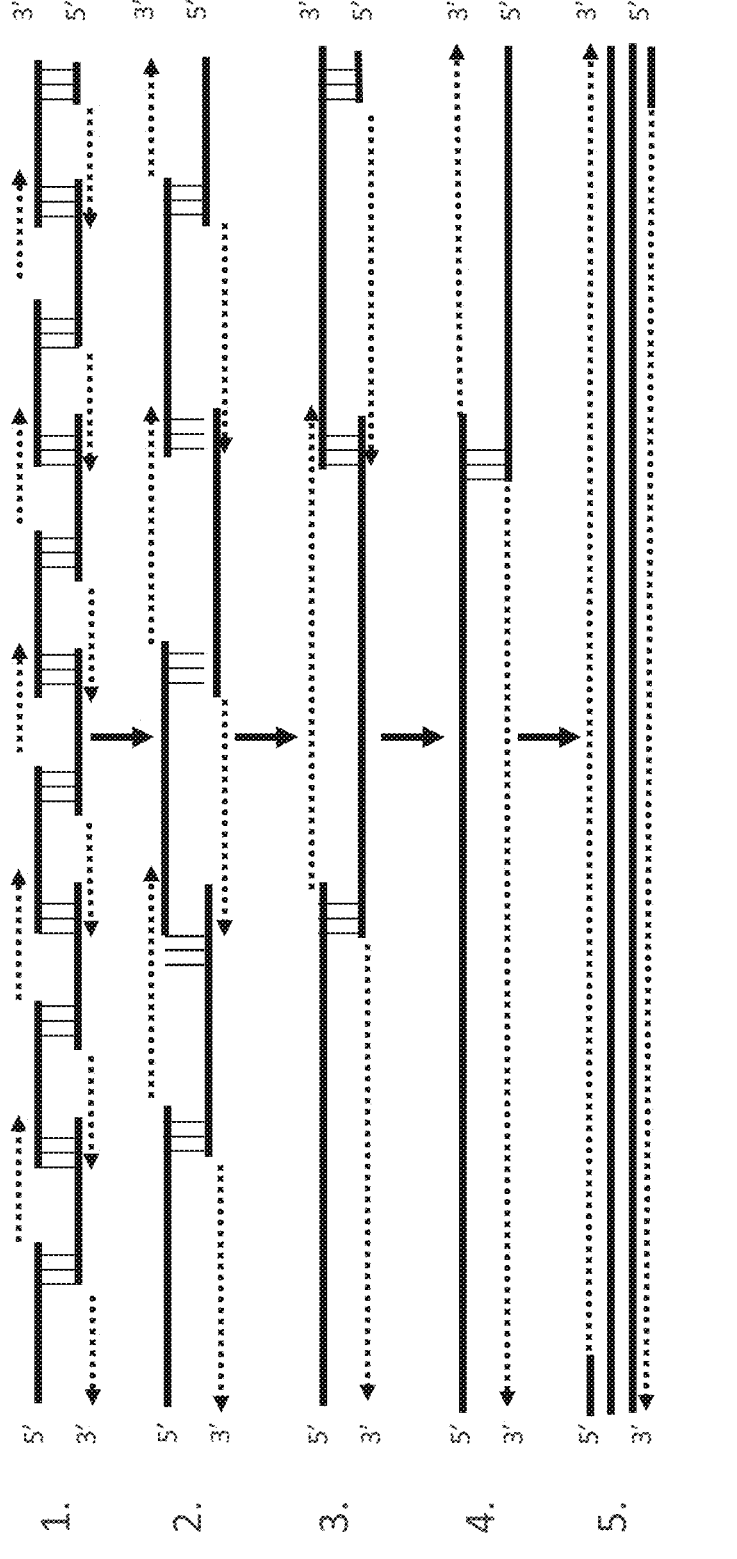
FIG. 4 shows a second nucleic acid assembly scheme. Dotted lines with arrows show PCR based synthesis direction and area.

Further, as shown in FIG. 4, multiple rounds of polymerase chain reactions may be used to generate successively larger nucleic acid molecules.

In some embodiments, nucleic acid molecules are assembled after amplification and/or are assembled by processes involving amplification. Further, after partial or final assembly, assembled nucleic acid molecules may be used directly or introduced into cells where cellular based amplification may occur.

Some exemplary nucleic acid assembly methods that may be used in the practice of the invention or employed as standalone processes include (1) Chain Reaction Cloning (CRC), (2) Circular Polymerase Extension Cloning (CPEC), and (3) Oligonucleotide Stitching Assembly (OSA), as well as combinations of these methods.

Chain Reaction Cloning (CRC) involves the use if a bridging oligonucleotide to join the termini of two other nucleic acid molecules. While variations of the CRC method may be used, one exemplary method involves preparing a reaction mixture comprising (1) two double-stranded nucleic acid molecules having termini having no sequence complementarity with each other, (2) a single-stranded oligonucleotide that shares sequence complementarity with one terminus of each of the two double-stranded nucleic acid molecules, and (3) a thermostable ligase. This reaction mixture is then cycled to temperatures above and below the melting point of the two double-stranded nucleic acid molecules, as represented in FIG. 18.

CRC may involve more than two (e.g., three, four, five, six, seven, etc.) double-stranded nucleic acid molecules and more than one (e.g., three, four, five, six, seven, etc.) bridging oligonucleotide. Further, CRC may be performed in phases where, for example, a several nucleic acid molecules (e.g., three) are connected to each other, then additional nucleic acid molecules are added and additional cycles are performed.

The number of cycles performed will vary with factors such as the amount of two double-stranded nucleic acid molecules originally present in the reaction mixture and the amount of ligated nucleic acid that is desired.

Figure 18:
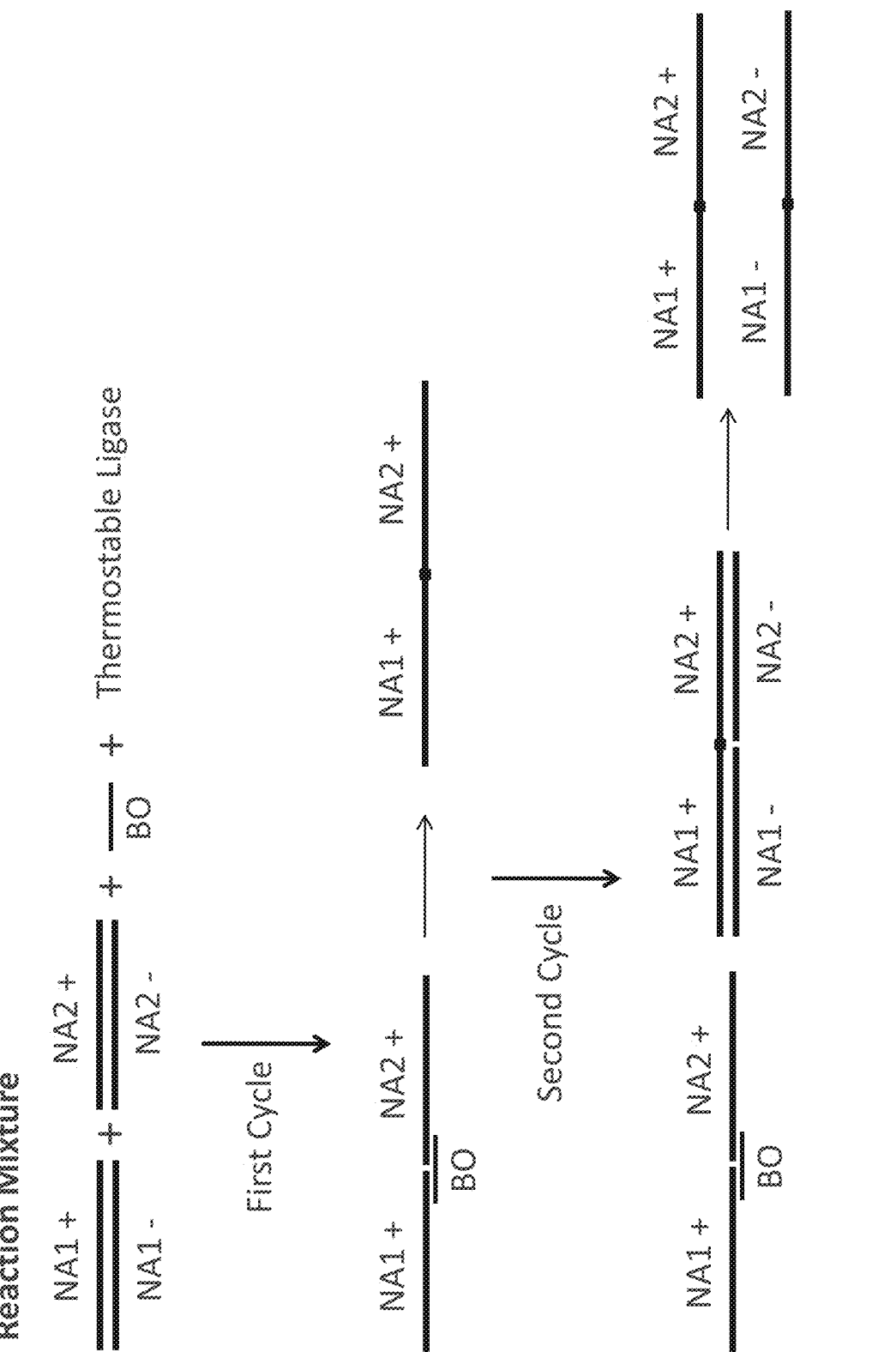
FIG. 18 is a schematic representation of a Chain Reaction Cloning (CRC) process. Initially a reaction mixture is prepared containing two double-stranded nucleic acid molecules (NA1 and NA2), a bridging oligonucleotide (BO) and a thermostable ligase. This reaction mixture is heated to a temperature above the melting point of the two double-stranded nucleic acid molecules (strands indicated by + and −), then cooled to allow for annealing. In instances where the BO connects NA1+ and NA2+, the ligase connects the termini, with the junction point shown as a solid box. In later cycles of heating and cooling, ligated NA1+ and NA2+ and NA1− and NA2− single-stranded nucleic acid molecules (see lower far right of FIG. 18) hybridize with their complements, that are then ligated to each other by the ligase.

The CRC process shown in FIG. 18 results, after the first couple of cycles, in the logarithmic ligation of nucleic acid molecules present in the reaction mixture. Also, one advantage of this assembly process is that a polymerase is not employed. Thus, nucleic acid polymerase mediated errors are not introduced into the assembled nucleic acid molecules.

In a variation of the process shown in FIG. 18, the double-stranded nucleic acid molecules in the original reaction mixture can be single-stranded. In such instances, the reaction mixture will often contain a fairly high concentration of the bridging oligonucleotide. This is so because if only the + strands of the nucleic acid molecules being assembled are present, then essentially all of the assembled nucleic acid molecules will be brought together by the BO. Thus, the assembled nucleic acid molecules will not act as hybridization partners because their complementary strands would not be present.

The CRC process is set out in Pachuk et al., *Gene* 243:19-25 (2000) and U.S. Pat. No. 6,143,527, the entire disclosure of which is incorporated herein by reference. One disadvantage of this approach is that ligation of DNA fragments with non-compatible ends (e.g., 3'protruding end of fragment 1 and 5' protruding end of fragment 2) may not lead to the exact desired junction. Thus, the assembly is not always seamless and does not allow for junction editing.

Figure 19:
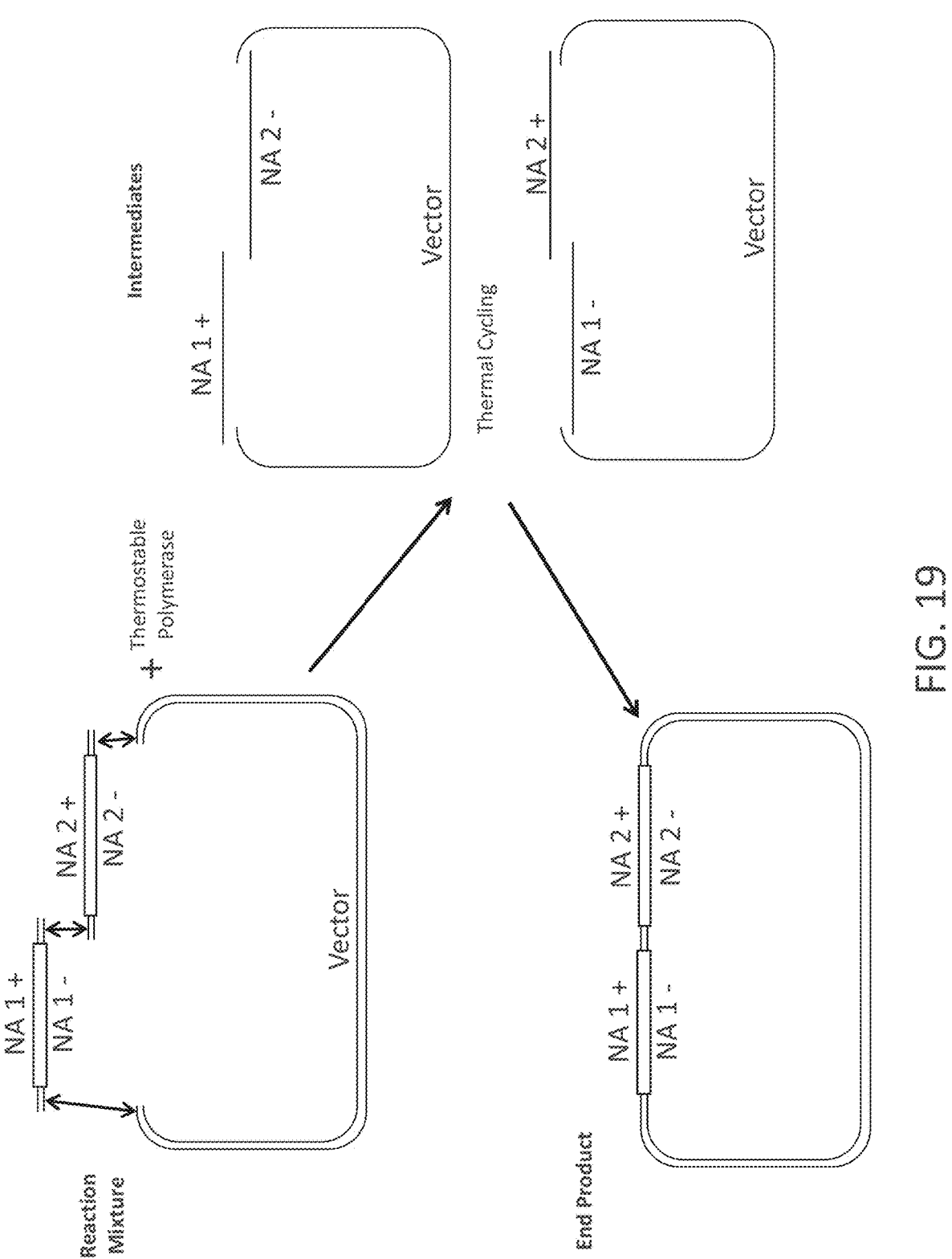
FIG. 19 is a schematic representation of a Circular Polymerase Extension Cloning (CPEC) process. Initially a reaction mixture is prepared containing (1) two double-stranded nucleic acid molecules (NA1 and NA2) having overlapping regions of sequence complementarity at the termini (indicated by the double headed arrows) with each other and ends of a linearized vector and (2) a thermostable polymerase. The + and—signs indicate the sequence "polarity" of the nucleic acid strands.

FIG. 19 shows a schematic representation of one embodiment of the CPEC process. In this embodiment, a double stranded, linear vector and two double-stranded nucleic acid molecules are combined with a thermostable polymerase and nucleoside triphosphates (e.g., deoxynucleoside triphosphates) to form a reaction mixture. This reaction mixture is then heated to separate the strands of the vector and nucleic acid molecules and then cooled, allowing for hybridization of complementary sequences, followed by extension to generate double-stranded end products. The CPEC process is set out in Quan and Tian, *PloS One* 4:e6441 (2009) and Quan and Tian, *Nature Protocols* 6:242-251 (2011).

As one skilled in the art would understand, CPEC may be employed to connect more than two (e.g., three, four, five, six, seven, etc.) nucleic acid molecules. Further, assembled nucleic acid molecules need not be introduced into a vector. Thus, CPEC may be used assemble multiple nucleic acid molecules to form a linear or circular assembly, wherein the final assembly may or may not have the ability to replicate when introduced into a cell. Further, PCR, especially repeated PCR reactions, may introduce errors into the assembled nucleic acid molecules.

Figure 20:
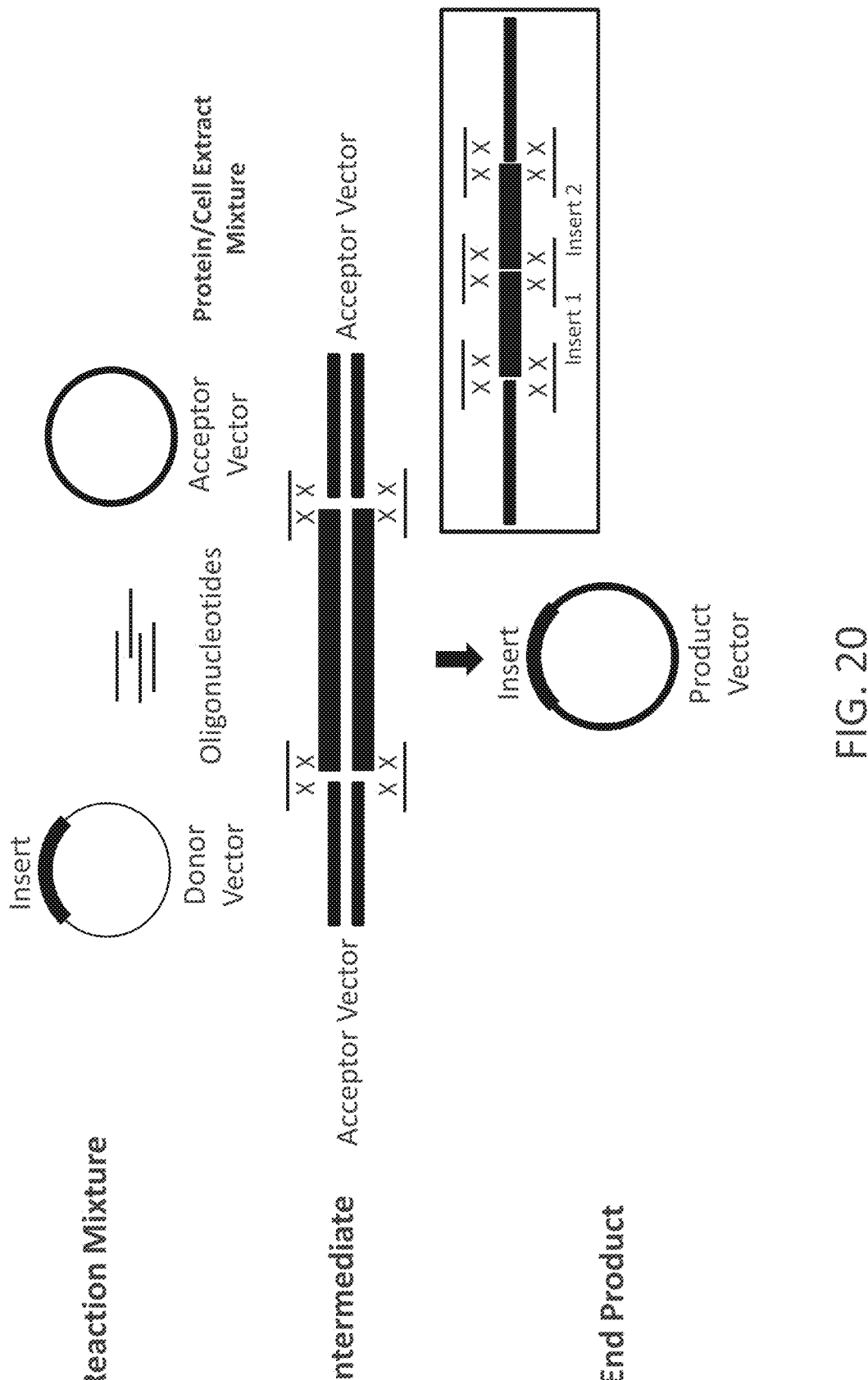
FIG. 20 is a schematic representation of an Oligonucleotide Stitching Assembly (OSA) process. In this process a reaction mixture containing (1) a donor vector, (2) an acceptor vector, (3) four oligonucleotides with sequence complementarity (represented by "X"s) to the insertion locus of the acceptor vector and the insert of the donor vector, and (4) a protein composition/cell extract mixture. The insert will often be excised from the Donor Vector by, for example, the use of a restriction enzyme. The box on the lower right shows a variation where six oligonucleotides are used to introduce two inserts into an acceptor vector. The numbers below the data bars refer to the numbers of overlapping base-pairs in the stitching oligonucleotides. The double-stranded character of the non-oligonucleotide nucleic acid molecules is not represented in this box.

FIG. 20 shows an embodiment of Oligonucleotide Stitching Assembly (OSA). In this embodiment, an insert present in a donor vector is introduced into an acceptor vector. This is mediated by (1) oligonucleotides which share sequence complementarity with both the insert and the insertion locus of the acceptor vector and (2) a mixture of enzymes and a cell extract. Typically, the insert will be excised for the donor vector prior to or as part of the reaction process. In many instances, this will be accomplished by digestion with a restriction enzyme.

OSA may be used to assemble nucleic acid molecules produced by methods of the invention, as well as other nucleic acid molecules. Thus, the invention includes OSA methods. Such methods include: (a) forming a reaction mixture of (1) an insert nucleic acid molecule, an acceptor nucleic acid molecule, oligonucleotides, wherein each oligonucleotide shares sequence complementarity with (i) one terminus of the insert nucleic acid molecule and the insertion site of the acceptor nucleic acid molecule or (ii) one terminus of two different insert nucleic acid molecules, (2) a cell extract, (3) a protein composition comprising an exonuclease and, optionally, a single-stranded binding protein (e.g., T4 gene 32 protein); and (b) incubating the reaction formed in (a) under conditions which allow for the introduction of the insert nucleic acid molecule into the acceptor nucleic acid molecule. The invention also includes reagents and components used in such methods, as well as kit for performing such methods.

The process described above is directed to the introduction of a single insert into a single acceptor nucleic acid molecule. As one skilled in the art would understand, one or more (e.g., one, two three, four, five, six, seven, eight, nine, ten, etc.) insert nucleic acid molecule may be introduced into one or more (e.g., one, two three, four, five, six, seven, eight, nine, ten, etc.) acceptor nucleic acid molecule. In some instances, more than one insert nucleic acid molecule may be introduced into one acceptor nucleic acid molecule. One example of this is shown in the box on the lower right of FIG. 20. In this exemplary embodiment, two double-stranded insert nucleic acid molecules (the double-stranded nature of the nucleic acid molecules not being shown in the boxed representations) are introduced into a double-stranded acceptor vector. As shown in FIG. 20, six oligonucleotides are used in this process, with two pairs of oligonucleotides having sequence complementarity with the junction regions between the two inserts (one pair for each insert/acceptor vector junction) and each terminus of the insertion locus of the acceptor vector.

The number of oligonucleotides present will generally vary with the number of inserts to be introduced into the acceptor nucleic acid molecule (e.g., a vector). For one insert, four oligonucleotides will generally be present; for two inserts, six oligonucleotides will generally be present; for three inserts, eight oligonucleotides will generally be present. Thus, two oligonucleotides will generally be present for each joining point, with the number of oligonucleotides present being represented by the following formula: $O=2+2I$, where O is the number of oligonucleotides and I is the number of insert nucleic acid molecules.

The invention thus includes OSA methods (e.g., in vitro methods) comprising: (a) forming a reaction mixture of (1) one or more insert nucleic acid molecule, one or more acceptor nucleic acid molecule, a plurality of oligonucleotides, wherein each oligonucleotide shares sequence complementarity with one terminus of the insert nucleic acid molecule and the insertion site of the acceptor nucleic acid molecule and wherein the number of oligonucleotides is represented by the formula $O=2+2I$, where O is the number of oligonucleotides and I is the number of insert nucleic acid molecules, (2) a cell extract, (3) a protein composition comprising an exonuclease and, optionally, a single-stranded binding protein (e.g., T4 gene 32 protein); and (b) incubating the reaction formed in (a) under conditions which allow for the introduction of the insert nucleic acid molecule into the acceptor nucleic acid molecule.

The lengths of the oligonucleotides may vary but they will typically be between from about 20 and about 100 (e.g., from about 20 to about 80, from about 30 to about 80, from about 40 to about 80, from about 20 to about 60, from about 20 to about 50, from about 20 to about 40, from about 30 to about 80, from about 30 to about 60, etc.) nucleotides in length. Further, the regions of sequence complementarity of oligonucleotides to each component of an insertion junction (i.e., the acceptor nucleic acid molecule and the insertion nucleic acid molecule) will typically be between from about 20 and to about 60 (e.g., from about 20 and to about 50, from about 40 and to about 60, from about 25 and to about 60, from about 25 and to about 50, from about 25 and to about 40, from about 25 and to about 35, etc.) nucleotides.

Figure 21:
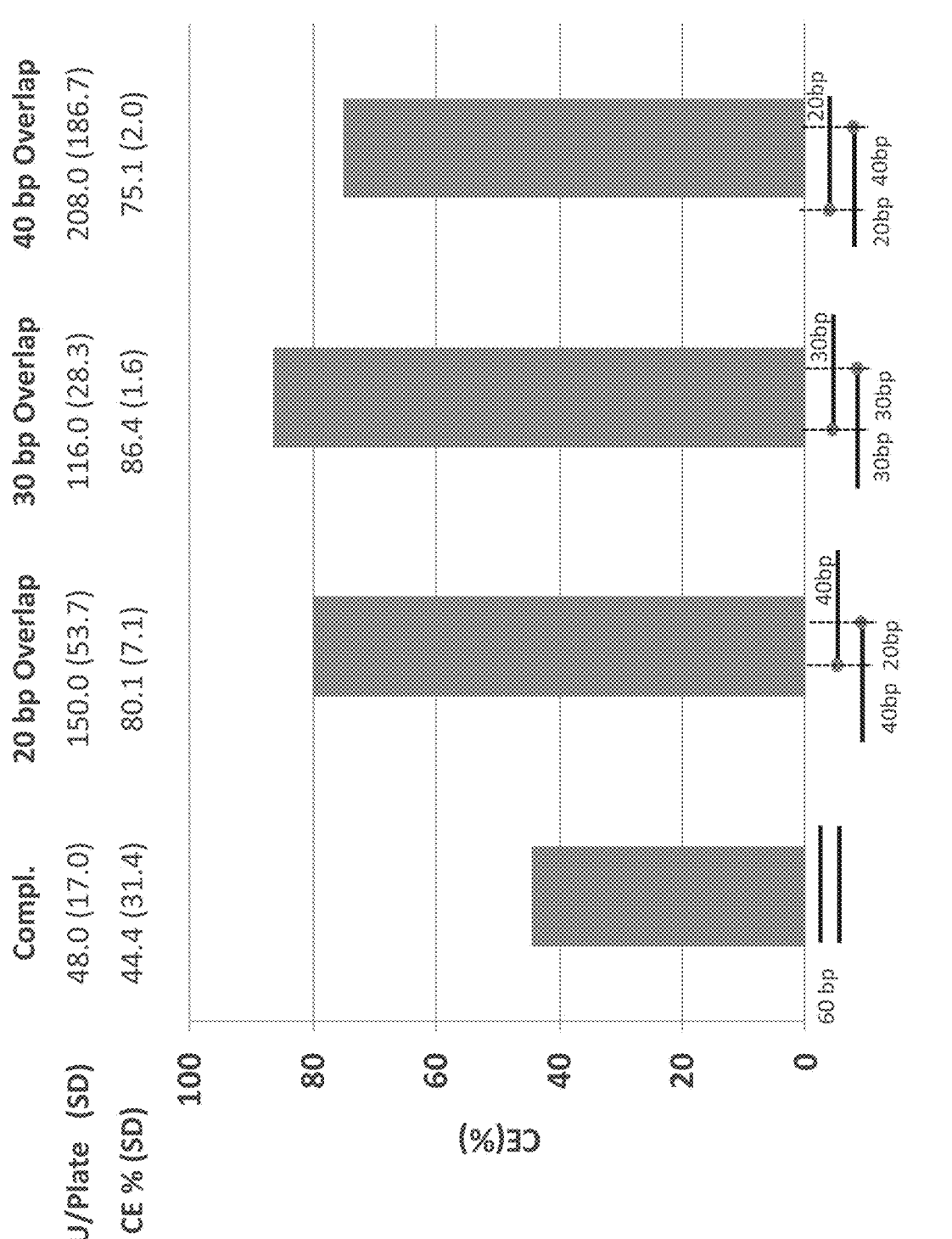
FIG. 21 shows a series of OSA experiments using a cell extract from *E. coli* strain DH10B, one acceptor vector and two insert nucleic acid molecules. Different forms of oligonucleotides 60 nucleotides in length were tested. These oligonucleotides were either full complementary or had different sized overhangs and lengths of sequence complementarity with each other. Abbreviations: CE=Cloning Efficiency, SD=Standard Deviation, CFU=Colony Forming Units.
Figure 22:
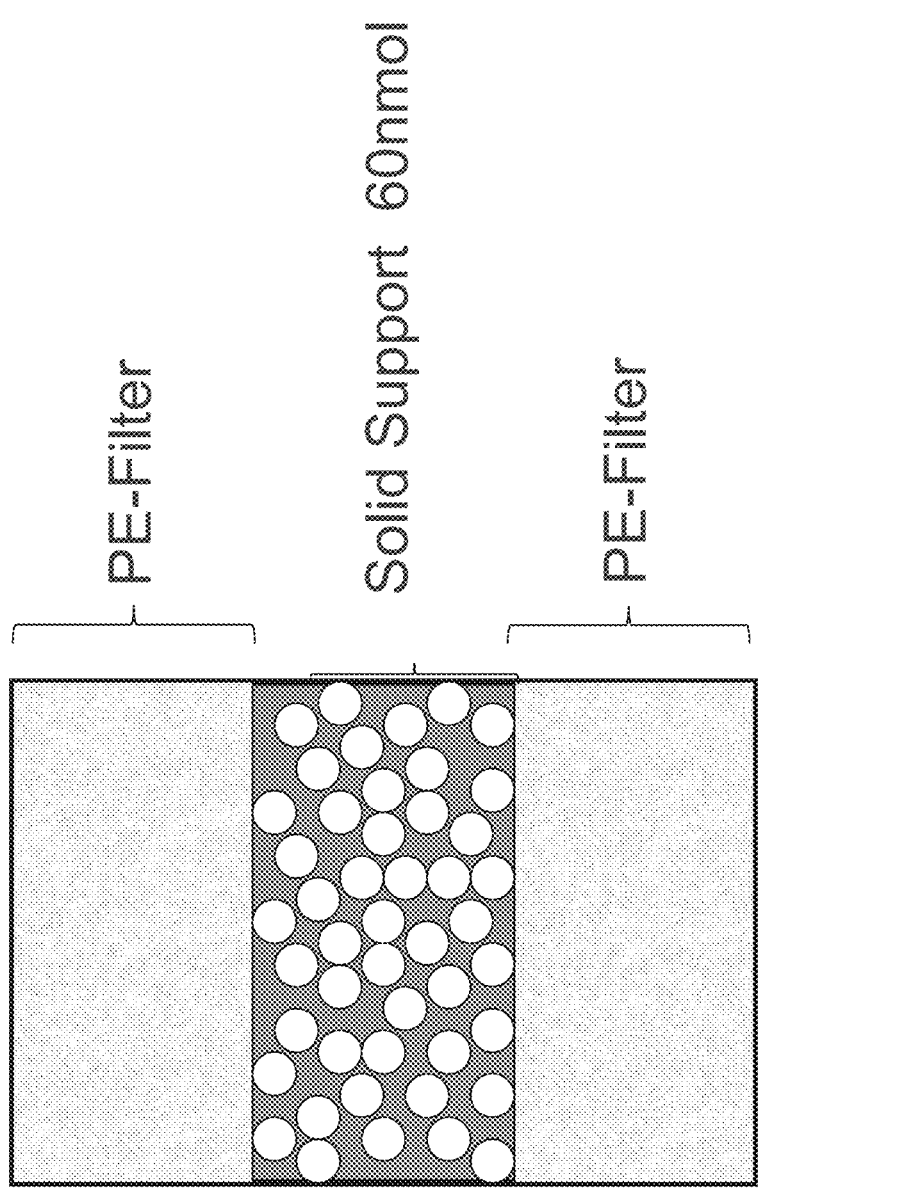
FIG. 22 shows a solid phase synthesis chamber used for oligonucleotide synthesis methods of the examples. Polyethylene (PE) filter material has a diameter 2.7 mm and a pore size 60-70 μm. The solid support was obtained from CPG (Biosearch Technologies Inc.) and was derivatized with one of four initial bases depending on the first base of the oligonucleotides to be synthesized. CPG A: 5'-DMT-dA (Bz)-Suc-CPG 1000 A: Catalog Number: BG1-1000, loaded 40 μmol/g, CPG C: 5'-DMT-dC(Bz)-Suc-CPG 1000 A: Catalog Number: BG1-1100, loaded 40 μmol/g, CPG G: 5'-DMT-dC(iBu)-Suc-CPG 1000 A: Catalog Number: BG1-1200, loaded 40 μmol/g, CPG T: 5'-DMT-T-Suc-CPG 1000 A: Catalog Number: BG1-1300, loaded 40 μmol/g were used.

As shown by the data in FIG. 21, offset oligonucleotides yield higher cloning efficiencies than full complementary oligonucleotides. Also, the data shown in FIG. 21 was generated using a cell extract obtained from *E. coli* DH10B cells. Similar cloning efficiencies were obtained using extracts of *E. coli* cells expressing redET genes, demonstrating that redET gene products are not necessary for OSA. Thus, the invention includes methods involving the use of cell extracts derived from cells that do not express redET genes. Further, the redET gene expression products are believed to not interfere with the OSA process so their presence is optional.

The invention thus includes in vitro OSA methods involving the use of cell extracts and protein compositions. Extracts may be prepared from any number of cell types, including prokaryotic (e.g., bacterial cells) and eukaryotic cells (e.g., yeast cells). Exemplary prokaryotic cells include those of bacteria of bacterial groups, families, such as bacteria in the phylum Actinobacteria, such as organisms of the class Actinobacteridae, such as organisms of the order Actinomycetales, such as organisms of the families Actinomycineae: Actinomycetaceae (*Actinomyces, Mobiluncus*), Corynebacterineae: Mycobacteriaceae (*Mycobacterium*), Nocardiaceae, Corynebacteriaceae, Frankineae: Frankiaceae, Micrococcineae: Brevibacteriaceae and Propionibacteriaceae (*Propionibacterium*) and of the order Bifidobacteriales, such as organisms of the families Bifidobacteriaceae (*Bifidobacterium, Falcivibrio, Gardnerella*) and other subclasses: Acidimicrobidae, Coriobacteridae, Rubrobacteridae, Sphaerobacteridae; and of the phylum Firmicutes, such as organisms of the class Bacilli, such as organisms of the order Bacillales, such as organisms of the families: Bacillaceae (*Bacillus*), Listeriaceae (*Listeria*), Staphylococcaceae (*Staphylococcus, Gemella, Jeotgalicoccus*) and of the order Lactobacillales, such as organisms of the families: Enterococcaceae (*Enterococcus*), Lactobacillaceae (*Lactobacillus, Pediococcus*), Leuconostocaceae (*Leuconostoc*), Streptococcaceae (*Lactococcus, Streptococcus*) and of the class Clostridia, such as organisms of the order: Clostridiales (*Clostridium, Peptostreptococcus, Selenomonas*), Halanaerobiales and Thermoanaerobacterales, and of the class Tenericutes/Mollicutes, such as organisms of the order: Mycoplasmatales (*Mycoplasma, Ureaplasma*), Entomoplasmatales (*Spiroplasma*), Anaeroplasmatales (*Erysipelothrix*), Acholeplasmatales (*Acholeplasma*), Haloplasmatales (*Haloplasma*). Specific bacterial cells that may be used to produce cell extracts for use in the invention include *Staphylococcus aureus, Enterococcus faecalis, Streptococcus* spp., *Escherichia coli, Klebsiella pneumoniae, Proteus mirabilis*, and *Pseudomonas aeruginsa*.

Exemplary eukaryotic organisms that may be used to produce cell extracts for use in the invention include yeasts such as *Saccharomyces cerevisiae, Saccharomyces carsvergensis, Saccharomyces logos, Saccharomyces fragilis, Saccharomyces sake, Schizosaccharomyces pombe, Saccharomyces paradoxus, Zygosaccharomyces japonicas, Pichia polymorpha, Pichia farinose, Pichia haplophila, Pichia saitoi Hansenula saturnus, Kuraishia capsulate, Wickerhamomyces silvicola, Kuraishia capsulate, Ogataea glucozyma, Ogataea minuta, Debaryomyces hansenii, Debaryomyces hansenii, Naumovia castellii, Hanseniaspora valbyensis, Sporidiobolus salmonicolor, Yarrowia lipolytica, Candida solani*, and *Candida albicans*.

Acceptor nucleic acid molecules (e.g., acceptor vectors) may be of any number forms or lengths. In many instances, acceptor nucleic acid molecules will be vectors but in some instances such molecules may lack an origin of replication and may be designed to integrate into the genome or other nucleic acid molecule in a cell. Further, the insertion site may be one which results in negative selection phenotype (e.g., encode ccdB, or other toxic compounds such that introduction of the insert results in disruption of the coding region and a resulting loss of the negative selection phenotype.

Protein compositions for use in OSA methods will typically contain at least an exonuclease activity and may optionally contain a single-stranded binding protein. Exemplary proteins with exonuclease activity that may be used in the practice of the invention include proteins polymerases and other proteins with exonuclease activity. This activity may be 5'→3' or 3'→5' activity. Specific proteins with exonuclease activity that may be used in the practice of the invention include Exonuclease I, Exonuclease III, Exonuclease V, Exonuclease VII, T7 exonuclease, Taq DNA polymerase, phage T7 gene 6 product, RedA of lambda phage, and RecE of Rac prophage. Single-stranded binding proteins that may be used in the practice of the invention include recA, *E. coli* single-stranded binding protein (SSB), *Xanthomonas* SSB, *Lactococcus lactis* siphophage p2 SSB, Rim1 SSB, T7 SSB (T7 gene 2.5 product), and T4 gene 32 protein.

Kits of the invention may contain one or more of the following components: (1) one or more oligonucleotide, (2) one or more protein with exonuclease activity, (3) one or more cell extract, (4) one of more cell type and, optionally, instructions for the preparation of one or more cell extracts, (5) one or more vector nucleic acid molecule, (6) one of more reagent, such as buffers and salts. These reagents may be in dry form or in solution. In many instances, the applications of those using kits of the invention will be different enough that oligonucleotides will not be included. Comment components that may be included are items (2), (3), (4), and (6) above.

The invention further includes reactions mixtures and combinations of intermediates and end products. Using FIG. 20 for purposes of illustration, the invention includes compositions of matter comprising one or more Donor Vector, one or more Acceptor Vector, a plurality (e.g., two, three, four, five, six, seven, eight, nine, ten, etc.) of oligonucleotides, at least one protein with exonuclease activity, at least one cell extract, one or more Acceptor Vector at various states of introduction of one or more Insert, and one or more Product Vectors.

From a functional perspective, the invention includes compositions of matter comprising one or more nucleic acid insert, one or more acceptor nucleic acid molecules, a plurality (e.g., two, three, four, five, six, seven, eight, nine, ten, etc.) of oligonucleotides, at least one protein with exonuclease activity, at least one cell extract, wherein the composition is capable of facilitating the introduction of the insert into the acceptor nucleic acid molecule.

In most instances, regardless of the method by which a larger nucleic acid molecule is generated from chemically synthesized nucleic acid molecules, errors from the chemical synthesis process will be present. Thus, in many instances, error correction will be desirable. Error correction can be achieved by any number of means. One method is by individually sequencing chemically synthesized nucleic acid molecules.

Figure 6:
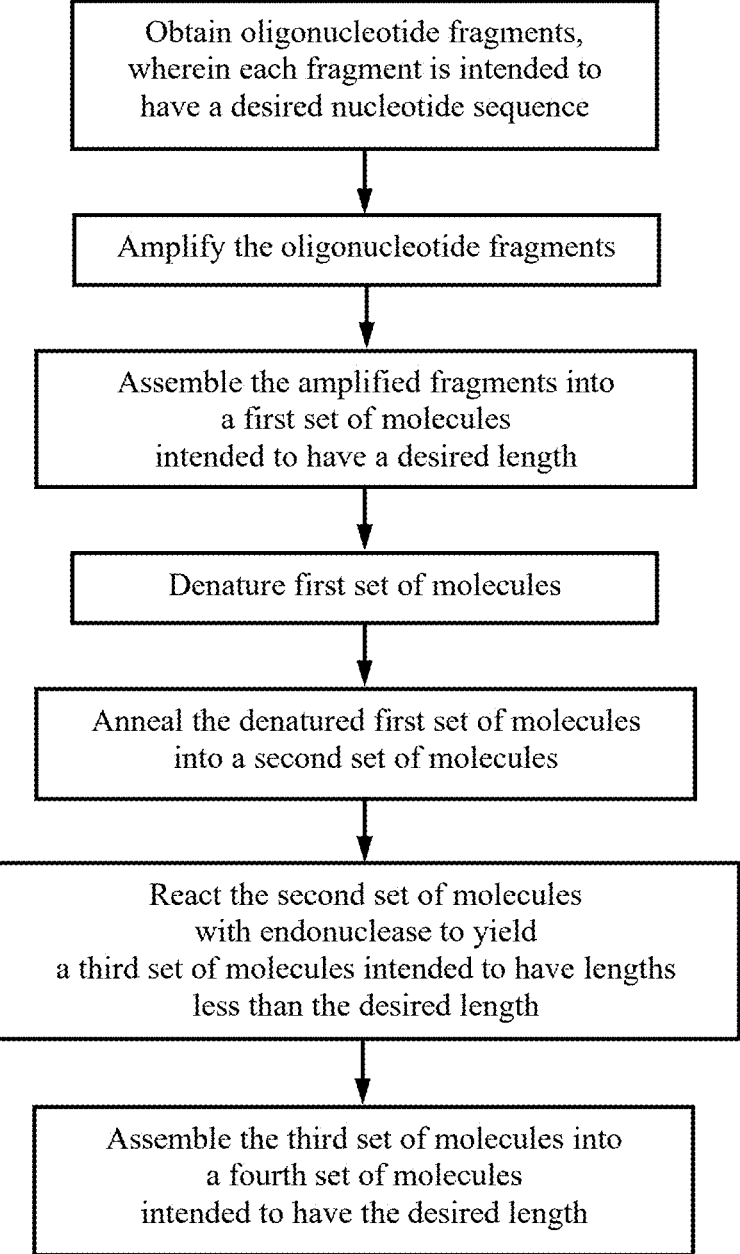
FIG. 6 is a flow chart of an exemplary process for synthesis of error-minimized nucleic acid molecules.

Another method of error correction is set out in FIG. 6. FIG. 6 is a flow chart of an exemplary process for synthesis of error-minimized nucleic acid molecules. In the first step, nucleic acid molecules of a length smaller than that of the full-length desired nucleotide sequence (i.e., "nucleic acid molecule fragments" of the full-length desired nucleotide sequence) are obtained. Each nucleic acid molecule is intended to have a desired nucleotide sequence that comprises a part of the full length desired nucleotide sequence. Each nucleic acid molecule may also be intended to have a desired nucleotide sequence that comprises an adapter primer for PCR amplification of the nucleic acid molecule, a tethering sequence for attachment of the nucleic acid molecule to a DNA microchip, or any other nucleotide sequence determined by any experimental purpose or other intention. The nucleic acid molecules may be obtained in any of one or more ways, for example, through synthesis, purchase, etc.

In the optional second step, the nucleic acid molecules are amplified to obtain more of each nucleic acid molecule. The amplification may be accomplished by any method, for example, by PCR. Introduction of additional errors into the nucleotide sequences of any of the nucleic acid molecules may occur during amplification.

In the third step, the amplified nucleic acid molecules are assembled into a first set of molecules intended to have a desired length, which may be the intended full length of the desired nucleotide sequence. Assembly of amplified nucleic acid molecules into full-length molecules may be accomplished in any way, for example, by using a PCR-based method.

In the fourth step, the first set of full-length molecules is denatured. Denaturation renders single-stranded molecules from double-stranded molecules. Denaturation may be accomplished by any means. In some embodiments, denaturation is accomplished by heating the molecules.

In the fifth step, the denatured molecules are annealed. Annealing renders a second set of full-length, double-stranded molecules from single-stranded molecules. Annealing may be accomplished by any means. In some embodiments, annealing is accomplished by cooling the molecules.

In the sixth step, the second set of full-length molecules are reacted with one or more endonucleases to yield a third set of molecules intended to have lengths less than the length of the complete desired gene sequence. The endonucleases cut one or more of the molecules in the second set into shorter molecules. The cuts may be accomplished by any means. Cuts at the sites of any nucleotide sequence errors are particularly desirable, in that assembly of pieces of one or more molecules that have been cut at error sites offers the possibility of removal of the cut errors in the final step of the process. In an exemplary embodiment, the molecules are cut with T7 endonuclease I, *E. coli* endonuclease V, and Mung Bean endonuclease in the presence of manganese. In this embodiment, the endonucleases are intended to introduce blunt cuts in the molecules at the sites of any sequence errors, as well as at random sites where there is no sequence error.

In the last step, the third set of molecules is assembled into a fourth set of molecules, whose length is intended to be the full length of the desired nucleotide sequence. Because of the late-stage error correction enabled by the provided method, the set of molecules is expected to have many fewer nucleotide sequence errors than can be provided by methods in the prior art.

The process set out above and in FIG. 6 is also set out in U.S. Pat. No. 7,704,690, the disclosure of which is incorporated herein by reference. Furthermore, the process described above may be encoded onto a computer-readable medium as processor-executable instructions.

Another process for effectuating error correction in chemically synthesized nucleic acid molecules is by a commercial process referred to as ERRASE™ (Novici Biotech). Error correction methods and reagent suitable for use in error correction processes are set out in U.S. Pat. Nos. 7,838,210 and 7,833,759, U.S. Patent Publication No. 2008/0145913 A1 (mismatch endonucleases), and PCT Publication WO 2011/102802 A1, the disclosures of which are incorporated herein by reference.

Exemplary mismatch endonucleases include endonuclease VII (encoded by the T4 gene 49), RES I endonuclease, CEL I endonuclease, and SP endonuclease or methyl-directed endonucleases such as MutH, MutS or MutL. The skilled person will recognize that other methods of error correction may be practiced in certain embodiments of the invention such as those described, for example, in U.S. Patent Publication Nos. 2006/0127920 AA, 2007/0231805 AA, 2010/0216648 A1, 2011/0124049 A1 or U.S. Pat. No. 7,820,412, the disclosures of which are incorporated herein by reference.

Figure 7:
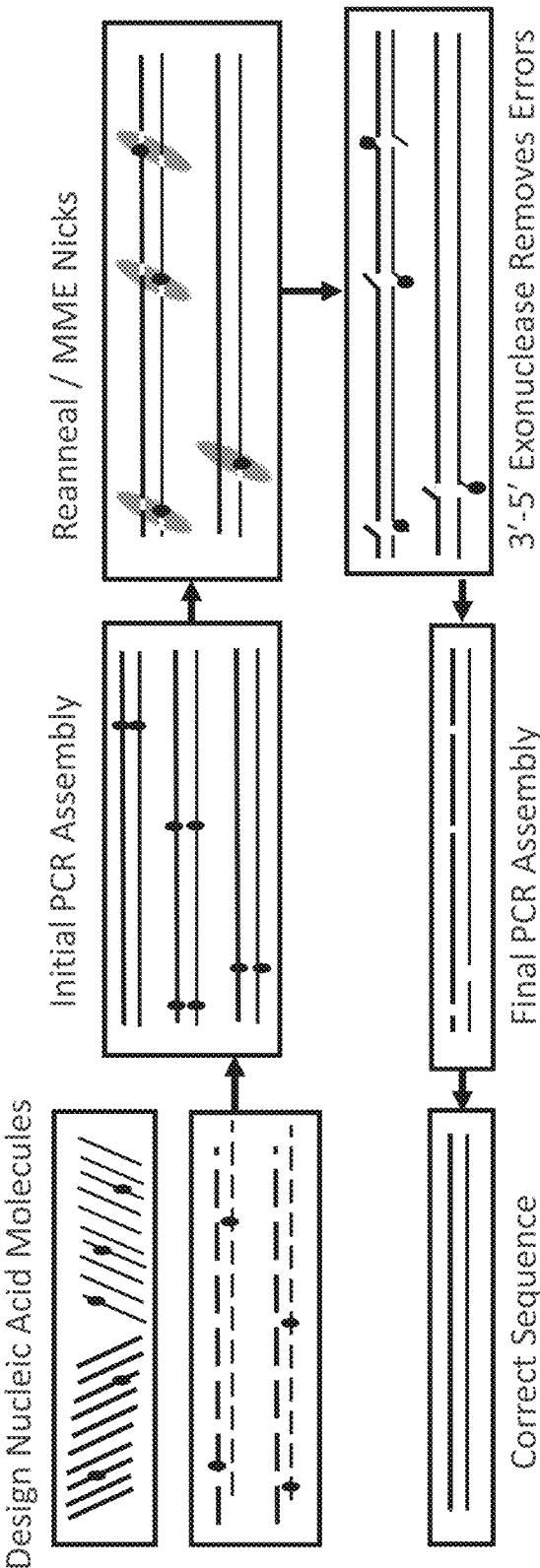
FIG. 7 is a work flow chart of an exemplary process for synthesis of error-minimized nucleic acid molecules. Different strands of a double-stranded nucleic acid molecule are represented by thicker and thinner line. "MME" refers to mis-match endonuclease. Small circles represent sequence errors.

Another schematic of an error correction method is shown in FIG. 7.

Synthetically generate nucleic acid molecules typically have error rate of about 1 base in 300-500 bases). Further, in many instances, greater than 80% of errors are single base frameshift deletions and insertions. Also, less than 2% of errors result from the action of polymerases when high fidelity PCR amplification is employed. In many instances, mismatch endonuclease (MME) correction will be performed using fixed protein:DNA ratio.

One error correction methods involves the following steps. The first step is to denature DNA contained in a reaction buffer (e.g., 200 mM Tris-HCl (pH 8.3), 250 mM KCl, 100 mM MgCl₂, 5 mM NAD, and 0.1% TRITON® X-100) at 98° C. for 2 minutes, followed by cooling to 4° C.

for 5 minutes, then warming the solution to 37° C. for 5 minutes, followed by storage at 4° C. At a later time, T7 endonuclease I and DNA ligase are added the solution 37° C. for 1 hour. The reaction is stopped by the addition EDTA. A similar process is set out in Huang et al., *Electrophoresis* 33:788-796 (2012).

Another method for removal of error from chemically synthesized nucleic acid molecules is by selection of nucleic acid molecules having correct nucleotide sequences. This may be done by the selection of a single nucleic acid molecule for amplification, then sequencing of the amplification products to determine if any errors are present. Thus, the invention also includes selection methods for the reduction of sequence errors. Methods for amplifying and sequence verifying nucleic acid molecules are set out in U.S. Pat. No. 8,173,368, the disclosure of which is incorporated herein by reference. Similar methods are set out in Matzas et al., *Nature Biotechnology,* 28:1291-1294 (2010).

Methods according to this aspect of the invention may include the following steps: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein.

According to various embodiments described herein, a computer-readable medium may be encoded with processor-executable instructions for: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein. In various embodiments, the computer-readable medium may be included in a system configured to reduce error from chemically synthesized nucleic acid molecules by selection of nucleic acid molecules having correct nucleotide sequences.

Large nucleic acid molecules are relatively fragile and, thus, shear, readily. One method for stabilizing such molecules is by maintaining them intracellularly. Thus, in some aspects, the invention involves the assembly and/or maintenance of large nucleic acid molecules in host cells.

One group of organisms known to perform homologous recombination fairly efficient is yeasts. Thus, host cells used in the practice of the invention may be yeast cells (e.g., *Saccharomyces cerevisiae, Schizosaccharomyces pombe, Pichia, pastoris,* etc.).

Yeast hosts are particularly suitable for manipulation of donor genomic material because of their unique set of genetic manipulation tools. The natural capacities of yeast cells, and decades of research have created a rich set of tools for manipulating DNA in yeast. These advantages are well known in the art. For example, yeast, with their rich genetic systems, can assemble and re-assemble nucleotide sequences by homologous recombination, a capability not shared by many readily available organisms. Yeast cells can be used to clone larger pieces of DNA, for example, entire cellular, organelle, and viral genomes that are not able to be cloned in other organisms. Thus, in some embodiments, the invention employs the enormous capacity of yeast genetics generate large nucleic acid molecules (e.g., synthetic genomics) by using yeast as host cells for assembly and maintenance.

Exemplary of the yeast host cells are yeast strain VL6-48N, developed for high transformation efficiency parent strain: VL6-48 (ATCC Number MYA-3666™)), the W303a strain, the MaV203 strain (Life Technologies Inc., cat. no. 11281-011), and recombination-deficient yeast strains, such as the RAD54 gene-deficient strain, VL6-48-Δ54G (MATa-his3-Δ200 trp1-Δ1 ura3-52 lys2 ade2-101 met14 rad54-Δ1:: kanMX), which can decrease the occurrence of a variety of recombination events in yeast artificial chromosomes (YACs).

There is a large set of selectable markers (e.g., URA3, HIS3, etc.) for selection and counter-selection of yeast mutants, making it possible to carry out multiple rounds of seamless nucleic acid alterations within yeast host cells. Thus, yeast can be used to introduce a number of different genetic modifications, including single nucleotide changes (e.g., insertions, deletions, mutations), modification of target nucleic acid portions and regions, and construction of entirely new chromosomes. Serial modifications to a cloned copy of an otherwise intractable genome or other large nucleic acid can be performed in yeast in rapid succession. The mating capacity of yeast is favorable for modifying genomes and other large nucleic acids. Yeast recombination machinery, when activated during yeast mating, can be used to generate libraries, e.g., combinatorial libraries containing variants of cloned genomes or nucleic acids.

For example, Yeast Artificial Chromosome (YAC) librar- ies have been constructed for several different bacteria (Azevedo et al., *PNAS USA* 90, 6047 (1993); Heuer et al., *Electrophoresis* 19, 486 (1998); Kuspa et al., *PNAS USA* 86, 8917 (1989). Large prokaryotic DNA segments can be cloned in yeast using the universal genetic code. Toxic gene expression typically is not a barrier to cloning nucleic acids in yeast. Studies with bacterial and archeal genomes, for example, indicate that because eukaryotes use different protein expression machinery than these bacteria, there is little risk of harm to yeast hosts by proteins expressed from the cloned genomes. Thus, the invention further includes methods for the generation of nucleic acid molecules (e.g., synthetic genomes) which confer a toxic phenotype when introduced into non-yeast cell (e.g., bacterial cells).

The transcription (Kozak, Gene 234, 187 (1999)) and translation (Kornberg, *Trends. Cell. Biol.* 9, M46 (1999) signals in yeast are different from those in bacteria. In fact, most prokaryotic genes likely are not expressed in yeast. There is no restriction barrier in yeast (Belfort and Roberts, *Nucleic Acids Res* 25, 3379 (1997). If there is a barrier, it may be a replication barrier, rather than a gene expression barrier (Stinchcomb et al., *PNAS USA* 77, 4559 (1980)). Gene toxicity is minimized because regulation of gene expression in a eukaryote such as yeast is different from that in prokaryotes. Also, Mycoplasmas, for example, use the codon UGA for tryptophan rather than as a translation stop signal. Thus, most *Mycoplasma* genes, if expressed, would produce truncated proteins in yeast. This largely avoids the possibility of toxic gene products.

Nucleic acid molecules may be assembled from natural or synthetic fragments together with yeast vectors prior to transformation into yeast cells or simultaneously co-transformed into yeast cells. New organisms may created by transferring these genomes or other nucleic acid molecules, which have been optionally manipulated as desired, into compatible recipient cells. Thus, one embodiment provides suitable techniques for transferring genomes and other nucleic acid molecules to yeast host cells, modifying the genomes within host cells while maintaining their stability and integrity, and transplanting the cloned and manipulated genomes from yeast host cells back into recipient cells that more closely resemble original donors (e.g., organisms from which the nucleotides sequences were obtained), thus cre- ating.

A commercially available product for the assembly of nucleic acid molecules in yeast cells is the GENEART® High-Order Genetic Assembly Systems (Life Technology, Cat. No. A13286). This is a kit for the simultaneous and seamless assembly of up to 10 DNA fragments, totaling up to 110 kilobases in length, into vectors. The system uses the ability of yeast to take up and recombine DNA fragments with high efficiency. This greatly reduces the in vitro han- dling of DNA and eliminates the need for enzymatic treat- ments, such as restriction and ligation, while allowing for precise fusions of DNA sequences. The kit contains mate- rials for the transformation and purification from yeast, including yeast selective media, and competent *E. coli* for plasmid amplification of correct clones.

Organisms other than yeast may be used for in vivo assembly. For example, it has been shown that exogenous DNA is integrated into homologous sequences in the genome of *Neurospora crassa* at a frequency of 100% in mutant strains deficient in non-homologous end joining. (Ninomiya et al., *Highly efficient gene replacements in Neurospora strains deficient for nonhomologous end-join- ing, PNAS,* 100:12248-12253 2004.) Thus, the invention further includes methods involving organisms other than yeast (e.g., fungi such as *N. crassa*) and methods which involve the suppression and/or elimination of non-homolo- gous end joining to increase the efficiency of homologous recombination. In essence, any cell which undergoes homologous recombination may be used to assemble nucleic acid molecules. However, cell most suitable for this aspect of the invention will be ones which naturally are efficient at performing homologous recombination (e.g., yeasts) or can be altered (e.g., through mutagenesis) to increase the fre- quency of which they homologous recombination.

Assembly and maintenance of nucleic acid molecules in will often involve either the generation of or the insertion into cells nucleic acid molecule which contain elements such as one or more origin of replication (e.g., two origins of replication which are functional in different cell types) and one or selection marker (e.g., one or more positive selection marker and/or one of more negative selection marker).

Nucleic acid molecules introduced into cells for assembly will normally have certain features which allow them to be assembled in a particular order. One feature is terminal sequence homology between nucleic acid molecules being assembled.

Assembled nucleic acid molecules may be introduced into other nucleic acid molecules located within a cell (e.g., a viral genome, a nuclear genome, an organelle genome, a bacterial chromosome, etc.). In such instances, functional elements such as origins of replication, centromeres, etc. will generally be present in the other nucleic acid molecules located within the cell. Thus, the invention provides, in part, compositions and methods relating to the assembly of nucleic acid molecules and the insertion of the resulting assembly into other nucleic acid molecules.

In some instances, standard ligase based joining of partially and fully assembled nucleic acid molecules may be employed. For example, fully assembled nucleic acid molecule may be generated with restriction enzyme sites near their termini. These nucleic acid molecules may then be treated with one of more suitably restrictions enzymes to generate, for example, either one or two "sticky ends". These sticky end molecules may then be introduced into a vector by standard restriction enzyme-ligase methods. In instances where the inert nucleic acid molecules have only one sticky end, ligases may be used for blunt end ligation of the "non-sticky" terminus.

Assembled nucleic acid molecules may also include functional elements which confer desirable properties (e.g., origins of replication, selectable markers, etc.). In many instances, the assembled nucleic acid molecules will be assembled from multiple individual nucleic acid segments with one of the segments being a vector (e.g., a linear vector).

Figure 8:
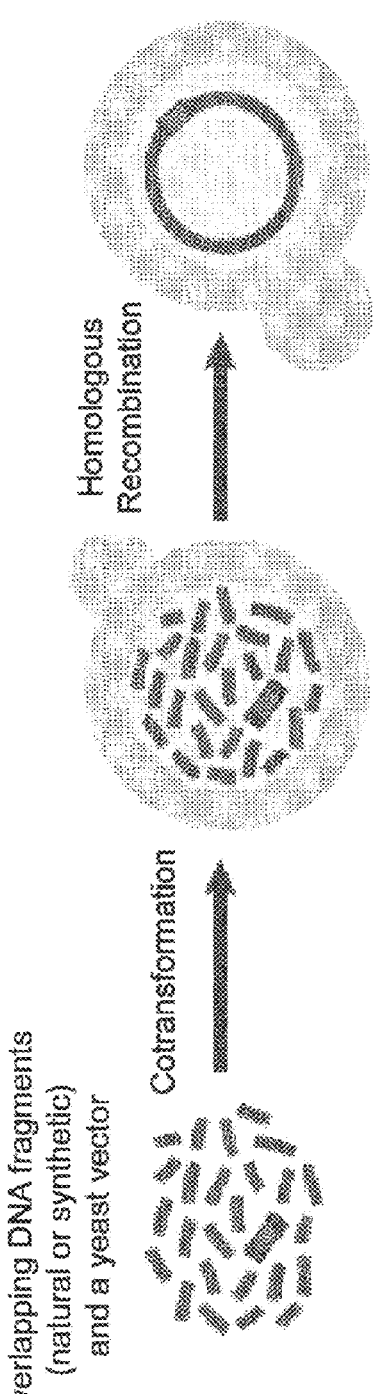
FIG. 8 generally illustrates methods for assembly and cloning of nucleic acid segments in yeast. In some embodiments of the invention, a number of nucleic acid segments (one of which is a vector) are co-transforming the fragments into a yeast host cell, where they are assembled by homologous recombination to form, for example, a closed, circular nucleic acid molecule.

Using the schematic of FIG. 8 for purposes of illustration, this approach may be carried out by co-transforming into the host cell, along with the host vector, a plurality (e.g., two, three, five, eight, ten, fifteen, twenty, thirty, etc.) of "overlapping" nucleic acid fragments for which assembly is desired. In this instance, each of the fragments contains are two regions of homology to regions of other nucleic acid segments introduced into the host cell. The nucleic acid segments after transformation into the host cell, for example by homologous recombination through regions of homology. In the instance shown in FIG. 8, the result is an assembled, closed circular nucleic acid molecule.

In one variation of the illustrative example shown in FIG. 8, overlapping fragments of a circular bacterial genome are co-transformed into a yeast host cell along with a linear yeast vector. Again, the yeast vector contains regions of homology at its termini to portions of the bacterial genome. Upon introduction of the genome fragments and yeast host vector into the host cell, the fragments and vector recombine, thereby joining the genome fragments and host vector.

The process shown in FIG. 8 relies, in part, on selection for the assembly of a closed, circular, replicable nucleic acid molecule. As similar selection mechanisms is set out in U.S. Patent Publication No. 2004/0219516 A1 (see, e.g., FIG. 20 of this application), the disclosure of which is incorporated herein by reference. Of course, nucleic acid molecules assembled by methods of the invention need not always generate a closed circular nucleic acid molecules. Other nucleic acid molecules which may be generated by methods of the invention include linear plasmids (e.g., plasmids which can replicate in linear form) and chromosomes.

In vivo assembly systems of the type shown in FIG. 8 may be composed of two core components: (1) Nucleic acid segments for assembly and (2) a suitable host cell. In certain embodiments where desired functional elements (e.g., origins of replication, selectable markers, etc.) are not represented in the nucleic acid segments for assembly, a vector may be included as an additional nucleic acid segment.

Fragments to be assembled will generally contain sequences that are overlapping at their termini. In one embodiment, the overlaps are approximately 10 bp; in other embodiments, the overlaps may be 15, 25, 50, 60, 70, 80 or 100 base pairs, etc. (e.g., from about 10 to about 120, from about 15 to about 120, from about 20 to about 120, from about 25 to about 120, from about 30 to about 120, from about 40 to about 120, from about 10 to about 40, from about 15 to about 50, from about 20 to about 50, etc. base pairs). In order to avoid misassembly, individual overlaps that should not be duplicated or closely match amongst the fragments. Since homologous recombination does not require 100% sequence identity between the participating nucleic acid molecules or regions, each terminus should be sufficiently different to prevent misassembly. Further, termini intended to undergo homologous recombination with each other should share at least 90%, 93%, 95%, or 98% sequence identity.

In in vivo assembly methods, a mixture of all of the fragments to be assembled is used to transfect the host recombination and assembly cell using standard transfection techniques. The ratio of the number of molecules of fragments in the mixture to the number of cells in the culture to be transfected should be high enough to permit at least some of the cells to take up more molecules of fragments than there are different fragments in the mixture. Thus, in most instances, the higher the efficiency of transfection, the larger number of cells will be present which contain all of the nucleic acid segments required to form the final desired assembled nucleic acid molecule. Technical parameters along these lines are set out in U.S. Patent Publication No. 2009/0275086 A1, the disclosure of which is incorporated herein by reference.

Figure 5:
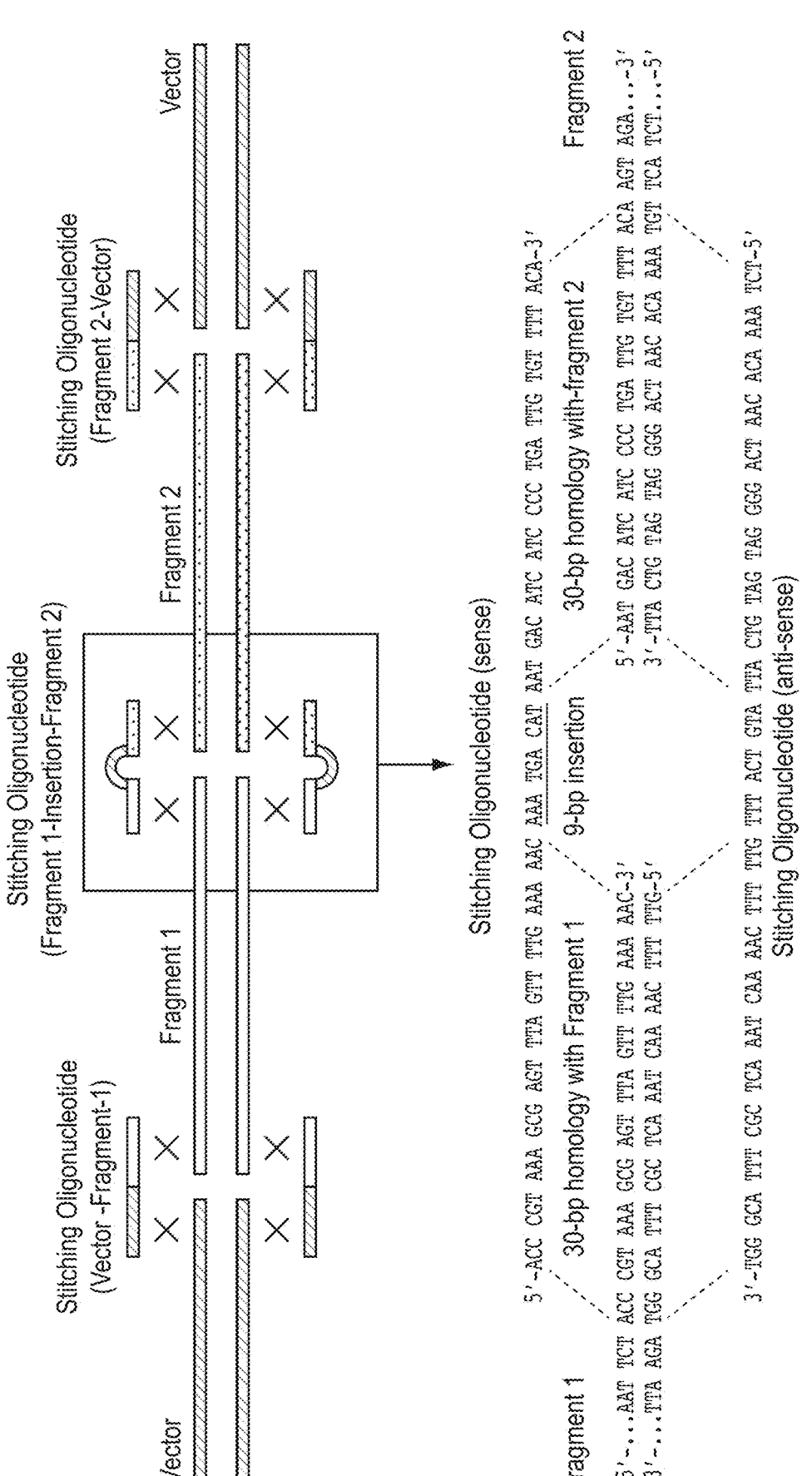
FIG. 5 shows the assembly of two DNA fragments that do not share any homology into a vector using stitching nucleic acid molecules. The 69 base pair double-stranded stitching nucleic acid molecules, shown in bold in the lower portion of the figure, share 30-bp homology with each adjacent fragment (Fragments 1 and 2). These stitching nucleic acid molecules are used to insert 9 bp at the junction of the adjacent fragments. The insertion bases are shown underlined.

One example of an assembly method which for joining double-stranded nucleic acid molecules which do not share terminal sequence homology is shown in FIG. 5. In this embodiment, two double-stranded fragments are introduced into a linear vector using singe-stranded "stitching nucleic acid molecules". In a sense, this is an assembling of five nucleic acid segments, wherein one of the segments is the vector, two of the segments are the two stitching nucleic acid molecules, and final two segments are the segments are labeled Fragment 1 and Fragment 2. In addition to facilitating the joining of other nucleic acid molecules, the stitching nucleic acid molecules introduced short insertion (e.g., nine base pairs) into the assembled nucleic acid molecule. A commercially available product which contains these features is the GENEART® High-Order Genetic Assembly Systems (Life Technology, Cat. No. A13286).

Nucleic acid molecules may also be assembled or otherwise designed with site specific recombination sites (e.g., GATEWAY® sites) and/or topoisomerase sites. Site specific recombinases are recombinase which typically have at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. (See Sauer, B., *Current Opinions in Biotechnology* 5:521-527 (1994)). Conservative site-specific recombination is distinguished from homologous recombination and transposition by a high degree of specificity for both partners. The strand exchange mechanism involves the cleavage and rejoining of specific nucleic acid sequences in the absence of DNA synthesis (Landy, A., *Ann. Rev. Biochem.* 58:913-949 (1989)).

One means by which nucleic acid molecules may be assembled is by the use of recombinational cloning. Thus, the invention includes compositions and methods related to recombination cloning and recombination sites, as well as recombination cloning components.

A number of recombinational cloning systems are known. Examples of recombination sites which may be sued in such systems include, but are not limited to, loxP sites; loxP site mutants, variants or derivatives such as loxP511 (see U.S. Pat. No. 5,851,808); frt sites; frt site mutants, variants or derivatives; dif sites; dif site mutants, variants or derivatives; psi sites; psi site mutants, variants or derivatives; cer sites; and cer site mutants, variants or derivatives.

These cloning systems are typically based upon the principle that particular recombination sites will recombine with their cognate counterparts. Nucleic acid molecules of the invention may be designed so as they contain recombination sites of different recombinational cloning systems (e.g., lox sites and att sites). As an example, a nucleic acid molecule of the invention may contain a single lox site and two att sites, wherein the att sites do not recombine with each other.

Recombination sites for use in the invention may be any nucleic acid that can serve as a substrate in a recombination reaction. Such recombination sites may be wild type or naturally occurring recombination sites, or modified, variant, derivative, or mutant recombination sites. Examples of recombination sites for use in the invention include, but are not limited to, phage lambda recombination sites (such as attP, attB, attL, and attR and mutants or derivatives thereof) and recombination sites from other bacteriophage such as phi80, P22, P2, 186, P4 and P1 (including lox sites such as loxP and loxP511). Mutated att sites (e.g., attB 1-10, attP 1-10, attR 1-10 and attL-1 10) are described in U.S. Appl. No. 60/136,744, filed May 28, 1999, and U.S. application Ser. No. 09/517,466, filed Mar. 2, 2000, which are specifically incorporated herein by reference. Other recombination sites having unique specificity (i.e., a first site will recombine with its corresponding site and will not recombine with a second site having a different specificity) are known to those skilled in the art and may be used to practice the present invention. Corresponding recombination proteins for these systems may be used in accordance with the invention with the indicated recombination sites. Other systems providing recombination sites and recombination proteins for use in the invention include the FLP/FRT system from *Saccharomyces cerevisiae*, the resolvase family (e.g., TndX, TnpX, Tn3 resolvase, Hin, Hjc, Gin, SpCCE1, ParA, and Cin), and IS231 and other *Bacillus thuringiensis* transposable elements. Other suitable recombination systems for use in the present invention include the XerC and XerD recombinases and the psi, dif and cer recombination sites in *Escherichia coli*. Other suitable recombination sites may be found in U.S. Pat. No. 5,851,808 issued to Elledge and Liu which is specifically incorporated herein by reference. Recombination proteins and mutant, modified, variant, or derivative recombination sites which may be used in the practice of the invention include those described in U.S. Pat. Nos. 5,888,732 and 6,143,557, and in U.S. application Ser. No. 09/438,358 (filed Nov. 12, 1999), based upon U.S. provisional application No. 60/108,324 (filed Nov. 13, 1998), and U.S. application Ser. No. 09/517,466 (filed Mar. 2, 2000), based upon U.S. provisional application No. 60/136,744 (filed May 28, 1999), as well as those associated with the GATEWAY® Cloning Technology available from Life Technologies Corp., (Carlsbad, Calif.), the entire disclosures of all of which are specifically incorporated herein by reference in their entireties.

Representative examples of recombination sites which can be used in the practice of the invention include att sites referred to above. Att sites which specifically recombine with other att sites can be constructed by altering nucleotides in and near the 7 base pair overlap region. Thus, recombination sites suitable for use in the methods, compositions, and vectors of the invention include, but are not limited to, those with insertions, deletions or substitutions of one, two, three, four, or more nucleotide bases within the 15 base pair core region (GCTTTTTTATACTAA (SEQ ID NO: 2)), which is identical in all four wild-type lambda att sites, attB, attP, attL and attR (see U.S. application Ser. No. 08/663,002, filed Jun. 7, 1996 (now U.S. Pat. No. 5,888,732) and Ser. No. 09/177,387, filed Oct. 23, 1998, which describes the core region in further detail, and the disclosures of which are incorporated herein by reference in their entireties). Recombination sites suitable for use in the methods, compositions, and vectors of the invention also include those with insertions, deletions or substitutions of one, two, three, four, or more nucleotide bases within the 15 base pair core region (GCTTTTTTATACTAA (SEQ ID NO: 2)) which are at least 50% identical, at least 55% identical, at least 60% identical, at least 65% identical, at least 70% identical, at least 75% identical, at least 80% identical, at least 85% identical, at least 90% identical, or at least 95% identical to this 15 base pair core region.

Analogously, the core regions in attB1, attP1, attL1 and attR1 are identical to one another, as are the core regions in attB2, attP2, attL2 and attR2. Nucleic acid molecules suitable for use with the invention also include those which comprising insertions, deletions or substitutions of one, two, three, four, or more nucleotides within the seven base pair overlap region (TTTATAC, which is defined by the cut sites for the integrase protein and is the region where strand exchange takes place) that occurs within this 15 base pair core region (GCTTTTTTATACTAA (SEQ ID NO: 2)).

Multi-Site GATEWAY® technology is described in U.S. Patent Publication No. 2004/0229229 A1, the entire disclosure of which is incorporated herein by reference, and is effective for cloning multiple DNA fragments into one vector without using restriction enzymes. This system can be used to link 1, 2, 3, 4, 5 or more nucleic acid segments, as well as to introduce such segments into vectors (e.g., a single vector). The GATEWAY® (e.g., Multi-Site GATEWAY®) system allows for combinations of different promoters, DNA elements, and genes to be studied in the same vector or plasmid, for efficient gene delivery and expression. Instead of transfecting multiple plasmids for each gene of interest, a single plasmid carrying different DNA elements, referred to as "an expression cassette" can be studied in the same genomic background.

The present invention also relates to methods of using one or more topoisomerases to generate assembled nucleic acid molecules. Topoisomerases may be used in combination with recombinational cloning techniques described herein. For example, a topoisomerase-mediated reaction may be used to attach one or more recombination sites to one or more nucleic acid segments. The segments may then be further manipulated and combined using, for example, recombinational cloning techniques.

In one aspect, the present invention provides methods for linking a first and at least a second nucleic acid segment topoisomerase (e.g., a type IA; type IB, such as Vaccinnia virus topoisomerase; and/or type II topoisomerase) such that either one or both strands of the linked segments are covalently joined at the site where the segments are linked.

A method for generating a double stranded recombinant nucleic acid molecule covalently linked in one strand can be performed by contacting a first nucleic acid molecule which has a site-specific topoisomerase recognition site (e.g., a type IA or a type II topoisomerase recognition site), or a cleavage product thereof, at a 5' or 3' terminus, with a second (or other) nucleic acid molecule, and optionally, a topoisomerase (e.g., a type IA, type IB, and/or type II topoisomerase), such that the second nucleotide sequence can be covalently attached to the first nucleotide sequence. As disclosed herein, methods of the invention can be performed using any number of nucleotide sequences, typically nucleic acid molecules wherein at least one of the nucleotide sequences has a site-specific topoisomerase recognition site (e.g., a type IA, type IB or type II topoisomerase), or cleavage product thereof, at one or both 5' and/or 3' termini.

Topoisomerase mediated nucleic acid ligation methods are described in detail in U.S. Patent Publ. No. 2004/0265863 A1, the entire disclosure of which is incorporated herein by reference.

Assembled nucleic acid molecules may be cloned may contain a blunt end to be linked, and the second nucleic acid molecule involved in the cloning method may contain an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

Any number of vectors may be used in the practice of the invention. Further, the selection of vectors for particular applications will vary with the specifics of those applications (e.g., the host cell). In many instances, vectors will be introduced into host cells in linear form.

Suitable vectors for use in the present invention also include prokaryotic vectors such as pcDNAII, pSL301, pSE280, pSE380, pSE420, pTrcHisA, B, and C, pRSET A, B, and C (Life Technologies Corp.), pGEMEX-1, and pGE-MEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Life Technologies Corp.) and variants and derivatives thereof. Other vectors of interest include eukaryotic expression vectors such as pFastBac, pFastBacHT, pFastBacDUAL, pSFV, and pTet-Splice (Life Technologies Corp.), pEUK-C1, pPUR, pMAM, pMAM-neo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Life Technologies Corp.) and variants or derivatives thereof.

Other vectors suitable for use in the invention include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (Qiagen), pBS vectors, PhageScript vectors, BlueScript vectors, pNH8A, pNH16A, pNH18A, pNH46A (Stratagene), pcDNA3 (Life Technologies Corp.), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Life Technologies Corp.) and variants or derivatives thereof.

Assembly methods, in addition to other methods described herein, are capable of being miniaturized and/or automated. In fact, in many instances, miniaturization will be desirable when the nucleic acid molecules being assembled and/or introduced into vectors are present in lower total numbers. One means by which micro-mixing can be accomplished for assembly and processes such as insertion of nucleic acid molecules into vectors is by electrowetting, for example, as described elsewhere herein.

Figure 16:
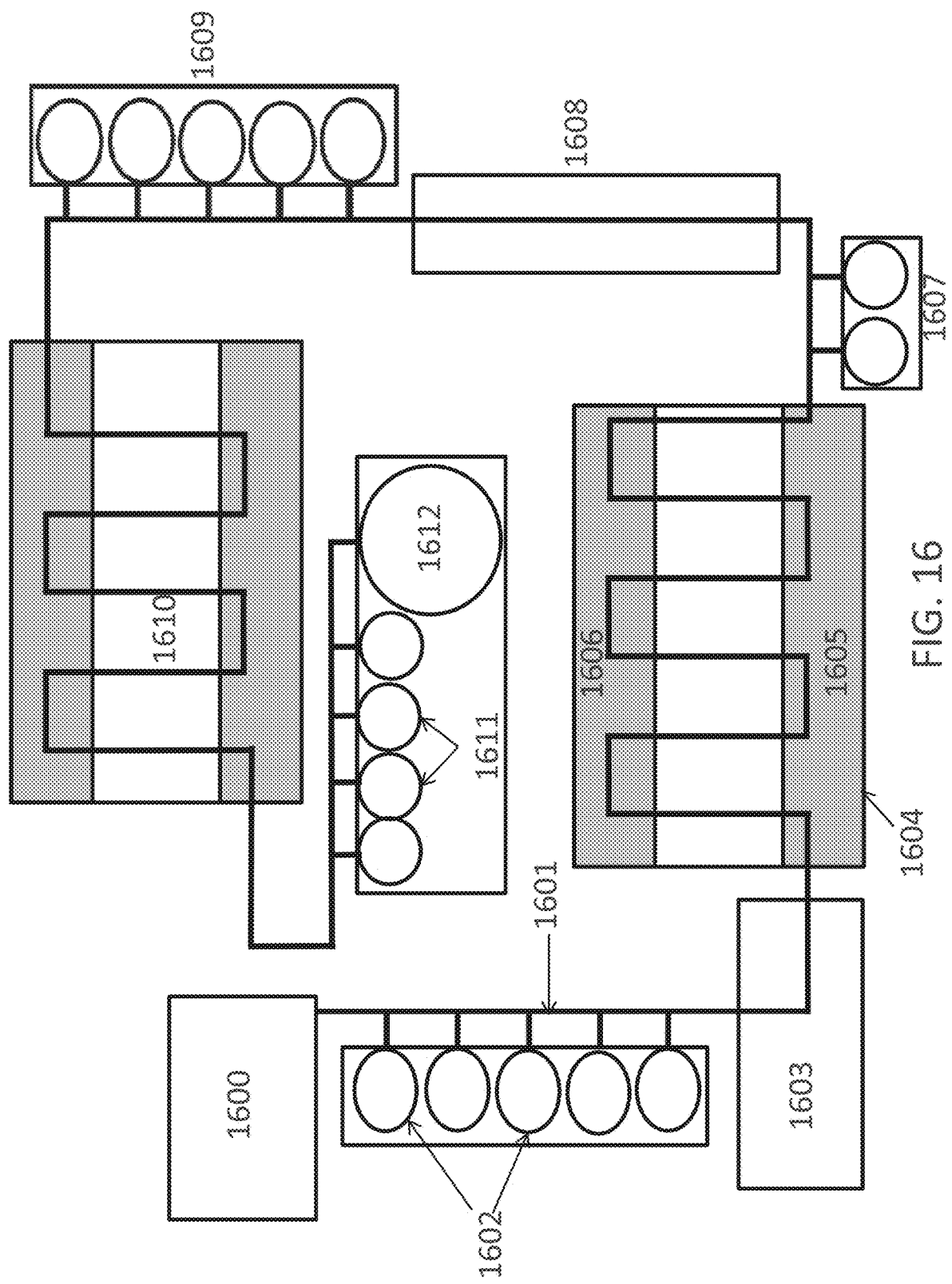
FIG. 16 is a schematic of automated system for performing methods of the invention.

FIG. 16 is a block diagram of one embodiment of an instrument for processing nucleic acid molecules of the invention. On the upper left of this figure is a carrier oil reservoir 1600 and a tube 1601 for transporting oil from this reservoir. Carrier oil is transported past a series of additional reservoirs 1602 that contain reagents. The circular structures represent individual reagents reservoirs. Exemplary reagents are nucleic acid molecules, PCR enzymes, primers, and vectors, as well as, for example, other Module 3 related components. The reagents will typically be in the form of aqueous vesicles transported between oil barriers.

The reagents transported by the carrier oil are then transported to a mixing chamber 1603 where mixing occurs. The reagents then move on to a digital PCR station 1604. The tube 1601 travels between a heating block 1605 where denaturation occurs followed by a cooling block 1606 where annealing and PCR occurs. Each time a vesicle travels to the cooling block 1606 after the first time, a PCR amplification occurs.

After exiting the digital PCR station 1604, the vesicles move past additional reagent reservoirs 1607 for the optional addition of more reagents, (e.g., buffers, error correction components, etc.), then on to another optional mixing chamber 1608. The vesicle then move on to an optional storage location 1609. In instances where more than one nucleic acid molecule is to be assembled into a larger molecule, the individual nucleic acid molecules for assembly will often arrive at the storage location 1609 at different times and will need to be sequestered for a period of time until other components arrive.

The nucleic acid molecules then move on to another digital PCR station 1610 and again cycle between cooling and heating blocks. Error correction reaction may occur in digital PCR station 1610. Finally, assembled nucleic acid molecules are transported to interface outlets 1611 for collection and waste materials (e.g., carrier oil) is collection in a waste reservoir 1612.

Systems of the type represented in FIG. 16 can process multiple samples at the same time. These samples can be sequestered between carrier oil and sent through the system in series. The FIG. 16 block diagram does not show a computer system, optical components, valves and other components related to system automation. Optical elements, as well as other elements (e.g., electrical elements) can be used to keep track of the location and identification of reagent vesicles and various points in the flow system. These reagent vesicles will generally contain nucleic acid molecules of a predetermined sequence. Thus, the invention include methods for the simultaneous processing (e.g., sequential processing) of multiple samples Module 4

Following isolation and treatment, the assembled nucleic acid molecules can be further transplanted into recipient cells using methods described herein or known in the art. Methods which may be used include protoplast and spheroplast fusion, conjugal transfer (e.g., bacterial conjugation), viral infection, electroporation and Sendai virus mediated cell fusion. Thus, the invention includes methods for transferring synthesized and/or assembled nucleic acid molecules to cells.

One method for generating yeast protoplast fusions in set out in Nakazawa and Iwano, *Efficient selection of hybrids by protoplast fusion using drug resistance markers and reporter genes in Saccharomyces cerevisiae, J. Biosci. Bioeng.* 98:353-358 (2004). Further, methods have been developed for the fusion or prokaryotic and eukaryotic cells. (See, e.g., Gyuris and Duda, *High-efficiency transformation of Saccharomyces cerevisiae cells by bacterial minicell protoplast fusion, Mol. Cell. Biol.* 6:3295-3297 (1986). Methods such as these may be used in the practice of the invention to transfer nucleic acid molecules between cells without exposing the nucleic acid molecules to an extracellular environment. Other methods which may be used include natural competence, biolistic gun, electroporation, Baculovirus mediated transduction, and Type III secretion systems.

An exemplary transplantation protocol is described in PCT Publication WO 2011/109031. One method used to transplant *Mycoplasma* genomes from donors to *Mycoplasma* recipients is described by Lartigue et al., Genome transplantation in bacteria: changing one species to another, *Science* 317:632 (2007). This work related to the complete replacement of the genome of a bacterial cell with a genome from another species by genome transplantation as naked DNA using polyethylene glycol-mediated transformation. The resulting recipient cells were phenotypically identical to the donor strain. Such methods can be used to transfer assembled nucleic acid molecules constructed by methods of the invention to recipient cells.

Recipient cells typically will be chosen based on their ability to support gene expression from the assembled nucleic acid molecules. For example, after a bacterial genome has been assembled in a eukaryotic host cell having a suitable genetic manipulation system (e.g., yeast), then it may be necessary or desirable to transplant the genome back into a bacterial recipient cell. Differences in translation and transcription and different codon usage, among other factors, can prevent expression of the donor gene products within the host cell. The recipient cell, therefore, may be of the same species or a similar species as a donor cell or organism. In many cases, the recipient cells will be of the same order or kingdom as the donor. However, in cases where expression in unrelated cell types is required, the initial gene design may include codon and sequence optimization strategies to allow for expression in different recipient cells.

Following isolation of donor nucleic acids in agarose plugs, host DNA can optionally be removed (e.g., by digest and/or electrophoresis), and optionally treated with methyl-transferases and/or proteinase.

Agarose plugs can be melted, for example, by incubation with β-Agarase I (New England Biolabs) as described in Example 3A(ii)(b) of PCT Publication WO 2011/109031.

Transplantation can be performed in the presence of polyethylene glycol (PEG), such as PEG-6000 or PEG-8000 or other PEG to facilitate transformation. The source, amount, and size of the PEG can be varied to determine the optimal PEG. In one example, the PEG is PEG-2000, PEG-40000 PEG-6000, PEG-8000, PEG-10000, PEG-20000, or other. The concentration of PEG can be varied depending upon the conditions of the transplantation; concentrations include those, for example, at or about 5% or at or about 10%. An example is described in Example 3A(ii)(c) of PCT Publication WO 2011/109031. Melted plugs can be added to the recipient cells in the presence of PEG with gentle rocking to mix. Cells are allowed to recover, centrifuged, and grown in medium containing appropriate selection medium to select for recipient cells containing the transplanted donor nucleic acid. In one aspect, cells are plated on the medium and grown under appropriate conditions for the recipient cell type until colonies appear. Colonies can be picked and further grown in selection medium to produce a desired quantity of recipient cells containing the transplanted genome or other donor nucleic acid.

A particular ratio of recipient cells to donor nucleic acid can be maintained as needed. In one example, a ratio of between at or about $10^7$ and at or about $10^8$ recipient cells per 2 µg genomic DNA can be maintained. The provided transplantation methods can be used to achieve approximately 30 transformants for 200 ng of endogenous genomic DNA, or between 500 and 1500 transplants per reaction, or other appropriate amount that is obtained from the host or donor cell. In one non-limiting example, transplantation is carried out with $10^7$ recipient cells, 20 picoliters of melted of agarose plug containing donor genome at 100 ng/µl. One would understand that the ratio of recipient cells to donor nucleic acid may vary depending upon the cell types and that empirical assessment can be used to optimize the ratio.

Selection of recipient cells which contain a transplanted donor nucleic acid can be performed by any number of means. For example, transplanted donor nucleic acid may contain a positive selection marker which will allows it to be maintained in recipient cells. Also, a counter-selectable marker may be introduced in the recipient cell genome to allow for selection against cells which retain these nucleic acid molecules. A combination of positive and counter selection can be employed if one desires an engineered recipient cell which contains a transplanted donor nucleic acid but not the original recipient cell genome.

Further, in some embodiment, a plurality (e.g., two, three, four, five, etc.) of donor nucleic acid molecules (e.g., genomes from different organisms), may be introduced into a single host cell. For example, a diploid yeast strain containing genomes of two different organisms, such as two *Mycoplasma* genomes from different species, can be generated by crossing two different haploid strains, each carrying one of the genomes. Crossing haploid yeast strains can be carried out using well-known methods.

Multiple distinct selection markers can be used in the respective haploid strains, to allow for selection of cells containing both genomes after the cross. For example, a HIS3 and TRP marker can be introduced into two different haploid cells, respectively, carrying different genomes, followed by selection of diploid cells on medium lacking histidine and tryptophan, as described in the Examples of PCT Publication WO 2011/109031.

Assembled nucleic acid molecules may be used for any number of purposes. For example, in many instances, it will be desirable to introduce such molecules into cells for particular applications. The components of the assembled nucleic acid molecules and the cells that they are introduced into will vary widely with the particular application.

One illustration of an application is a prokaryotic production cell line for which an assembled nucleic acid molecule represents the entire genome. This genome may be designed for minimal functionality with the following features represent/absent:

1. Lack of ability to undergo conjugation or mating (safety feature).
2. Lack of ability to synthesize a critical nutrient (safety feature).
3. Maintain a high energy charge (production efficiency feature).
4. A pathway for generation of a desired end product (production feature).

While features included or excluded from cells generated by methods of the invention can vary greatly, in many instances, safety features will be included to prevent "escape" of the organism and limit the ability of the organisms to transfer traits to other organisms. Production features may be included to tailor the organisms for a specific application. This tailoring may fine tuned in a manner not currently possible with a "chasis" organisms. A chasis organism is an organism which has many of the features the desired application but requires modification to make it fully suitable. Typically this modification results from (1) the inactivation of one or more gene and/or pathway and/or (2) the introduction of one or more gene. In some instances, assembled nucleic acid molecules may be introduced into a chasis organism with or without the ultimate elimination of the chasis organism genome.

A recipient cell can be, for example, a bacterial cell, a yeast cell, a fungal cell, an insect cell, a mammalian cell, a plant cell or an algal cell.

The invention includes methods for producing nucleic acid molecules (e.g., individual coding elements, genomes, etc.) designed to yield high level production of desired end products, as well as the nucleic acid molecules themselves and organisms into which these nucleic acid molecules are introduced. Using amino acid biosynthesis for purposes of illustration, many organisms can produce lysine on their own but do so in limited quantities. In many instances, L-aspartate is a starting compound for L-lysine production. Further, amino acids which may be produced as part of the conversion of aspartate to lysine include L-threonine, L-methionine and L-isoleucine. Further, a number of enzymes are involved in the conversion of aspartate to lysine, often starting with aspartate kinase. As would be apparent to one skilled in the art, pathways associated with the synthesis of L-lysine may also be altered for high level production of L-threonine, L-methionine and/or L-isoleucine. Enzymes involved in the production of L-lysine, L-threonine, L-methionine and L-isoleucine are set out in U.S. Pat. No. 7,323,321, the entire disclosure of which is incorporated herein by reference.

Pathway engineering can be employed to introduce constitutive, inducible and repressible promoters at specific points in the metabolic pathway to drive production towards a designed end product (e.g., L-lysine). Pathway engineering will often be employed in a manner that allows for the direction of cellular resources (e.g., energy charge, nutrients) of a cell to be directed to two functions: (1) Cell growth/division and (2) end product production. Thus, in some embodiments, the invention includes methods for designing and constructing cells, as well as the cells themselves, that channel cellular resources into two functions: (1) Cell growth/division and (2) end product production.

Cells of the invention may be designed to not engage in activities normally associated with wild-type cells. One of these activities is mating. Mating consumes cellular resources and facilitates gene transmission. In many instances, neither of these effects of mating will be desirable. Further, in some instances, mating leads to sporulation. Spore formatting may be desirable for storage of organisms but, in many instances, if sporulation is desired, then mating genes may be placed under tight regulatory control or instructed on vectors.

In some embodiments, the invention includes cells designed and constructed to have a minimal genome for the desired purpose. DNA replication, transcription, and translation, as examples, consume cellular resources. Thus, one method for providing for efficient cellular resource channeling is to design and/or use a cell with a minimal genome.

With respect to cell division, if basic molecules required for cellular function are decreased below certain levels, then cell growth and division will generally be impacted. Again using amino acid production for purposes of illustration, when lysine is the desired end product there are at least three choices for providing suitable concentrations of threonine, methionine and isoleucine for cellular metabolism: (1) Allowing for production of these amino acids by alternative pathways, (2) using promoters which allow for some production of these amino acids as side products of lysine production, and (3) supplying these amino acid exogenously.

The invention thus include methods for pathway engineering of cell, such methods comprising:

(a) synthesizing a plurality of nucleic acid molecules, wherein each nucleic acid molecule is prepared in a microquantity;

(b) joining some or all of the nucleic acid molecules present in the pool formed in (a) to form a plurality of larger nucleic acid molecules; and (c) assembling the plurality of larger nucleic acid molecules to form the nucleic acid molecule which encodes at least two expression products, wherein at least two of the at least two expression products are in the same biological pathway that converts a starting compound (e.g., L-aspartate) to a desired end product (e.g., L-lysine, L-isoleucine, etc.).

Various embodiments of the invention include computer-implemented methods for pathway engineering of cell. These methods may be implemented by a processor by executing instructions encoded on a computer-readable medium. According to various embodiments, the instructions may be for:

(a) synthesizing a plurality of nucleic acid molecules, wherein each nucleic acid molecule is prepared in a microquantity;

(b) joining some or all of the nucleic acid molecules present in the pool formed in (a) to form a plurality of larger nucleic acid molecules; and (c) assembling the plurality of larger nucleic acid molecules to form the nucleic acid molecule which encodes at least two expression products, wherein at least two of the at least two expression products are in the same biological pathway that converts a starting compound (e.g., L-aspartate) to a desired end product (e.g., L-lysine, L-isoleucine, etc.).

One application of technology of the invention is in biofuel production. In many instances, this involves the conversion of a carbon source to a biofuel or a biofuel precursor. Biofuel or biofuel precursors vary widely, as do cell suitable for their production. In many instances, cells used for the production of biofuel or biofuel precursors will be algal or plant cells. Exemplary algae which may be used in this and other aspects of the invention include *Anabaena* sp., *Chlamydomonas reinhardtii*, *Chlorella* sp., *Cyclotella* sp., *Gloeobacter violaceus*, *Nannochloropsis* sp., *Nodularia* sp., *Nostoc* sp., *Prochlorococcus* sp., *Synechococcus* sp., *Oscillatoria* sp., *Arthrospira* sp., *Lyngbya* sp., *Dunaliella* sp., and *Synechocystis* sp.

Many species of plants may be cultivated from a single or small number of plant cells. Thus, plants which contain assembled nucleic acid molecules in most, if not all of their cells, may be generated. Exemplary algae which may be used in this and other aspects of the invention include corn, soybeans, rapeseed, sugar cane, mustard, switchgrass, and jatropha.

Biofuels, biofuel precursors and related compounds produced applications may be useful for applications which include the following: space heating, lighting, cooking, and running of automobile engines and generators.

Exemplary biofuels and biofuel precursors include normal-chain alcohols (the alcohol group —OH attached to the terminal carbon) having greater than 3 carbon atoms up to 21 carbon on. Normal chain alcohols, which may be produced by methods of the invention, include n-butanol, n-pentanol, n-hexanol, n-heptanol, n-octanol (capryl alcohol), n-nonanol (pelargonic alcohol), n-decanol (capric alcohol), n-dodecanol (lauryl alcohol), n-pentadecanol, n-hexadecanol (cetyl alcohol), n-tetradecanol (myristyl alcohol), cis-9-hexadecen-1-ol (palmitoleyl alcohol), n-octadecanol (stearyl alcohol), 9E-octadecen-1-ol (elaidyl alcohol), cis-9-octadecen-1-ol (oleyl alcohol), 9Z, 12Z-octadecadien-1-ol (linoleyl alcohol), 9E, 12E-octadecadien-1-ol (elaidolinoleyl alcohol), 9Z, 12Z, 15Z-octadecatrien-1-ol (linolenyl alcohol), 9E, 12E, 15-E-octadecatrien-1-ol (elaidolinolenyl alcohol), 12-hydroxy-9-octadecen-1-ol (ricinoleyl alcohol) and 1-eicosanol (arachidyl alcohol or combinations thereof. Normal chain alcohols may be saturated or unsaturated.

n-butanol can be produced by microbial fermentation, chemically synthesized or obtained from a plant source by bacterial action (e.g., engineered bacterial generated by methods of the invention). This includes obtaining butanol from cellulose containing plants, lignin-containing plants, from sewage and animal waste, from sugars obtained from plant source and then by fermentation involving algae (e.g., engineered algae generated by methods of the invention). Higher alcohols can also be obtained in similar manner.

The invention may also be used to produce chemical intermediates. Example of such intermediates are 1,4-butanediol and 1,3-propanediol. 1,4-butanediol is a bifunctional alcohol with a broad array of uses in the chemical industry. As examples, butanediol and its derivatives are used in the production of plastics, polyurethanes, solvents, electronic chemicals and elastic fibers. A 1,4-butanediol synthesis pathway is set out in Burk, *International Sugar Journal* 112:30-35 (2010). Thus, the invention includes cells engineered to produce or for increased production of chemical intermediates (e.g., 1,4-butanediol, 1,3-propanediol, etc.), as well as methods for designing and producing such cells.

Additional Applications

As one skilled in the art would understand, nucleic acid molecules produced in microscale quantities (e.g., femtomoles to nanomoles quantities, such as from about 0.001 femptomole to about 1.0 nanomole, from about 0.01 femptomole to about 1.0 nanomole, from about 0.1 femptomole to about 1.0 nanomole, from about 0.001 femptomole to about 0.1 nanomole, from about 0.001 femptomole to about 0.01 nanomole, from about 0.001 femptomole to about 0.001 nanomole, from about 1.0 femptomole to about 1.0 nanomole, from about 1.0 femptomole to about 0.1 nanomole, from about 1.0 femptomole to about 0.01 nanomole, from about 1.0 femptomole to about 0.001 nanomole, from about 10 femtomoles to about 1.0 nanomole, from about 10 femtomoles to about 0.001 nanomole, from about 20 femtomoles to about 1.0 nanomole, from about 100 femtomoles to about 1.0 nanomole, from about 500 femtomoles to about 1.0 nanomole, from about 1 nanomole to about 800 nanomoles, from about 40 nanomoles to about 800 nanomoles, from about 100 nanomoles to about 800 nanomoles, from about 200 nanomoles to about 800 nanomoles, from about 500 nanomoles to about 800 nanomoles, from about 100 nanomoles to about 1,000 nanomoles, etc.).

The invention may be used to prepare microarrays. Such microarrays may be generated in multiple ways including by the depositing of nucleic acid molecules on a support (e.g., a solid support such as a planar sold support) or by synthesis of nucleic acid directly on the support. In one embodiment, the plate shown in FIGS. 2A-2B can be modified so that the base/bottom is designed for the synthesis of nucleic acid on its surface. Optionally, the base could be structured to be removable to yield, for example, a planar microarray. In most such instances, the bead shown in FIGS. 2A-2B would be omitted during nucleic acid synthesis. Thus, the invention includes methods for the generation of microarrays.

Methods for printing microarrays are set out in U.S. Pat. Nos. 5,807,522 and 7,211,148, the disclosure of which is incorporated herein by reference. Such methods may be used in the practice of the invention to produce, for example, microarrays by the deposition of nucleic acid molecules produced as described herein.

One advantage of methods described herein is their modularity. As an example, nucleic acid molecules which form sub-portions of different larger nucleic acid molecules may be produced on the same plate to array. Thus, methods of the invention allow for the simultaneous production of nucleic acid molecules, followed by selection of individual synthesized nucleic acid molecules for later processes (e.g., pooling, cleavage deprotection, and assembly). Thus, methods of the invention include those where nucleic acid molecules are simultaneously produced (e.g., chemically synthesized), followed by assembly into two or more (e.g., two to ten, three to ten, four to ten, five to ten, two to thirty, five to thirty, ten to thirty, five to fifty, etc.) larger nucleic acid molecules.

In certain embodiments, nucleic acid molecules or plurality of nucleic acid molecules synthesized by the methods of the present invention may be primers and/or probes. Primers and/or probes can be generated in microquantity using, for example, a solid support as described herein. Primers prime nucleic acid extension reactions that can be part of an amplification reaction. Probes are used to detect a target nucleic acid sequence. Accordingly, probes are used in detection methods to directly or indirectly detect a target nucleic acid sequence. Primers and probes typically have a predetermined nucleotide sequence that hybridize with or otherwise bind to a target nucleic acid sequence. Probes in illustrative embodiments include a label, such as a fluorescent label. For example, a control mechanism may be connected to a solid support or an array of solid supports used in the methods of the present invention, wherein a target nucleotide sequence is input into the control mechanism. The control mechanism may be used to direct the sequence of addition of reactants for nucleic acid synthesis, such that a nucleic acid molecule having the target nucleotide sequence is synthesized.

Probes and primers hybridize with or otherwise bind to a target nucleic acid sequence because of sequence identity they share with the target nucleic acid sequence. For example, a primer or probe can share 80, 85, 90, 95, 96, 97, 98, 99, 99.5, or 100% contiguous sequence identity with a target nucleic acid sequence. Primers and probes hybridize with their target nucleic acid sequence under stringent and typically highly stringent conditions, as are known in the art.

A label can be attached to the 5' terminal nucleotide, the 3' terminal nucleotide, or any internal nucleotide of the primers and/or probes of the present invention. The label in certain illustrative embodiments, is a fluorophore. A vast array of fluorophores are known to those of skill in the art and can be included in the methods and compositions of the present invention. See, for example, Cardullo et al, *Proc. Natl. Acad. Sci. USA* 85:8790-8794 (1988); Dexter, D. L, *J. of Chemical Physics* 21:836-850 (1953); Hochstrasser et al., *Biophysical Chemistry* 45:133-141 (1992); Selvin, R, *Methods in Enzymology* 246:300-334 (1995); Steinberg, I., *Ann. Rev. Biochem,* 40:83-114 (1971); Stryer, L., *Ann. Rev. Biochem,* 47:819-846 (1978); Wang et al., *Tetrahedron Letters* 31:6493-6496 (1990); Wang et al., *Anal. Chem.* 67:1197-1203 (1995). For example, the fluorophore can be Biosearch Blue, FAM, TET, a CAL Fluor dye, JOE, VIC, HEX, a Quasar dye, a Cy dye, NED, TAMRA, ROX, Texas Red, or a Pulsar dye. These dyes and nucleic acid synthesis reactants that include these dyes are commercially available, for example, from Biosearch Technologies, Inc., Glen Research, or Life Technologies.

In illustrative embodiments, primers synthesized by methods provided herein, are PCR primers. In certain embodiments, primers are labeled with a label on their 5' end or 3' end. For example, primers can be LUX primers, Scorpion primers, Amplifluor primers, and/or Plexor primers.

In certain embodiments, the present invention provides a method for synthesizing a plurality of primer and probe sets (e.g., pairs). The primer and probe sets (e.g., pairs) can be generated in microquantity using a plate described herein (e.g., a plate of the general format shown in FIGS. 2A-2B). A primer and probe set (e.g., pair) includes one or more primers that prime an extension reaction that generates a nucleic acid extension product that is a target nucleic acid sequence for one or more probes of the primer and probe set (e.g., pair). In other words, in a primer and probe set (e.g., pair), the probe typically binds to the amplification product generated by the primer(s). In illustrative embodiments, the primer and probe set (e.g., pair) include a pair of PCR primers and a probe that binds to an amplification product generated by an amplification reaction that uses the pair of primers. For example, the primer and probe set (e.g., pair) can include two PCR primers and one 5' nuclease probe or one Molecular Beacons probe that binds to the amplification product generated when the PCR primers are used in a PCR reaction.

As noted above, methods of the present invention can generate an array of nucleic acid molecules, such as primers, probes, and/or primer and probe sets (e.g., pairs). For example, nucleic acid molecules can be synthesized in an array of positions such that each position includes one or a plurality of nucleic acid molecules such as primers, probes, and/or primer and probe sets (e.g., pairs). Array can include primers, probes, and primer and probe sets (e.g., pairs) at a density of 100, 200, 250, 500, 1000, 10,000, 100,000, 1,000,000, or 10,000,000 per cm$^2$. The total number of nucleic acid molecules in an array of nucleic acid molecules generated using methods of the present invention can include, for example, 100, 200, 250, 500, 1000, 10,000, 100,000, 1,000,000, 10,000,000, 100,000,000, 1,000,000,000, or 10,000,000,000 primer, probes, and/or primer and probe sets (e.g., pairs). More than one primer and probe set (e.g., pair) can be included in an array position such that the primer and probe set (e.g., pair) are designed to perform a multiplex reaction, such as a multiplex PCR reaction.

Probes of the invention can be labeled with a single dye, such as a single fluorophore. Probes of the invention can be FISH probes.

Probes of the invention can be probes used in amplification reactions. For example, these probes can be dual-labeled probes. Dual-labeled probes in certain illustrative embodiments include labels that are donor-acceptor energy transfer pairs, such as FRET pairs. When the donor (fluorophore) is a component of a probe that utilizes donor-acceptor energy transfer, the donor fluorescent moiety and the quencher (acceptor) of the invention are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. In many instances, the efficiency of FRET between the donor and acceptor moieties is at least 10%, at least 50%, or at least 80%. The efficiency of FRET can easily be empirically tested using the methods both described herein and known in the art.

In some instances, the donor-acceptor pair may include a fluorophore and a quencher. The quencher can be a dark quencher. As such, probes of the present invention can include a BHQ dye or a DQ dye (Epoch) as the quencher. The quencher in other embodiments may be DABCYL or TAMRA.

Primers and probes synthesized using methods and systems of the present invention can include can include moieties that stabilize hybridization of nucleic acids (e.g., intercalators, minor groove binding moieties, bases modified with a stabilizing moiety (e.g., alkynyl moieties, and fluoroalkyl moieties)), and conformational stabilizing moieties, such as those disclosed in U.S. Patent Application Publication No. 2007/0059752, the disclosure of which is incorporated herein by reference. The primers and probes can include intercalating agents such as acridine. In other embodiment, primers and probes synthesized using methods and systems of the present invention can be locked nucleic acid (LNA) probes, or peptide nucleic acid (PNA) probes.

Dual-labeled probes synthesized using methods and systems of the present invention can be used in amplification reactions such as real-time PCR reactions. The dual-labeled probes in illustrative examples are hydrolysis probes, such as 5' nuclease probes (see e.g., Livak et al, *PCR Methods Appl.,* 4:357-562 (1995); and U.S. Pat. No. 5,538,848), molecular beacons (see e.g., Mhlanga, *Methods,* 25:463-472 (2001)), scorpions (see e.g., Saha, *J. Virol. Methods,* 93:33-42 (2001)), or hybridizing probes (see e.g., U.S. Pat. No. 7,670,832). In certain embodiments the primers and probes of the present invention are used in digital amplification reactions such as digital PCR reactions.

Primers synthesized by methods of the present invention can be between 5 and 50 nucleotides in length and are typically between 10 and 30 and more typically 15 and 30 nucleotides in length. Probes of the present invention can be between 5 and 100, 10 and 50, 10 and 30, or 15 and 30 nucleotides in length.

Methods of the present invention can utilize general chemistries and chemical methods known in the art for synthesizing nucleic acid molecules that include one, two, or more labels, such as a fluorescent labels. For example, such methods can utilize phosphoramidites and/or solid supports that are modified to include such labels. Exemplary solid supports, for example, can include at least one quencher bound through a linker to the solid support. Additional exemplary embodiments can utilize a solid support or a phosphoramidite functionalized moiety that stabilizes a duplex, triplex or higher order aggregation (e.g., hybridization) of a nucleic acid molecule synthesized according to the present invention with a target nucleic acid molecule.

In certain embodiments, the primers and/or probes of the present invention are used in real-time PCR assays such as gene expression assays or genotyping assays, for example SNP genpotyping assays. The probes can be generated using methods provided herein, at a concentration, for example, of between 1 nM and 1 M, 1 mM and 1 M. An exemplary concentration can be 100 mM. The probes and/or especially the primers generated by methods provided herein can be lyophilized. For example, 1-1,000,000 picomole of primer can be lyophilized in a reaction vessel, such as a tube, or a well, or can be dried on a spot of an array of positions.

In one embodiment, the present invention provides a method for nucleic acid synthesis that includes combining nucleic acid synthesis reactants inside a microwell and generating the nucleic acid molecule inside the microwell.

The microwell can be linked to a controller, such as a computer processor, wherein a nucleotide sequence for one or more nucleic acid molecules is input into the controller or otherwise present in a computer memory of the controller. The controller can be connected to or otherwise in communication with a nucleic acid molecule design and ordering functionality that can be provided over a wide-area network. For example, nucleic acid molecule design and ordering functionality can be provided over the Internet.

In certain embodiments, methods of the present invention include an HPLC-purification step. In addition, methods of the present invention can be performed under ISO and/or GMP-certified conditions. In some embodiment, nucleic acid molecule synthesis is performed using a microwell plate.

Methods and apparatus of the invention may also be used for the preparation of libraries. These libraries may contain one or more point mutations or highly divergent molecules (e.g., nucleic acid molecules which encode proteins with different functional activities). Along these lines, the invention includes methods for the generation of libraries where all or some of the library members are chemical synthesized and thus not generated from cellular nucleic acid. Library types which may be generated by methods of the invention include cDNA libraries, genomic libraries, combinatorial libraries, point mutation libraries, and combinations of one or more of such libraries.

Figure 11:
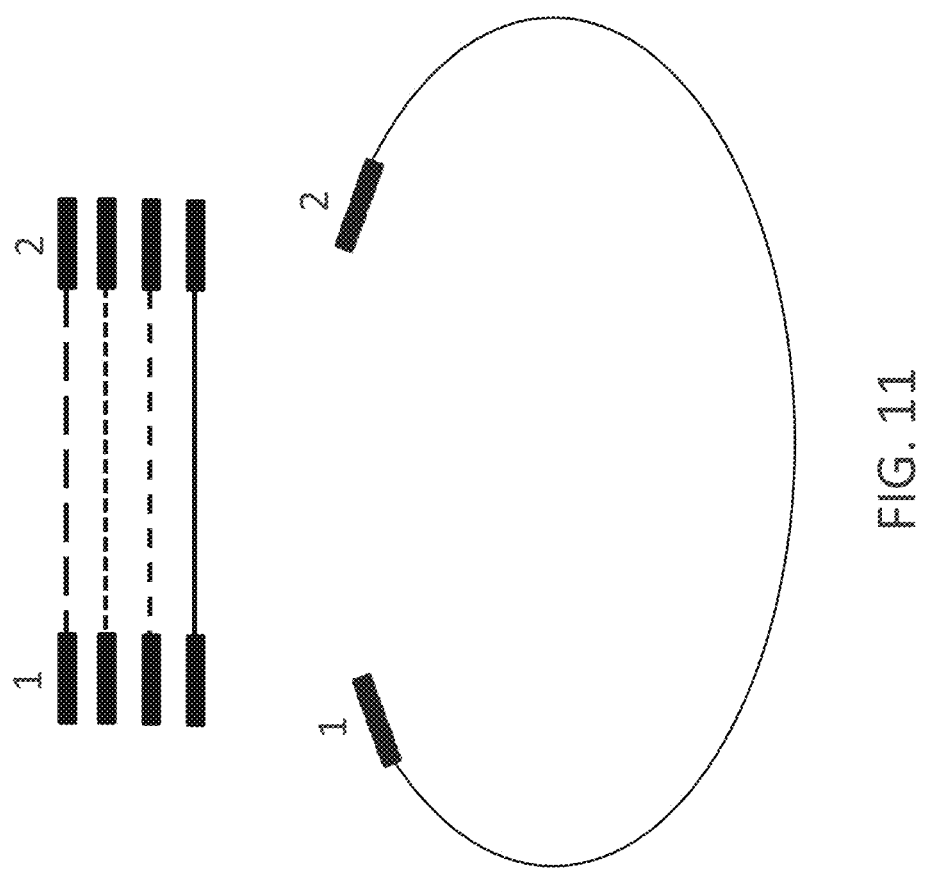
FIG. 11 shows a library of linear, nucleic acid molecules (top) generated by methods of the invention and a vector (bottom) designed to accept library members. The upper portion of the figure shows a series of lines representing four members of the library. The lower open circular line represents a vector. The blocks on each end of the nucleic acid molecule represent nucleic acid segments which facilitate joining (e.g., GATEWAY® sites, regions of homology, etc.). The numbers and the termini of the nucleic acid molecules indicate compatible ends.

As noted above, in some embodiments, the invention includes methods or producing cDNA library equivalents generated, as well as the libraries themselves, using bioinformatic information. Using the schematic shown in FIG. 11 for purposes of illustration, a library may be synthesized and, if necessary, assembled according to methods described herein. The library members may then be inserted into a non-library nucleic acid molecule (e.g., a vector, a cellular chromosome, etc.). Insertion may be facilitated by any number of means such as ligation (e.g., "sticky end" ligation).

The invention includes methods for generating library, as well as the libraries themselves. Some of these libraries are of types which are difficult or impossible to produce by standard library production methods. One such type is a partial cDNA library. Partial cDNA libraries (also referred to as "cDNA equivalent" libraries) may be generated by bioinformatically selecting specific cDNAs for inclusion in the library. Nucleic acid molecules may then be synthesized and, if necessary, assembled to form the library.

cDNA libraries typically contain DNA molecules which correspond to RNA transcripts within a cell. In many cases, such libraries are biased towards transcripts which contain polyA tails. mRNAs represented in such libraries typically contain multiple cDNAs corresponding to individual coding regions. This is true when splice variants of a genomics coding region are generated by splicing events. The present invention allows for the production of cDNA libraries (as well as genomic libraries) with "exclusive" representation. For example, since nucleic acid molecules are selected for inclusion, as compared to exclusion, the DNA molecules corresponding to the following may be excluded from libraries: ribosomal RNAs, globin RNAs, tRNAs, and specified mRNAs. Thus, the invention includes methods for producing member biased and exclusive member inclusion cDNA and genomic libraries, as well as the libraries themselves.

Further, libraries of the invention include those which contain specified nucleic acid molecules. For example, the invention includes methods for producing cDNA libraries containing a subset of member represented in cDNA libraries generated by standard methods. For purposes of illustration, assume that a particular mammalian cell type has on average 15,000 different mRNA transcripts including splice variants and one seeks to use a cDNA library which contains 125 cDNA molecules corresponding to all of the known splice variants of transcripts corresponding to 35 different kinases. In another instance, one seeks to screen a collection of nucleic acid molecules that encode variants of the same wild-type coding sequence. Using FIG. 12A for purposes of illustration, amino acids 85 through 95, and the coding sequence of a wild-type cDNA is shown at the top of the figure. Amino acids 88 through 91 represent a region which is predicted to be a flexible linker connecting two functional domains. In this instance, a collection of nucleic acid molecules is produced encoding proteins with different, but specified, amino acids at positions 88 through 91 (the linker region). Collections of nucleic acid molecules such as those shown in FIG. 12A may be generated in number of ways.

One way will generally be over inclusive in that additional nucleic acid molecules will normally be generated. This method employs "dirty bottle" synthesis. To generate variant molecules such as those shown in FIG. 12A reagents for the addition of bases at particular positions are mixed. Thus, when the base at the first and second positions of codon 88 are to be added, a mixture of reagents for addition of a C and G could be used. The ratio of these reagents may be adjusted to favor either C or G addition or the ratio may be adjusted so that equal amounts of C and G are introduced. In a portion of the population, the codon CGT (arginine) would also be generated.

Another method by which collections of nucleic acid molecules such as those shown in FIG. 12A may be generated is by synthesizing the individual variant sequences as separate nucleic acid segments. This allows for the generation of only nucleic acid molecules (except for synthesis errors) which encode the desired variant population members.

The invention also includes individual and collections of nucleic acid molecules with codon alterations as compared to wild-type molecules, as well as methods for producing such molecules. In some aspects, a codon altered library is generated where some or all (in many cases all or most) of the nucleic acid molecules in the collection are codon altered as compared to naturally wild-type coding sequences. This shows one substantial advantage of methods of the invention over standard library construction methods. With standard library construction methods, libraries are built from naturally occurring nucleic acid molecules (e.g., genomic DNA, mRNA, etc.). Methods of the invention allow for efficient construction of libraries using bioinformatic information. The result being that individual nucleic acid molecules in any collection generated can be generated with "tailored" nucleotide sequences.

Using FIG. 12B for purposes of illustration, a collection of nucleic acid molecules that contain different codons for the same coding sequence may be generated and then screened for desired features (e.g., increased or decreased expressions levels). Decreased expression levels may be desired when over expression of a protein is delirious to cells or host organisms that the protein is produced in. Thus, codon selection can be used as an expression regulation mechanism.

Methods of the invention may also be used to generate large numbers of primers for multiplex amplification (e.g., PCR). Typically such primers will be between 15 and 100 (e.g., from 15 to 90, from 25 to 90, from 25 to 80, from 25 to 70, from 25 to 60, from 25 to 50, from 30 to 90, from 30 to 60, etc.) nucleotides in length. Further, primers may also contain bar codes to allow for the tagging of amplified nucleic acid molecules for, for example, later identification as well as tracking of primers and primer pairs during and subsequent to synthesis runs.

In some instances, between 500 and 50,000, between 1,000 and 50,000, between 2,000 and 50,000, between 5,000 and 50,000, between 5,000 and 40,000, between 5,000 and 30,000, between 5,000 and 100,000, between 5,000 and 300,000, between 5,000 and 500,000, between 5,000 and 1,000,000, between 5,000 and 5,000,000, between 10,000 and 100,000, between 10,000 and 500,000, between 10,000 and 800,000, between 20,000 and 100,000, between 20,000 and 500,000, etc. primers pairs will be generated.

The invention includes the preparation of primers which may be used in processes such as Life Technology Corporation's AMPLISEQ™ products (see, e.g., cat. no. 4472395). Products such as this employ multiplex PCR for the amplification of specific nucleic acid molecules. The amplified nucleic acid molecules may then be used in downstream processes such as sequencing to identify nucleic acids present in a starting sample. In some cases, modified nucleic acid bases and/or natural bases not typically associated with DNA (e.g., deoxyuridine) are synthetically incorporated into the primer sequences as a "fifth (or greater) bottle" to impart particular properties into the individual primer(s) and/or primer set to facilitate downstream processing of the amplified products prior to sequencing or to further impart encoding of the individual primer(s) and/or primer set in the manner of barcoding to facilitate and resolve complex sequence analysis typically from a mixture of samples.

The invention thus provides methods for producing primer pools, as well as the primer pools themselves. Primer pools may be used to amplify RNA and/or DNA populations or subpopulation. As an example, primer pools may be produced that allow for the amplification of genomic DNA representing the entire nuclear genome of a cell, a single nuclear chromosome, a set of nuclear genes or regions (e.g., a set of chromosomal loci), a mitochondrial genome, or a chloroplast genome, as well as combinations thereof. The invention thus includes the bioinformatic design of primers for specific applications (e.g., the applications set out immediately above).

The invention also provides methods for producing primer pools for the amplification of specific RNA populations. In one embodiment of the invention, a primer pool is designed to amplify all mRNA molecules or a subpopulation of mRNA molecules (e.g., mRNAs encoding kinases, phosphatases, etc.) produced by a cell but, optionally, not other RNA molecules (e.g., tRNA, rRNA, hnRNA, etc.). Such primer pools may then be used for expression analysis (e.g., measuring the level of expression under various conditions). Expression analysis may be performed using, for example, microarrays or sequencing platforms. The invention thus includes expression analysis methods. In some embodiments, such methods include one or more of the following steps: (a) designing bioinformatically a primer pool, (b) synthesizing primer pairs of the primer pool, (c) contacting the primer pool to a sample derived from a cell containing nucleic acids (e.g., mRNA), (d) amplifying nucleic acid molecules in the sample corresponding to the primer pairs, and (e) analyzing the resulting amplified nucleic acid molecules.

The reduction or elimination of nucleic acid molecules corresponding to rDNA is desirable in many expression analysis applications because of the abundance of rRNA in many samples. Other rRNA amplification reduction methods are set out in U.S. Patent Publication No. 2008/0187969, the disclosure of which is incorporated herein by reference.

The invention also includes variations of the above for additional applications such as multiplex methods of the identification of mutations in genomic nucleic acid. Thus, the invention further includes methods and compositions for the identification of mutations, including cancer screens.

The invention includes methods for producing various numbers of primer (in many instances in primer pairs). The number of primers which may be prepared by methods of the invention as separate entities and/or in mixed populations range from five to 500,000, from 500 to 500,000, from 1,000 to 500,000, from 5,000 to 500,000, from 10,000 to 500,000, from 20,000 to 500,000, from 30,000 to 500,000, from 5,000 to 250,000, from 5,000 to 100,000, from five to 5,000, from five to 50,000, from 5,000 to 800,000, from 5,000 to 1,000,000, from 5,000 to 2,000,000, from 10,000 to 2,000,000, from 20,000 to 1,000,000, from 30,000 to 2,000,000, etc.

The invention thus provides methods for the rapid design, configuration and synthesis of defined sets of primers for the specifically determining genetic compositions and characterization of regions for a wide variety of analyses, sample sets and experimental designs. This aspect of the invention partially flows from the use of bioinformatics in conjunction with nucleic acid molecule synthesis methods described herein. In particular, the complete sequences of a considerable number of genomes have been sequenced. This sequence information, combined with nucleic acid synthesis methods (as well as other methods) described herein allow for detailed genome and transcriptome analyses. Multiplex methods, such as those set out above, provide one means for performing such analyses.

REPRESENTATIVE EMBODIMENTS

Numerous variations of the invention are feasible and may be employed to achieve the desired results. Many such variations may be directed to design features. In some instances, such design features may be used for operator convenience and/or cost savings (e.g., decreased reagent usage).

Figure 9:
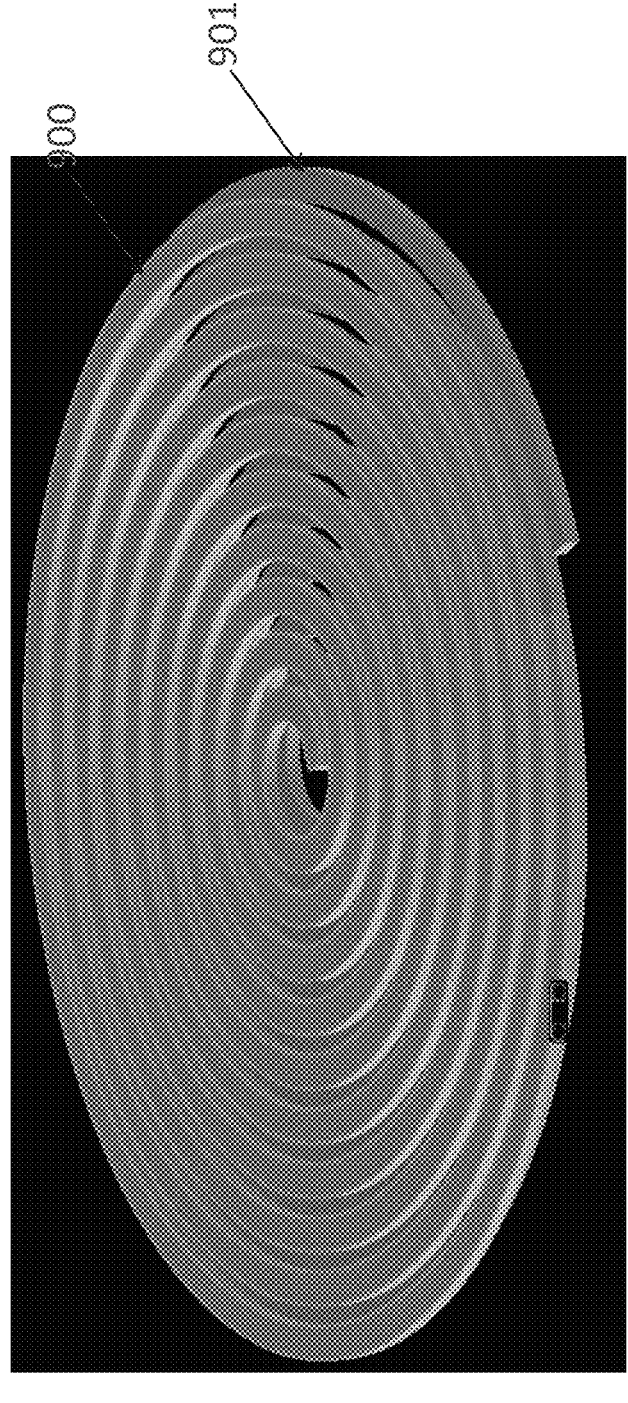
FIG. 9 is a drawing of an electrical coil that may be used in the practice of the invention.

FIG. 9 shows one embodiment of an electrical coil that may be used in specific embodiments of the invention. Numerous variations of such coils, a number of which are described elsewhere herein, may be used with the invention.

An electrical coil such as that shown in FIG. 9 may be designed with the following exemplary structural an operation parameters: Maximum current density 3 Amps/mm$^2$, double layer flat coil, wire cross section 5×2 μm, 10 turns, inner diameter (Di)~10 μm, outer diameter (Da)~180 μm, and wire length~6 mm

TABLE 6

| current (A) | Mag. Field Strength (A/m) (approx. short coil) |
| --- | --- |
| 0.00003 | 6.314390318 |

| current (μA) | Mag. Flux Density (T) |
| --- | --- |
| 30 | 7.9349E−06 |

FIG. 9 and TABLE 6 show exemplary specifications of a flat double layer coil that can be build up on a wafer. A coil such as that shown in FIG. 9 may be designed such that contact is made with each well in a synthesis platform. Further, the generation of a magnetic field may be used to lift beads from synthesis sites (e.g., wells). Exemplary magnetic field strength/flux density figures are shown in TABLE 6. A FEM-program like Comsol (www.comsol.com) may be used to calculate parameters for specific systems and formats.

Several materials, and properties associated with these materials, that may be used in electrodes used in various aspects of the invention are set out in TABLE 7. The selection of electrode materials will be determined by numerous factors including costs and various design specifications and power requirements.

TABLE 7

| Material | Specific Resistance (($\Omega$*mm$^2$)/m) | Coil Resistance ($\Omega$) | DC Power ($\mu$W) | Voltage (V) |
|---|---|---|---|---|
| Copper | 1.68E–02 | 10.068 | 0.009061 | 0.000302 |
| Aluminum | 2.65E–02 | 15.9 | 0.01431 | 0.000477 |
| Gold | 2.21E–02 | 13.284 | 0.011956 | 0.000399 |

Electrodes (e.g., electrical coils) used in the practice of the invention will be designed so as to meet the particular applications for which they are used. As an example, when electrodes are used to generate EGA, they will generally be designed with the following in mind: (1) The application (e.g., local application) of sufficient current to allow for the generation of an effective amount of EGA within a specified time period, (2) limitation of heating associated with the application of current. Thus, will generally be desirable to limit the amount of current used to reach a local pH of 1.0 with the addition of little excess current. TABLE 8 provides calculations for achieving this with specific well parameters. Further, the generation of pH 1 in a well as set out below will require that 727 pA of current be applied for about 1 second. This results in a current density of 115 A/m$^2$ on the working electrode.

TABLE 8

Current/pH generation for a cylindrical well using a 2.8 $\mu$m bead

| Input Parameter | | Input Parameter | |
|---|---|---|---|
| Well Diameter ($\mu$m) | 4 | Well Vol. ($\mu$m$^3$) | 37.68 |
| Well Height ($\mu$m) | 3 | Protons Generated | 4.52 $\times$ 10$^9$ |
| Desired pH | 1 | Charge (pAs) | 727 |
| Buffer Concen. (mol/L) | 0.1 | Current Density WE (A/m$^2$) | 115 |
| Area ($\mu$m$^2$) | 6.3 | | |

The shape of an electrode may vary greatly and may be a coil as shown in FIG. 9, a disk, a thin film, etc. Further, electrodes used in the practice of the invention may be composed of any number of compounds, including platinum, palladium, copper, gold, aluminum, niobium, niobium oxide, tungsten, titanium, tantalum, molybdenum, nickel, platinum, silver, manganese, neodymium, carbon, and silicon, and an alloy material or a compound material containing one or more of the above-described elements, as well as other elements.

Figure 10:
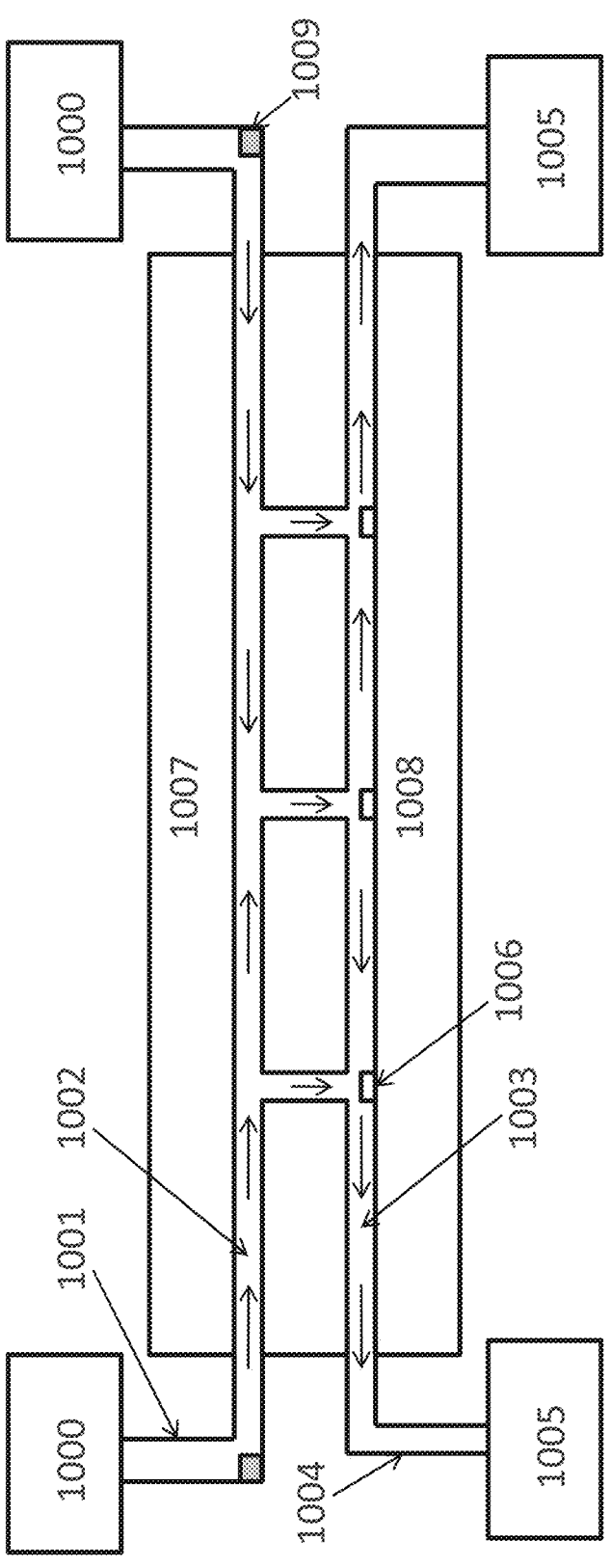
FIG. 10 is cross-sectional view of one embodiment of a fluid reagent delivery system suitable for use with the invention.

FIG. 10 shows an exemplary apparatus format of the invention. This figure shows two pumps 1000 that deliver fluids, as well as gases when appropriate, through tubes 1001 to fluidic channels 1002, which is bounded at the top by a plate 1007. Fluids delivered to the apparatus are removed through drainage channels 1003 to drainage tubes 1004 which lead to waste collection 1005. The pumps 1000 are connected to fluid reservoirs (not shown), or gas reservoirs when appropriate, and a control device (not shown) that regulate what fluid or gas is delivered to the apparatus.

The control device also regulates the length of time that fluids or gasses contact nucleic acid synthesis "chips" 1006. Three nucleic acid synthesis "chips" 1006 are visible in FIG. 10 resting on an electrode 1008. Fluids and/or gases are put in contact with the chips and current passes through particular locations on the chips where it is desirable for chemical reactions to occur. As described elsewhere herein, any number of reagents and washing materials may be used in the practice of the invention. In many instances, the reagents and materials used will be those which allow for the production of nucleic acid molecules.

The lower electrode 1008, as shown in FIG. 9, covers the entire base of the apparatus. This need not be the case and one or more electrodes may be associated with one end of each well or more than one well. Opposite this electrode (shown as a lower electrode 1008 in FIG. 10), there will typically be one or more second electrodes (not shown in FIG. 10) that allows for current to flow through entire chips or through wells of the chips. In many instances, these second electrodes will be positioned over individual wells of the chip to allow for current to be directed through the wells on an individual basis (see FIGS. 2A-2B).

Fluid channel 1002 can be formed in a surface layer. The surface layer can be formed of a polymeric material, inorganic material, or a combination thereof. For example, the surface layer can be formed of a polymeric material. An exemplary polymeric material includes acrylic, fluoropolymer, ethylene vinyl acetate (EVA), or any combination thereof. In an example, the polymeric material is a fluoropolymer. An exemplary fluoropolymer includes polyvinylidene fluoride (PVDF), polyvinyl fluoride (PVF), fluorinated ethylene propylene (FEP) copolymer, ethylene chlorotrifluoroethylene (ECTFE) copolymer, a copolymer of tetrafluoroethylene, hexafluoropropylene, and vinylidene fluoride (THV), a copolymer of tetrafluoroethylene and perfluoro methylvinylether (PFA or MFA), a fluoropolymer having a fluorinated oxolane in its backbone, perfluoroetheri, or any combination thereof. In particular, the fluoropolymer can be a fluoropolymer having fluorinated oxolane in its backbone, for example, Cytop. Further, the polymer coating can be amorphous, exhibiting little or no crystallinity. In another example, the surface layer is formed of an inorganic insulator. For example, the inorganic insulator can include an oxide of silicon, aluminum, hafnium, tantalum, zirconium, or any combination thereof, can include tetraorthosilicate, can include a nitride of silicon, or can include any combination thereof. In an example, the inorganic insulator can include an oxide of silicon. In another example, the inorganic insulator includes a nitride of silicon.

The surface layer can have a thickness in a range of 0.3 micrometers to 10 micrometers, such as a range of 0.5 micrometers to 6 micrometers.

Individual wells used in the practice of the invention may be of any number of shapes and sizes. One example of well parameters is set out in TABLE 9. Of course, well volume and other factors will change with well dimensions.

TABLE 9

| Exemplary cylindrical well parameters | | | |
|---|---|---|---|
| Input Parameter | | Output Parameter | |
| Well Diameter | 40 μm | Well Volume | 43,960 μm³ |
| Well Height | 35 μm | Generated Protons/ | $5.28 \times 10^{12}$ |
| pH | 1 | Well (incl. buffer) | |
| Buffer Concen. (mol/l) | 0.1 mol/l | Charge | 848 nAs |
| Area/Well | 1256 μm² | Current Density/ | 675 A/m² |
| | | Well | |

TABLE 10

| Input | | Output | |
|---|---|---|---|
| Number of Oligos/Bead | $1.0 \times 10^8$ | Required Buffer | 1,666,667 |
| Number of beads with | 1 | Vol. (pl) | |
| same oligo sequence | | | |
| Oligonucleotide | 0.10 | | |
| Concentration (μmol/l) | | | |
| Bead Diameter (μm) | 30 | Bead Vol. (μm³) | 14,137.17 |

TABLE 10 shows some bead parameters and estimate buffer volume and concentration for a particular bead size.

After completion of nucleic acid molecules production steps, the substrates (e.g., beads) containing the nucleic acid molecules may be collected, separated from the synthesis substrates, and further processed.

An exemplary work flow is one such as the following: (1) Beads are prepared with functional (hydroxyl or amine) groups, (2) the beads are derivatized in batch off-line forming amide with pre-synthesized universal primers with rare type IIs restriction site for enzymatic cleavage of synthesized nucleic acid molecules off the beads, (3) the beads are loaded by flowing suspension into chip, application of current secures beads in wells, (4) the loaded beads are in or near physical contact with an anode and EGA is generated at anode and on the bead surface for deprotection, (5) synthesis steps as described herein are performed, (6) after synthesis, digitally electro-eject of desired beads from well is accomplished by reversing the current, (7) ejected beads are collected and pooled from the liquid flow out of chip, and (8) other beads are held in wells until later in time by the application of weak current in initial anode/cathode orientation.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 15 is a block diagram that illustrates a computer system 1500 that may be employed to carry out processing functionality, according to various embodiments, upon which embodiments of a thermal cycler system 500 of FIG. 5 may utilize. Computing system 1500 can include one or more processors or controllers, such as a processor 1504. Processor 1504 can be implemented using a general or special purpose processing engine such as, for example, a microprocessor, controller or other control logic. In this example, processor 1504 is connected to a bus 1502 or other communication medium. For example, processor 1504 may be a current controller as described above with reference to FIGS. 2A-2B.

Further, it should be appreciated that a computing system 1500 of FIG. 12 may be embodied in any of a number of forms, such as a rack-mounted computer, mainframe, super-computer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 1500 may include bus 1502 or other communication mechanism for communicating information, and processor 1504 coupled with bus 1502 for processing information.

Computing system 1500 also includes a memory 1506, which can be a random access memory (RAM) or other dynamic memory, coupled to bus 1502 for storing instructions to be executed by processor 1504. Memory 1506 also may be used for storing temporary variables or other intermediate information during execution of instructions to be executed by processor 1504. Computing system 1500 further includes a read only memory (ROM) 1508 or other static storage device coupled to bus 1502 for storing static information and instructions for processor 1504.

Computing system 1500 may also include a non-transitory storage device 1510, such as a magnetic disk, optical disk, or solid state drive (SSD) is provided and coupled to bus 1502 for storing information and instructions. Storage device 1510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored there in particular computer software, instructions, or data.

In alternative embodiments, storage device 1510 may include other similar instrumentalities for allowing computer programs or other instructions or data to be loaded into computing system 1500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1510 to computing system 1500.

Computing system 1500 can also include a communications interface 1518. Communications interface 1518 can be used to allow software and data to be transferred between computing system 1500 and external devices. Examples of communications interface 1518 can include a modem, a network interface (such as an Ethernet or other NIC card), a communications port (such as for example, a USB port, a RS-232C serial port), a PCMCIA slot and card, Bluetooth, etc. Software and data transferred via communications interface 1518 are in the form of signals which can be electronic, electromagnetic, optical or other signals capable of being received by communications interface 1518. These signals may be transmitted and received by communications interface 1518 via a channel such as a wireless medium, wire or cable, fiber optics, or other communications medium. Some examples of a channel include a phone line, a cellular phone link, an RF link, a network interface, a local or wide area network, and other communications channels.

Computing system 1500 may be coupled via bus 1502 to a display 1512, such as a cathode ray tube (CRT) or liquid crystal display (LCD), for displaying information to a computer user. An input device 1514, including alphanumeric and other keys, is coupled to bus 1502 for communicating information and command selections to processor 1504, for example. An input device may also be a display, such as an LCD display, configured with touch screen input capabilities. Another type of user input device is cursor control 1516, such as a mouse, a trackball or cursor direction keys for communicating direction information and command selections to processor 1504 and for controlling cursor movement on display 1512. This input device typically has two degrees of freedom in two axes, a first axis (e.g., x) and a second axis (e.g., y), that allows the device to specify positions in a plane. A computing system 1500 provides data processing and provides a level of confidence for such data. Consistent with certain implementations of embodiments of the present teachings, data processing and confidence values are provided by computing system 1500 in response to processor 1504 executing one or more sequences of one or more instructions contained in memory 1506. Such instructions may be read into memory 1506 from another computer-readable medium, such as storage device 1510. Execution of the sequences of instructions contained in memory 1506 causes processor 1504 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1504 for execution. Such instructions, generally referred to as "computer program code" (which may be grouped in the form of computer programs or other groupings), when executed, enable the computing system 1500 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 1510. Volatile media includes dynamic memory, such as memory 1506. Transmission media includes coaxial cables, copper wire, and fiber optics, including the wires that comprise bus 1502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1504 for execution. For example, the instructions may initially be carried on magnetic disk of a remote computer. The remote computer can load the instructions into its dynamic memory and send the instructions over a telephone line using a modem. A modem local to computing system 1500 can receive the data on the telephone line and use an infra-red transmitter to convert the data to an infra-red signal. An infra-red detector coupled to bus 1502 can receive the data carried in the infra-red signal and place the data on bus 1502. Bus 1502 carries the data to memory 1506, from which processor 1504 retrieves and executes the instructions. The instructions received by memory 1506 may optionally be stored on storage device 1510 either before or after execution by processor 1504.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Oligonucleotide Synthesis Exemplary Embodiments

The following reagents are purchased and prepared for use in the oligonucleotide synthesis methods set out herein:

Amidite A: DMT-dA(bZ) Phosporamidite>99% (SIGMA Aldrich)

Amidite C: DMT-dC(bZ) Phosphoramidite>99% (SIGMA Aldrich)

Amidite G: DMT-dG(iB) Phosporamidite>99% (SIGMA Aldrich)

Amidite T: DMT-dT Phosphoramidite>99% (SIGMA Aldrich)

ACN: Acetonitrile for DNA synthesis<10 ppm water

Capping A: Cap A for DNA Synthesis (Acetic Anhydrid/Tetrahydrofuran 9.1/90.1) (SIGMA Aldrich)

Capping B: Cap B for DNA Synthesis (Tetrahydrofuran/N-Methylimidazole/Pyridine 8/1/1) (SIGMA Aldrich)

Oxidizer: Oxidizer (Tetrahydrofuran/Water/Pyridin/Iodine 77/2/21/2.52 (v/v/v/w)) (SIGMA Aldrich)

Activator: DCI activator configured for Perkin Elmer 8900 (Dicyanoimidazole/Acetonitril 3/100 (w/v)<30 ppm water) (SIGMA Aldrich)

Deblock (DEB): TCA-Deblock 3/100 (v/v)<200 ppm water (SIGMA Aldrich)

EGA: Electrochemical generated Acid: 5.5 g hydroquinone and 7.5 g tetraethyl ammonium p-toluene sulfonate is solubilized in 500 ml acetonitrile. The solution is electrochemically treated by a range of 14-20V until a pH 1-2 is reached, then adjust to pH 2.2 with acetonitrile. The solution is treated in an electrochemical cell where the anode and cathode compartment are separated by a Nafion membrane (Dupont, type N117, CAS Nr. 31175-20-9). A direct current by a range of 14-20V is applied until a pH 1-2 is reached in the anode compartment, then the electrolyte is adjusted to pH 2.2 with acetonitrile.

Oligonucleotide synthesis is performed by the steps set out below in Set-up: A synthesis package consisting of a bottom frit, solid support (60 nmol scale) mounted with a first base (corresponding to the 3'-end) and a top frit is provided.

Pre-processing: 40-110 µl ACN is dispensed onto the synthesis package, incubate for 15-20 sec. and ACN is removed. 40-110 µl of ACN is applied and immediately removed. 22-55 µl EGA is pipette onto the package, incubated for 22-30 sec. and then removed.

Synthesis cycles: (a) 22-55 µl of EGA is dispensed, incubated for 56-75 sec., then removed. This step is repeated once. Next, 40-110 µl of ACN is applied and removed without incubation. This step is repeated twice. 10-30 µl solution of Amidite/Activator (50/50) is dispensed and incubated for 50-60 sec., then removed. This step is repeated once. 40-110 µl ACN is pipette and removed. 10-35 µl CAP A/B (50/50) is dispensed and incubated for 30-40 sec., then removed. 40-110 µl ACN is applied without incubation and then removed. 20-50 µl Oxidizer is dispensed and incubated for 30-40 sec., then removed. 40-110 µl ACN is added, then immediately removed. 10-35 µl CAP A/B (50/50) is dispensed and incubated for 30-40 sec., this removed. (b)

50-110 µl is applied CAN, then removed without incubation. Steps (a) to (b) are repeated for each base to be added to the nascent oligonucleotide chain. After the final base is coupled, the following steps complete the synthesis process: 40-110 µl ACN is dispensed and then removed. 22-55 µl EGA is added, incubated for 53-70 sec., then removed. The EGA step is repeated once. 40-110 µl ACN is pipette, then removed without incubation. The ACN step is repeated once.

After the synthesis process was completed, a post processing of the oligonucleotides was done: The deprotection and cleavage of the oligonucleotides from the solid support was performed in an ammonia atmosphere at 80° C. applying pressure of at least 3 bar for 2 hours. Subsequently, the synthesis package was washed with ACN two times using 100 µl ACN. Finally, the oligonucleotides were eluted with 200 µl 10 mM TRIS buffer pH 7.5.

In order to determine the concentration of each oligonucleotide, the optical density (O.D.) is measured using a standard photometer at a wave length of 260 nm. Specification of the oligonucleotide concentration is required, in order to be able to prepare a mix of all oligonucleotides required for the synthesis of a given DNA fragment, so that each oligonucleotide has the same final concentration of 0.1 µmol in this mix.

TABLE 11

| | Sequence of Oligonucleotides | | |
|---|---|---|---|
| OligoSequence | | Coupling | SEQ ID NO: |
| AL1 | GAGGTACCGTCAATTTAATTAATTTTCAGGATGACGCGGAACTTGCCACACG | 51 | 3 |
| AL10 | TGAAATTCTTGGCTATTACAACAGACTGCCTTCAGATCTTAGCTTATGGCAAT | 52 | 4 |
| AL11 | CAAGAGAGCAAGCTCATCATTCTGGCCAGTGGTGGACCCCAAGCCTTAGTAAA | 52 | 5 |
| AL12 | CATAATGAGGACCTACACTTATGAGAAGCTTCTGTGGACCACAAGCAGAGTGC | 52 | 6 |
| AL13 | TGAAGGTGCTGTCTGTCTGCTCTAGCAACAAGCCGGCCATTGTAGAAGCTGGT | 52 | 7 |
| AL14 | GGGATGCAGGCACTGGGGCTTCATCTGACAGACCCAAGTCAGCGACTTGTTCA | 52 | 8 |
| AL15 | AAACTGTCTTTGGACTCTCAGAAACCTTTCAGATGCAGCGACTAAGCAGGAAG | 52 | 9 |
| AL16 | GGATGGAAGGCCTCCTTGGGACTCTAGTGCATTGTCTTCTTGGCGCGCCCAAC | 52 | 10 |
| AL2 | TGCAATTCCTGAGGCGACAAAAGCGCTAAACGATGAGGCCCAGGTGGTAGTT | 51 | 11 |
| AL3 | AATAAAGCTGCTGTTATGGTCCATCAGCTTTCCAAAAAGGAAGCTTCCAGAC | 51 | 12 |
| AL4 | ATGCCATCATGCGCTCCCCTCAGATGGTGTCTGCCATTGTACGCACCATGCA | 51 | 13 |
| AL5 | GAATACAAATGATGTAGAGACAGCTCGTTGTACTGCTGGGACTCTGCACAAC | 51 | 14 |
| AL6 | CTTTCTCACCACCGCGAGGGCTTGCTGGCCATCTTTAAGTCTGGTGGCATCC | 51 | 15 |
| AL7 | CAGCGCTGGTGAAAATGCTTGGGTCACCAGTGGATTCTGTACTGTTCTACGCC | 52 | 16 |
| AL8 | ATCACGACACTGCATAATCTCCTGCTCCATCAGGAAGGAGCTAAAATGGCAGT | 52 | 17 |
| AL9 | GCGCCTAGCTGGTGGACTGCAGAAAATGGTTGCTTTGCTCAACAAAACAAACG | 52 | 18 |
| Am1 | TCGCCTCAGGAATTGCACGTGTGGCAAGTTCCGC | 33 | 19 |
| Am10 | TGATGAGCTTGCTCTCTTGATTGCCATAAGCTAAGATCTG | 39 | 20 |
| Am11 | CATAAGTGTAGGTCCTCATTATGTTTACTAAGGCTTGGGGTCC | 42 | 21 |
| Am12 | CAGACAGACAGCACCTTCAGCACTCTGCTTGTGGTCC | 36 | 22 |
| Am13 | CCCAGTGCCTGCATCCCACCAGCTTCTACAATGGCC | 35 | 23 |
| Am14 | CTGAGAGTCCAAAGACAGTTTTGAACAAGTCGCTGACTTG | 39 | 24 |

TABLE 11-continued

| Sequence of Oligonucleotides | | | |
|---|---|---|---|
| OligoSequence | | Coupling | SEQ ID NO: |
| Am15 | CAAGGAGGCCTTCCATCCCTTCCTGCTTAGTCGCTG | 35 | 25 |
| Am2 | GGACCATAACAGCAGCTTTATTAACTACCACCTGGGCCTC | 39 | 26 |
| Am3 | GGAGCGCATGATGGCATGTCTGGAAGCTTCCTTTTTGG | 37 | 27 |
| Am4 | GCTGTCTCTACATCATTTGTATTCTGCATGGTGCGTACAATGG | 42 | 28 |
| Am5 | TCGCGGTGGTGAGAAAGGTTGTGCAGAGTCCCAGC | 34 | 29 |
| Am6 | GCATTTTCACCAGCGCTGGGATGCCACCAGACTTAAAG | 37 | 30 |
| Am7 | GAGATTATGCAGTGTCGTGATGGCGTAGAACAGTACAGAATC | 41 | 31 |
| Am8 | CCACCAGCTAGGCGCACTGCCATTTTAGCTCCTTC | 34 | 32 |
| Am9 | CTGTTGTAATAGCCAAGAATTTCACGTTTGTTTTGTTGAGCAAAG | 44 | 33 |
| Apb | GTCTTGTGCTCCAGGCGCGCCAAGAAGACAATGCACTA | 37 | 34 |
| Apf | CGTGTCTTGTCCAGGTACCGTCAATTTAATTAATTTTC | 37 | 35 |

Materials Used for Oligonucleotide Assembly

PCR master-mix (prepared freshly for 50 reactions): 1 ml H2O, 50 μl dNTPs (100 mM each), 250 μl 10× reaction buffer, 50 μl PAN Polymerase mix (PAN, Aidenbach, Germany) are mixed and spin down, then stored at 2-8° C.

TE buffer: 10 mM Tris/HCl, 1 mM ethylenediamine tetraacetic acid (EDTA), pH 8.

10× Loading Dye: 250 mg bromophenol blue (Merck, Darmstadt, Germany), 250 mg xylene cyanol (Merck), 58 ml glycerine (86%, Roth, Karlsruhe, Germany) in 42 ml H₂O is mixed and aliquoted.

Agarose gel running buffer: TAE buffer (40 mM Tris/HCl pH 8.0, 20 mM NaAc, 2 mM EDTA)

ZERO BLUNT™ TOPO PCR Cloning Kit (Life Technologies, Carlsbad, CA)

LB (Luria Bertani) medium: In 1 liter of H₂O, 10 g Bacto-trypton (Sigma-Aldrich, Deisenhofen, Germany), 5 g yeast extract (Sigma-Aldrich), 10 g NaCl, is mixed, adjusted to pH 7.0 with NaOH, autoclave and stored at 4° C.

Methods Used for Oligonucleotide Assembly

Oligonucleotide assembly. 5 μl of the oligonucleotide-pool containing all oligonucleotides of the oligonucleotide are mixed and adjusted to a final concentration of 15 nM, 18 μl H₂O and 27 μl PCR master-mix and subject to PCR using the protocol described in TABLE 11. For further amplification of the elongated oligonucleotides, 7 μl of the first PCR reaction is mixed with each 2 μl of the terminal amplification primer Apf and Apb (at a concentration of 15 μM, each), 27 μl PCR master-mix and 14 μl H₂O, and subjected to PCR using the protocol of TABLE 12.

Fragment analysis. An aliquot of the PCR reaction is mixed, usually ⅒th of the reaction volume, diluted in H₂O or TE if necessary, with 1 volume of Loading Dye per 9 volumes of purified DNA sample for gel analysis. The mixture is then loaded on a 1% agarose gel. The gel is run at a constant current and voltage (5V/cm2, 50V-150V) in TAE buffer.

Blunt cloning. 0.5-4 μl of the fresh PCR product is mixed with 1 μl of the pCR II-Blunt-TOPO and adjusted the volume to 6 μl with H2O, then incubated for 5 min at 22° C., then placed on ice.

Transformation. Competent *E. coli* (e.g., XL1-gold from Invitrogen Life Technologies, Carlsbad, CA) are transformed with the Blunt cloning mix. 100 μl of competent *E. coli* is thawed on ice, 2 μl of the Blunt cloning is added and mixed to the cells, then incubated for 20 min on ice. To apply a heat shock, the reaction tube is incubated for 60 sec at 42° C. using a water bath or a thermomixer (Thermomixer comfort, for 1.5 ml reaction tubes, Eppendorf, Hamburg, Germany) Immediately after the heat shock, the cells are put on ice for 5 min. If using ampicillin for selection, the cells are plated directly on ampicillin containing LB-plates (100 mg/l) and incubated at 37° C. overnight. For other selection agents (e.g., kanamycin or tetracycline), it is necessary to incubate the transformed bacteria with LB-medium without antibiotics for at least 30 min. at 37° C. in a shaker in order to provide time for recovery and expression of the respective resistance gene.

Colony picking. The required number of colonies are picked from the selection plate using a sterile tooth pick and perform a colony PCR (cPCR) using the PCR master mix and respective amplification primer (PCR protocol 2). The PCR product is analyzed on a 1% agarose gel as described to checked for the correct insert length.

Sequence analysis. The PCR products with the correct insert size are subjected to a sequencing reaction (e.g., using BIGDYE® Direct Cycle Sequencing Kit and a Genetic Analyzer from Invitrogen), according to the manufacturer's instructions, and the sequencing results are compared with the original oligonucleotide sequence to evaluate error classes and error rates.

TABLE 11

| PCR Protocol 1 | | | | |
|---|---|---|---|---|
| Cycle | Number | Step | ° C. | Time |
| 1 | 1 | 1 | 95 | 04:00 |
| 2 | 30 | 1 | 95 | 00:30 |
| | | 2 | 60 →40* | 00:30 |
| | | 3 | 72 | 01:00 |

TABLE 11-continued

| PCR Protocol 1 | | | | |
|---|---|---|---|---|
| Cycle | Number | Step | ° C. | Time |
| 3 | 1 | 1 | 72 | 04:00 |
| 4 | 1 | 1 | 4 | ∞ |

*use a touch down program

TABLE 12

| PCR Protocol 2 | | | | |
|---|---|---|---|---|
| Cycle | Number | Step | ° C. | Time |
| 1 | 1 | 1 | 95 | 04:00 |
| 2 | 30 | 1 | 95 | 00:30 |
| | | 2 | 58 | 00:30 |
| | | 3 | 72 | 01:00 |
| 3 | 1 | 1 | 72 | 04:00 |
| 4 | 1 | 1 | 4 | ∞ |

Experimental Description and Results

Experiment 1

The oligonucleotide with the nucleotide sequences set shown in TABLE 13 are synthesized twice, one set using DEB as a deblocking reagent the other set using EGA, as described. With each deblocking reagent two fragment sets have been synthesized. The detailed sequences of the oligonucleotides are shown in TABLE 13.

Figure 23:
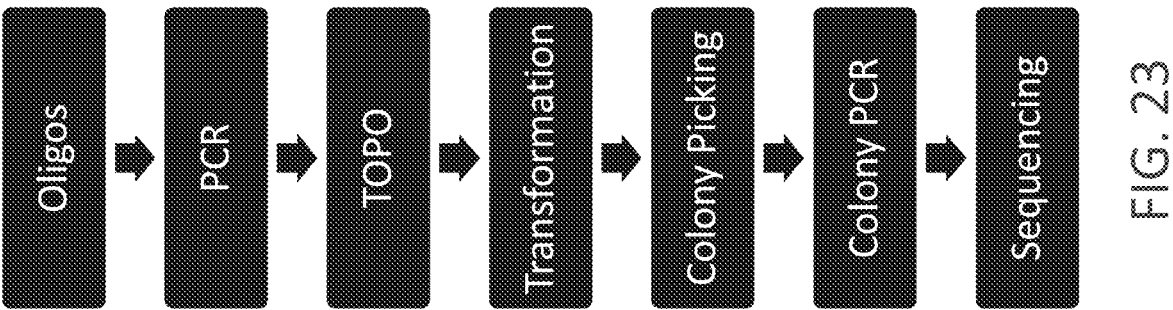
FIG. 23 shows a graphical overview of the gene synthesis work flow. The first step of this process is an ordered, sequence-determined self-assembly of the oligonucleotides to build the desired DNA fragment. The subsequent PCR reaction amplifies and links the individual oligonucleotides to yield a coherent double stranded DNA fragment. The resulting DNA fragment is cloned into a vector using standard cloning methods. Following transformation into *E. coli*, typically eight of the grown bacterial colonies are picked and analyzed for correctness, regarding the sequence of contained inserts. The sequence results are analyzed manually and the nature and number of occurring sequence errors is determined. For a reference regarding standard gene synthesis see NOTKA F., WAGNER R. (2012) Reprogramming a GFP Reporter Gene Subjects It to Complex Lentiviral Gene Regulation. Methods Mol Biol. 2012; 813:85-106. This workflow may also include an error correction step. Typically, error correction would be performed before, as part of, or after the first PCR step.

After determination of the concentration the oligonucleotides are pooled as described. Oligonucleotide mixes contain oligonucleotides from the synthesis with DEB except for one oligonucleotide, that is produced using EGA. Eight different oligonucleotide mixes are been prepared and analysed. For each oligonucleotide set a different EGA-originated oligonucleotide is replaced. The oligonucleotides Am1 (2×), Am3, Am5, Am8 (3×), Am13 are replaced. The oligonucleotide set are assembled as described in FIG. 23 and the sequence is analyzed. In total, sequence information derived from 49 colonies is evaluated. All oligonucleotide regions that corresponded to the EGA derived oligonucleotide have the correct sequences. From 1715 sequenced bases no errors are detected.

Experiment 2

In this experiment oligonucleotide sets (see TABLE 11 for the sequence information) are synthesized with the described process. For all sets, EGA is used as the deblocking reagent using the described standard oligonucleotide synthesis process. The average oligonucleotide concentration is 49.21 μM.

After cloning and transformation of the assembled oligonucleotides, assembled nucleic acid molecules from 5 colonies are analyzed by sequencing. The error rate (detected errors/1000 base pairs) of the synthesized oligonucleotides is as follows. A total of 16 insertions, 1.7 deletions and 1.2 substitutions per 1000 bp are detected.

Oligonucleotide Stitching Assembly (OSA) Exemplary Embodiments

A series of OSA reactions were performed to identify operational parameters of assembly methods. The resulting data is set out in FIG. 20 and in tables below.

Cell extracts for use if OSA methods were prepared as follows: DH10B *E. coli* strain (Life Technologies) was grown overnight at 37° C. in 5 ml LB media. Two ml of the overnight culture was then transferred to 100 ml fresh LB media and then grown at 37° C. until the $OD_{600\ nm}$ reached approximately 0.6. The cells were harvested by centrifugation at 5000×g for 20 minutes at 4° C. Cell pellets (~0.92 g wet weight) were washed once with 200 ml deionized $H_2O$ and then resuspended into 1.2 ml CELLYTIC™ B Cell Lysis Reagent (Sigma Chemical Co.), followed by incubation for 10 minutes at room temperature. The cell suspension was centrifuged at 20,000×g for 2 min. at room temperature and the supernatant was transferred to a 1.5 ml micrcentrifuge tube. The cell extract was then mixed with equal volume of 100% glycerol. Aliquots of ~50 μl cell lysate were stored at −80° C. in 50% glycerol.

The OSA protocol was as follows: The reaction mixture components were added to a 1.5 ml tube in the order set out below in TABLE 14, then the final reaction mixture was mixed well and incubated at room temperature for 30 min (additional time point at 45 min for precloned fragment). Four μl was used for transformation into TOP10 chemically competent cells and 50 to 100 μl of cells were plated on corresponding LB agar selection plates. Transformation conditions were as follows: An aliquot from the assembly reaction and cells were mixed and incubate on ice for at least 5 min, then heat shocked at 42° C. for 30 sec. The transformation reaction was placed on ice and at least 250 μl of SOC medium was added. Cells were allowed to recover on a shaker for 1 hour at 37° C.

pUC19 derivatives (AmpR vectors) were mainly used. Inserts were either (1) digested from existing vectors harboring an antibiotic resistance marker other than AmpR (e.g., Kanamycin, Spectinomycin) or (2) PCR amplified using a template lacking an AmpR marker. Data was generate using inserts ranging from 500 bp up to several kb in length.

TABLE 14

| Exemplary OSA Reaction Mixture | |
|---|---|
| 100 ng PCR-amplified vector (2.3 kb) | x |
| inserts (molar ratio of inserts to vector = 2:1) | y |
| 5× reaction buffer | 4 μl |
| stitching oligos (0.4 μM) | 1 μl |
| H₂O (up to 17 μl total) | (12-x-y) μl |
| Mix well | |
| Extract | 1 μl |
| 10× Enzyme Mixture | 2 μl |
| Total Volume | 20 μl |

TABLE 15 shows the composition of reagents used in used in the OSA reactions set out herein.

TABLE 15

| 10× Enzyme Mix | | 5× Buffer Mix | |
|---|---|---|---|
| T7exo | 0.3 U/μl | Tris pH 7.5 | 100 mM |
| T4 Gene 32 Protein | 5 μg/μl | NaCl | 125 mM |
| BSA | 5 mg/ml | MgCl2 | 50 mM |
| Tris pH8 | 20 mM | PEG-8000 | 25% |
| NaCl | 60 mM | | |
| DTT | 3.5 mM | | |
| B-Mercaptoethanol | 0.25 mM | | |
| EDTA | 1 mM | | |
| Glycerol | 50% | | |

As shown below in TABLE 16, efficient assembly requires the presence of the cell extract.

TABLE 16

| Oligonucleotides and Cell Extract Result in Efficient Assembly | | | | | |
|---|---|---|---|---|---|
| Extract | Oligos | CE (%) | STDEV | CFU/plate | STDEV |
| – | – | 2.8 | 0.9 | 288.7 | 58.8 |
| – | + | 40.6 | 5.6 | 160.7 | 80.9 |
| + | – | 2.5 | 0.6 | 327.0 | 91.1 |
| + | + | 93.7 | 1.5 | 514.0 | 145.5 |

Oligos: PS (partially phosphorothioated oligonucleotides) complementary
Extract: redET cells
Configuration: 1 vector + 1 PCR insert In some instances partially phosphorothioated oligonucleotides (a sulfur atom for a non-bridging oxygen in the phosphate backbone of an oligo) were used in which phosphorothioate bonds close to the 5' terminus of the oligonucleotides were introduced to render these oligonucleotides resistant to exonuclease degradation.

As shown below in TABLE 17, the manner in which the insert is prepared has little effect on cloning efficiency.

TABLE 17

| PCR-Amplified DNA vs Precloned and Restriction Enzyme Excised Fragments | | | | |
|---|---|---|---|---|
| Conditions | CE (%) | STDEV | CFU/plate | STDEV |
| (–) oligos | 2.6 | 3.7 | 225.0 | 84.9 |
| PCR fragment | 95.7 | 0.2 | 4995.0 | 551.5 |
| BglII | 94.4 | 1.4 | 1650.0 | 403.1 |
| PacI | 94.7 | 4.5 | 1695.0 | 636.4 |

Oligos: PS complementary
Extract: redET cells
Configuration: 1 vector + 1 insert (PCR or restriction enzyme digested)

RedET cells, as referred to herein, are *E. coli* cells that express redET genes. The data shown in TABLE 18 demonstrates that the redET gene products are not required for efficient OSA, at least for the assembly of two inserts. In some instances, the presence of redET gene products may be beneficial in that they may increase assembly efficiency or be necessary for complex assemblies (e.g., assemblies involving five or more inserts).

TABLE 18

| redET Genes are not Required for OSA | | | | | |
|---|---|---|---|---|---|
| Extract | Oligos | CE (%) | STDEV | CFU/plate | STDEV |
| DH10B | – | 0.0 | 0.0 | 125.0 | 49.5 |
| DH10B | + | 88.0 | 5.2 | 715.0 | 162.6 |
| redET | – | 0.0 | 0.0 | 150.0 | 14.1 |
| redET | + | 79.4 | 11.3 | 675.0 | 162.6 |

Oligos: PS offset (Offset here refers to 30 overlapped nt (dsDNA) and 2 x 30 nt (ssDNA))
Extract: redET or DH10B cells
Configuration: 1 vector + 2 inserts The data shown in TABLE 19 demonstrates that OSA can be used to assemble at least three insert nucleic acid molecules.

TABLE 19

| Up to Three Inserts, at Least 50% Cloning Efficiency | | | | |
|---|---|---|---|---|
| Type | CE (%) | STDEV | CFU/plate | STDEV |
| 1 insert redET | 93.7 | 1.5 | 5140.0 | 1455.2 |
| 2 inserts | 88.0 | 5.2 | 715.0 | 162.6 |
| 3 inserts 45 min inc | 51.6 | 14.1 | 50.0 | 2.8 |

Oligos: PS complementary or offset
Extract: redET or DH10B
Configuration: 1 vector + 1 to 3 inserts Low Volume PCR Based Nucleic Acid Assembly

TABLE 20

| PCR Amplification Conditions used to Miniaturize the Gene Synthesis Reactions | | | | | |
|---|---|---|---|---|---|
| | Sample | 1 | 2 | 3 | 4 |
| 1st PCR | Rxn Vol. | 50 μl | 33 nl | 50 μl | 33 nl |
| | PCR Chamber | 0.2 ml PCR tube | OA plate (IOM48) | 0.2 ml PCR tube | OA plate (IOM48) |
| | PCR Machine | Veriti ® Thermal Cycler | Applied Biosystems ® GeneAmp ® PCR System 9700 | Veriti ® Thermal Cycler | Applied Biosystems ® GeneAmp ® PCR System 9700 |
| | Stage 1 | 98° C., 30 sec | 98° C., 30 sec | 98° C., 30 sec | 98° C., 30 sec |
| | Stage 2 (×15 cycles) | 95° C., 10 sec (40% ramping) | 95° C., 10 sec (40% ramping) | 95° C., 10 sec (40% ramping) | 95° C., 10 sec (40% ramping) |
| | | 60° C., 30 sec | 55° C., 30 sec | 60° C., 30 sec | 55° C., 30 sec |
| | | 72° C., 1 min | 67° C., 1 min | 72° C., 1 min | 67° C., 1 min |
| | Stage 3 | 72° C., 2 min | 67° C., 2 min | 72° C., 2 min | 67° C., 2 min |
| | | 4° C., ∞ | 4° C., ∞ | 4° C., ∞ | 4° C., ∞ |
| | Heat Cover | Yes | Yes* | Yes | Yes* |
| 2nd PCR | Rxn vol. | 50 μl | 50 μl | 33 nl | 33 nl |
| | PCR Chamber | 0.2 ml PCR tube | 0.2 ml PCR tube | OA plate (IOM49) | OA plate (IOM50) |
| | PCR Machine | Veriti ® Thermal Cycler | Veriti ® Thermal Cycler | Applied Biosystems ® GeneAmp ® PCR System 9700 | Applied Biosystems ® GeneAmp ® PCR System 9700 |

TABLE 20-continued

| | | PCR Amplification Conditions used to Miniaturize the Gene Synthesis Reactions | | |
|---|---|---|---|---|
| Sample | 1 | 2 | 3 | 4 |
| Stage 1 | 98° C., 30 sec | 98° C., 30 sec | 98° C., 30 sec | 98° C., 30 sec |
| Stage 2 | 95° C., 10 sec | 95° C., 10 sec | 95° C., 10 sec | 95° C., 10 sec |
| (×15 | (40% | (40% | (40% | (40% |
| cycles) | ramping) | ramping) | ramping) | ramping) |
| | 60° C., 30 sec | 60° C., 30 sec | 55° C., 30 sec | 55° C., 30 sec |
| | 72° C., 1 min | 72° C., 1 min | 67° C., 1 min | 67° C., 1 min |
| Stage 3 | 72° C., 5 min | 72° C., 5 min | 67° C., 5 min | 67° C., 5 min |
| | 4° C., ∞ | 4° C., ∞ | 4° C., ∞ | 4° C., ∞ |
| Heat Cover | Yes | Yes | Yes* | Yes* |

*Paper cushion was located between heat cover and OA plate

Figure 24B:
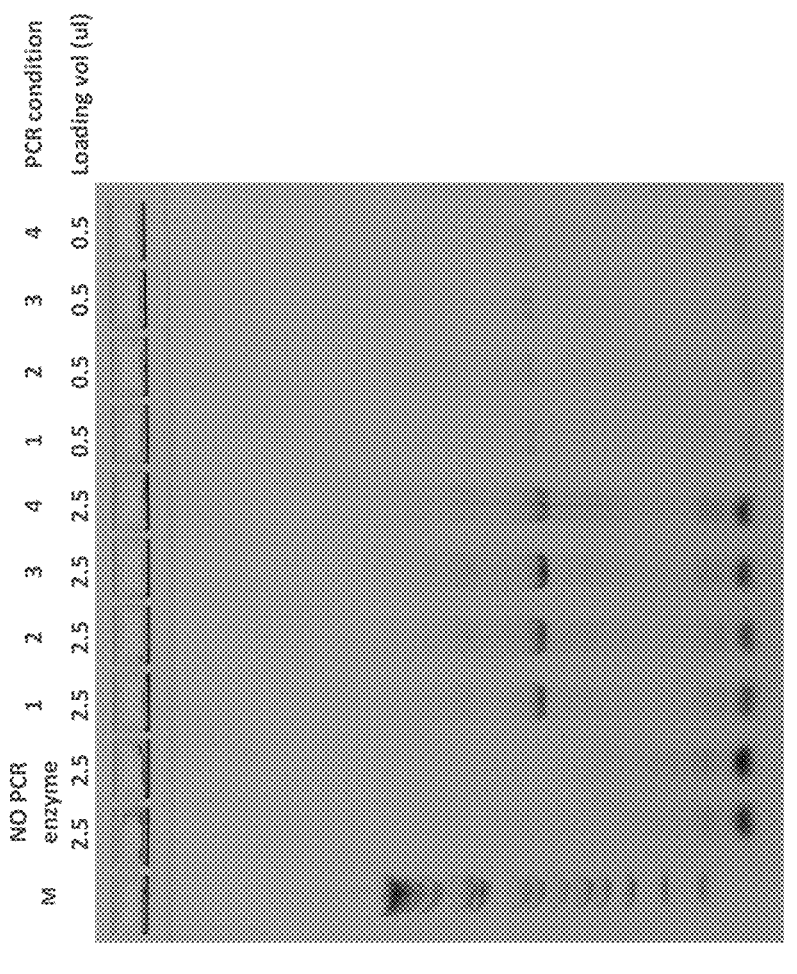
FIGS. 24A-24B show gel images of results of green fluorescent protein gene synthesis using standard reactions and the OPENARRAY™ system (Life Technologies Corp.).
Figure 24A:
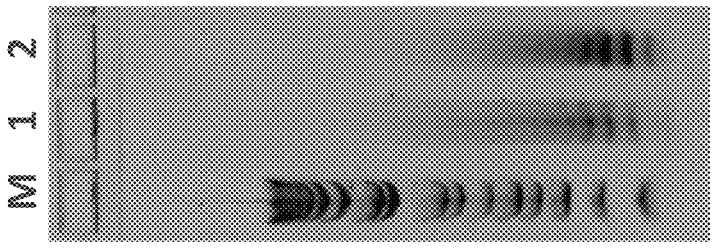

The data shown in FIGS. 24A-24B was generated using nucleic acid molecules assembled by the methods shown in TABLE 20 and shows nucleic acid assembly in volumes as low as 33 nanoliters. Specific reaction conditions details are set out above. One item not shown for the assembly reactions are the specific sequences of the assembled nucleic acid molecules. It is believed that the sequences of the nucleic acid molecules assembled will not significantly impact assembly data. However, in some instances, cycling conditions may need to be adapted for optimal efficiency.

Embodiments may be in accordance with following numbered clauses:

1. A multiwell plate for non-template directed synthesis of nucleic acid molecules, the plate comprising:
   (a) at least one bead located in each of a plurality of wells of the plate, and
   (b) an electrochemically generated acid being present in one or more well,
   wherein the bead is between 0.1 μm and 100 μm in diameter.

2. The multiwell plate of clause 1, wherein the number of wells in the plate is between 10 and 10,000,000.

3. The multiwell plate of any one of the preceding clauses, wherein the total volume of each well is between 0.1 μl and 50 μl.

4. The multiwell plate of any one of the preceding clauses, wherein each well is operably connected to a pair of electrodes.

5. The multiwell plate of any one of the preceding clauses, wherein the wells of the plate are connected to microfluidic channels for the introduction and removal of reagents.

6. A method for the generation of an assembled nucleic acid molecule, the method comprising:
   (a) synthesizing a plurality of nucleic acid molecules, wherein each nucleic acid molecule is prepared in a well of a plate in an average amount of from about 0.001 nanomoles to about 1,000 nanomoles;
   (b) combining the nucleic acid molecules generated in (a) to produce a pool;
   (c) joining some or all of the nucleic acid molecules present in the pool formed in (b) to form a plurality of larger nucleic acid molecules;
   (d) eliminating nucleic acid molecules which contain sequence errors from the plurality of larger nucleic acid molecules formed in (c) to produce an error corrected nucleic acid molecule pool; and
   (e) assembling the nucleic acid molecules in the error corrected nucleic acid molecule pool to form the assembled nucleic acid molecule.

7. The method of clause 6, wherein the joining in (c) is mediated by polymerase chain reaction and/or ligases.

8. The method of any one of clauses 6 or 7, wherein the assembled nucleic acid molecule is composed of at least five nucleic acid molecules.

9. The method of any one of clauses 6 to 8, wherein the assembled nucleic acid molecule is composed of between five and five thousand nucleic acid molecules.

10. The method of any one of clauses 6 to 9, wherein the assembled nucleic acid molecule is at least 20 kilobases.

11. The method of any one of clauses 6 to 10, wherein the assembled nucleic acid molecule is between 10 kilobases and 1 megabase.

12. The method of any one of clauses 6 to 11, wherein the assembled nucleic acid molecule is closed, circular.

13. The method of any one of clauses 6 to 12, wherein the assembled nucleic acid molecule is a plasmid.

14. The method of any one of clauses 6 to 13, wherein two or more assembled nucleic acid molecule are simultaneously formed.

15. The method of any one of clauses 6 to 14, wherein assembly of the nucleic acid molecules in the error corrected nucleic acid molecule pool occurs in a fungal cell.

16. The method of any one of clauses 6 to 15, wherein step (b) further comprises combining nucleic acid molecules generated in (a) with nucleic acid molecules obtained by other means to form a pool, wherein said other means include PCR, restriction enzyme digest or exonuclease treatment.

17. The method of any one of clauses 6 to 16, wherein the assembled nucleic acid molecule generated in (e) is assembled and introduced into a cloning vector.

18. A method for producing a product nucleic acid molecule, the method comprising:
   (a) designing the product nucleic acid molecule of between 0.1 kilobases and 500 kilobases in size, wherein the product nucleic acid molecule is defined by nucleotide sequence;
   (b) synthesizing a plurality of individual nucleic acid molecules which differ in nucleotide sequence, wherein each individual nucleic acid molecule is synthesized to prepare a quantity of between $1.0 \times 10^3$ and $1.0 \times 10^9$ copies and wherein the individual nucleic acid molecules are capable of hybridizing with one or more of the other individual nucleic acid molecules;
   (c) combining the individual nucleic acid molecules synthesized in
   (b) under conditions which allow for hybridization of the individual nucleic acid molecules under conditions which allow for the formation of at least one larger nucleic acid molecule; and
   (d) combining the at least one larger nucleic acid molecule formed in (c) with one or more additional nucleic acid molecules to form the product nucleic acid molecule, wherein the product nucleic acid molecule contains less than one sequence error per kilobase.

19. The method of clause 18, wherein the product nucleic acid molecule is of a size selected from the groups consisting of:
- (a) between 0.1 kilobases and 300 kilobases;
- (b) between 10 kilobases and 200 kilobases;
- (c) between 10 kilobases and 100 kilobases; and
- (d) between 10 kilobases and 50 kilobases.

20. The method of any one of clauses 18 or 19, wherein an error correction process is employed after step (b) or after step (d).

21. The method of any one of clauses 18 to 20, wherein each individual nucleic acid molecule is synthesized to prepare a quantity selected from the group consisting of:
- (a) between $5.0 \times 10^3$ and $1.0 \times 10^9$ copies;
- (b) between $1.0 \times 10^6$ and $1.0 \times 10^9$ copies;
- (c) between $1.0 \times 10^7$ and $1.0 \times 10^8$ copies;
- (d) between $2.0 \times 10^7$ and $1.0 \times 10^9$ copies;
- (e) between $5.0 \times 10^7$ and $1.0 \times 10^9$ copies;
- (f) between $7.0 \times 10^7$ and $1.0 \times 10^9$ copies;
- (g) between $2.0 \times 10^7$ and $8.0 \times 10^8$ copies; and
- (h) between $2.0 \times 10^7$ and $5.0 \times 10^8$ copies.

22. The method of any one of clauses 18 to 21, wherein polymerase chain reactions are used to amplify the at least one larger nucleic acid molecule formed in step (c).

23. The method of any one of clauses 18 to 22, wherein the product nucleic acid molecule is self replicable.

24. The method of any one of clauses 18 to 23, wherein the self replicable nucleic acid molecule is a plasmid.

25. The method of any one of clauses 18 to 24, wherein the individual nucleic acid molecules are synthesized on beads, wherein each bead is containing in a well.

26. The method of any one of clauses 18 to 25, wherein the beads are of a size selected from the group consisting of:
- (a) between 5 μm and 100 μm in diameter;
- (b) between 20 μm and 100 μm in diameter;
- (c) between 28 and 32 μm in diameter;
- (d) between 5 μm and 60 μm in diameter; and
- (e) between 10 μm and 100 μm in diameter.

27. A method for the generation of a self replicating nucleic acid molecule, the method comprising:
- (a) synthesizing a plurality of nucleic acid molecules, wherein each nucleic acid molecule is prepared in a microquantity in the well of a plate;
- (b) joining some or all of the nucleic acid molecules present in the pool formed in (a) to form a plurality of larger nucleic acid molecules; and
- (c) assembling the plurality of larger nucleic acid molecules to form the self replicating nucleic acid molecule.

28. The method of clause 27, wherein the self replicating nucleic acid molecule is a chromosome or a plasmid.

29. The method of any one of clauses 27 or 28, wherein the self replicating nucleic acid molecule is a genome.

30. The method of any one of clauses 27 to 29, wherein the genome is a viral genome, a nuclear genome, an organelle genome, or a genome of a prokaryotic cell.

31. A method for synthesizing and assembling a nucleic acid molecule which encodes more than one expression product, the method comprising:
- (a) synthesizing a plurality of nucleic acid molecules, wherein each nucleic acid molecule is prepared in a microquantity;

- (b) joining some or all of the nucleic acid molecules present in the pool formed in (a) to form a plurality of larger nucleic acid molecules; and
- (c) assembling the plurality of larger nucleic acid molecules to form the nucleic acid molecule which encodes more than one expression product.

32. The method of clause 31, wherein the more than one expression products are proteins that are involved in the same biological pathway.

33. The method of any one of clauses 31 or 32, wherein the more than one expression products are proteins which are involved in the same biological pathway are enzymes that catalyze a series of chemical reactions in a biological pathway.

34. The method of any one of clauses 31 to 33, wherein the chemical reactions in the same biological pathway are sequential reactions.

35. The method of any one of clauses 31 to 34, wherein the biological pathway results in an end product selected from the group consisting of:
- (a) a biofuel precursor;
- (b) an antibiotic or antibiotic precursor;
- (c) a food component; and
- (d) an industrial enzyme.

36. The method of any one of clauses 31 to 35, wherein the biofuel precursor is an alcohol selected from the group consisting of:
- (a) butanol;
- (b) pentanol;
- (c) hexanol;
- (d) heptanol; and
- (e) octanol.

37. The method of any one of clauses 31 to 36, wherein the food component is an amino acid selected from the group consisting of:
- (a) L-lysine;
- (b) L-threonine;
- (c) L-methionine;
- (d) L-leucine;
- (e) L-isoleucine:
- (f) L-valine, and
- (g) Homoserine.

38. The method of any one of clauses 31 to 37, wherein the assembled nucleic acid molecule is introduced into a prokaryotic cell.

39. The method of any one of clauses 31 to 38, wherein the prokaryotic cell is a *Corynebacterium*.

40. The method of any one of clauses 31 to 39, wherein the *Corynebacterium* is *Corynebacterium glutamicum*.

41. A non-transitory computer-readable storage medium encoded with instructions, executable by a processor, for generating assembled nucleic acid molecule, the instructions comprising instructions for:
- (a) synthesizing a plurality of nucleic acid molecules, wherein each nucleic acid molecule is prepared in a microquantity in the well of a plate;
- (b) combining the nucleic acid molecules generated in (a) to produce a pool;
- (c) joining some or all of the nucleic acid molecules present in the pool formed in (b) to form a plurality of larger nucleic acid molecules;
- (d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

42. A system for generating assembled nucleic acid molecule, the system comprising:

a processor; and a memory encoded with processor-executable instructions for:

(a) synthesizing a plurality of nucleic acid molecules, wherein each nucleic acid molecule is prepared in a microquantity in the well of a plate;

(b) combining the nucleic acid molecules generated in (a) to produce a pool;

(c) joining some or all of the nucleic acid molecules present in the pool formed in (b) to form a plurality of larger nucleic acid molecules;

(d) eliminating nucleic acid molecules which contain sequence errors from the plurality of larger nucleic acid molecules formed in (c) to produce an error corrected nucleic acid molecule pool; and (e) assembling the nucleic acid molecules in the error corrected nucleic acid molecule pool to form the assembled nucleic acid molecule.

All publications, patents and patent applications mentioned in this Specification are indicative of the level of skill of those of ordinary skill in the art and are herein incorporated by reference to the same extent as if each individual publication, patent, or patent applications was specifically and individually indicated to be incorporated by reference.

The invention being thus described, one skilled in the art would recognize that the invention may be varied in many ways. Such variations are not to be regarded as a departure from the spirit and scope of the invention, and all such modifications as would be obvious to one of ordinary skill in the art are intended to be included within the scope of the following claims.

What is claimed is:

1. A method for the generation of an assembled nucleic acid molecule, the method comprising:

(a) synthesizing a plurality of nucleic acid molecules, wherein each nucleic acid molecule is prepared in a well of a plate in an average amount of from 0.001 nanomoles to 1,000 nanomoles;

(b) combining the nucleic acid molecules generated in (a) to produce a pool of single-stranded nucleic acid molecules;

(c) generating double-stranded nucleic acid molecules from nucleic acid molecules present in the pool of single-stranded nucleic acid molecules formed in step (b) to generate a pool of double-stranded nucleic acid molecules;

(d) eliminating nucleic acid molecules which contain sequence errors from the pool of double-stranded nucleic acid molecules formed in step (c) by mismatch endonuclease correction to produce an error corrected pool of double-stranded nucleic acid molecules; and (e) simultaneously assembling the nucleic acid molecules in the error corrected pool of double-stranded nucleic acid molecules and an acceptor nucleic acid molecule to form the assembled nucleic acid molecule.

2. The method of claim 1, wherein synthesis of the nucleic acid molecules on beads present in the wells of the plate involves deblocking in step (a) by an acid generated in a redox reaction mixture in the wells of the plate.

3. The method of claim 2, wherein the redox reaction mixture in the wells of the plate contains hydroquinone.

4. The method of claim 1, wherein the assembling in step (e) is mediated by polymerase chain reaction.

5. The method of claim 1, wherein the pool of double-stranded nucleic acid molecules have blunt termini.

6. The method of claim 1, wherein the assembled nucleic acid molecule is closed, circular.

7. The method of claim 6, wherein the assembled nucleic acid molecule is a plasmid.

8. The method of claim 1, wherein the mismatch endonuclease correction comprises:

(i) denaturing the double-stranded nucleic acid molecules in the pool formed in step (c);

(ii) re-annealing the denatured nucleic acid molecules to form double-stranded nucleic acid molecules comprising mismatched base pairs at nucleotide positions corresponding to sequence errors; and (iii) contacting the re-annealed nucleic acid molecules with at least one mismatch endonuclease under conditions suitable for cleaving the nucleic acid molecules at the mismatched base pairs.

9. The method of claim 8, wherein the at least one mismatch endonuclease is selected from T7 Endonuclease 1, endonuclease VII, RES I endonuclease, CEL I endonuclease, and/or SP endonuclease.

10. The method of claim 8, wherein the at least one mismatch endonuclease is T7 Endonuclease 1 and wherein step (d) further comprises adding a DNA ligase to the error corrected pool of double-stranded nucleic acid molecules.

11. The method of claim 1, wherein the generating double-stranded nucleic acid molecules in step (c) comprises joining some or all of the nucleic acid molecules present in the pool formed in (b) to form a plurality of larger nucleic acid molecules; wherein the joining in step (c) is mediated by polymerase chain reaction and/or ligases.

12. The method of claim 1, wherein step (b) further comprises combining nucleic acid molecules generated in (a) with nucleic acid molecules obtained by other means to form a pool, wherein said other means include PCR, restriction enzyme digest, or exonuclease treatment.

13. The method of claim 1, wherein two or more nucleic acid molecules are simultaneously formed.

14. The method of claim 1, wherein the plate is a microfluidic chip.

* * * * *

SEQUENCE LISTING

```
<160> NUMBER OF SEQ ID NOS: 44

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcgcatgcg                                                          10

<210> SEQ ID NO 2
<211> LENGTH: 15
<212> TYPE: DNA
<213> ORGANISM: Enterobacteria phage lambda

<400> SEQUENCE: 2 gctttttttat actaa                                                   15

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaggtaccgt caatttaatt aattttcagg atgacgcgga acttgccaca cg            52

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgaaattctt ggctattaca acagactgcc ttcagatctt agcttatggc aat           53

<210> SEQ ID NO 5
<211> LENGTH: 53
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 5
caagagagca agctcatcat tctggccagt ggtggacccc aagccttagt aaa                53

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cataatgagg acctacactt atgagaagct tctgtggacc acaagcagag tgc                53

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgaaggtgct gtctgtctgc tctagcaaca agccggccat tgtagaagct ggt                53

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggatgcagg cactggggct tcatctgaca gacccaagtc agcgacttgt tca                53

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaactgtctt tggactctca gaaacctttc agatgcagcg actaagcagg aag                53

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggatggaagg cctccttggg actctagtgc attgtcttct ggcgcgccc aac                 53

<210> SEQ ID NO 11
<211> LENGTH: 52
<212> TYPE: DNA
<213> ORGANISM: Artificial Sequence
<220> FEATURE:
```

<223> OTHER INFORMATION: Description of Artificial Sequence: Synthetic
       oligonucleotide

<400> SEQUENCE: 11
tgcaattcct gaggcgacaa aagcgctaaa cgatgaggcc caggtggtag tt                52

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 12
aataaagctg ctgttatggt ccatcagctt tccaaaaagg aagcttccag ac                52

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 13
atgccatcat gcgctcccct cagatggtgt ctgccattgt acgcaccatg ca                52

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 14
gaatacaaat gatgtagaga cagctcgttg tactgctggg actctgcaca ac                52

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 15
ctttctcacc accgcgaggg cttgctggcc atctttaagt ctggtggcat cc                52

<210> SEQ ID NO 16
<211> LENGTH: 53
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 16
cagcgctggt gaaaatgctt gggtcaccag tggattctgt actgttctac gcc               53

<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 17
atcacgacac tgcataatct cctgctccat caggaaggag ctaaaatggc agt          53

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgcctagct ggtggactgc agaaaatggt tgctttgctc aacaaaacaa acg          53

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcgcctcagg aattgcacgt gtggcaagtt ccgc                               34

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgatgagctt gctctcttga ttgccataag ctaagatctg                         40

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cataagtgta ggtcctcatt atgtttacta aggcttgggg tcc                     43

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagacagaca gcaccttcag cactctgctt gtggtcc                            37

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cccagtgcct gcatcccacc agcttctaca atggcc                                36

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgagagtcc aaagacagtt ttgaacaagt cgctgacttg                             40

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caaggaggcc ttccatccct tcctgcttag tcgctg                                36

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggaccataac agcagcttta ttaactacca cctgggcctc                             40

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggagcgcatg atggcatgtc tggaagcttc ctttttgg                              38

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgtctcta catcatttgt attctgcatg gtgcgtacaa tgg                        43

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 29
tcgcggtggt gagaaaggtt gtgcagagtc ccagc                                35

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcattttcac cagcgctggg atgccaccag acttaaag                             38

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gagattatgc agtgtcgtga tggcgtagaa cagtacagaa tc                        42

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccaccagcta ggcgcactgc cattttagct ccttc                               35

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctgttgtaat agccaagaat ttcacgtttg ttttgttgag caaag                    45

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtcttgtgct ccaggcgcgc caagaagaca atgcacta                            38

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
```

```
cgtgtcttgt ccaggtaccg tcaatttaat taattttc                           38
```

<210> SEQ ID NO 36
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
acccgtaaag cgagtttagt tttgaaaaac aaatgacata atgacatcat cccctgattg    60
tgttttaca                                                           69
```

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
aattctaccc gtaaagcgag tttagttttg aaaaac                             36
```

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
aatgacatca tccctgatt gtgttttaca agtaga                              36
```

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: CDS
<222> LOCATION: (1)..(33)

<400> SEQUENCE: 39

```
ttc ctt cct gct act ggt ggc gtt ttc cgu aat                         33
Phe Leu Pro Ala Thr Gly Gly Val Phe Arg Asn
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40

```
Phe Leu Pro Ala Thr Gly Gly Val Phe Arg Asn
1               5                   10

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 41 ttc ctc ccc gcc acc ggc ggc gtc ttc aga aat                           33
Phe Leu Pro Ala Thr Gly Gly Val Phe Arg Asn
1               5                   10

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 42 ttc cta cca gcc act gga ggc gtc ttc agg aat                           33
Phe Leu Pro Ala Thr Gly Gly Val Phe Arg Asn
1               5                   10

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 43 ttc ctt ccg gca aca ggt ggg gtg ttc cgc aat                           33
Phe Leu Pro Ala Thr Gly Gly Val Phe Arg Asn
1               5                   10

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: CDS
<222> LOCATION: (1)..(33)

<400> SEQUENCE: 44 ttc ctt ccc gcg acc ggt ggg gta ttc cgu aac                           33
Phe Leu Pro Ala Thr Gly Gly Val Phe Arg Asn
1               5                   10
```